(12) United States Patent
Zhu et al.

(10) Patent No.: US 9,175,318 B2
(45) Date of Patent: Nov. 3, 2015

(54) REDUCING BYPRODUCTION OF MALONATES BY YEAST IN A FERMENTATION PROCESS

(75) Inventors: Quinn Qun Zhu, West Chester, PA (US); Zhixiong Xue, Chadds Ford, PA (US)

(73) Assignee: E. I. DUPONT DE NEMOURS AND COMPANY, Wilmington, DE (US)

( * ) Notice: Subject to any disclaimer, the term of this patent is extended or adjusted under 35 U.S.C. 154(b) by 944 days.

(21) Appl. No.: 12/637,877

(22) Filed: Dec. 15, 2009

(65) Prior Publication Data

US 2010/0159558 A1 Jun. 24, 2010

Related U.S. Application Data

(60) Provisional application No. 61/138,922, filed on Dec. 18, 2008.

(51) Int. Cl.
*C12P 7/64* (2006.01)
*C12N 9/00* (2006.01)

(52) U.S. Cl.
CPC .............. *C12P 7/6427* (2013.01); *C12N 9/93* (2013.01); *C12P 7/6472* (2013.01)

(58) Field of Classification Search
None
See application file for complete search history.

(56) References Cited

U.S. PATENT DOCUMENTS

| | | | |
|---|---|---|---|
| 6,939,691 B1 | 9/2005 | Khosla et al. | |
| 7,794,701 B2 * | 9/2010 | Damude et al. | 424/93.2 |
| 7,871,804 B2 * | 1/2011 | Cirpus et al. | 435/193 |
| 2003/0073205 A1 | 4/2003 | Arslanian et al. | |

FOREIGN PATENT DOCUMENTS

| | | |
|---|---|---|
| WO | WO2006044289 A2 | 4/2006 |
| WO | 2006124999 A2 | 11/2006 |
| WO | 2006125000 A2 | 11/2006 |

OTHER PUBLICATIONS

Magnuson et al. (FEBS, vol. 299, No. 3, 1992, pp. 262-266).*
Forster et al.( Appl. Microbiol. Biotechnol. (2007), vol. 75, pp. 1409-1417) Beaudoin et al. (PNAS, vol. 97, No. 12, pp. 6421-6426).*
Sharifia et al. (J. Ind. Microbiol. Biotechnol. 35: 1253-1259, 2008.*
Chen et al. (The Plant Cell, vol. 23, pp. 2247-2262, Jun. 2011).*
Shen (Current Opinion in Chem. Biol., vol. 7, 2003, pp. 285-295).*
International Search Report and Written Opinion of the International Searching Authorized, PCT International Application PCT/US2009/068000, May 27, 2010.
Young, J. P. W. et al., The Genome of *Rhizobium leguminosarum* Has Recognizable Core and Accessory Components, Genome Biology, vol. 7, No. 4 (2006), Article R34.
Database Uniprot, Subname: Full=Putative Malonyl COA Synthetase, Database Accession No. Q1MKL6, 2006.
Annex to Form PCT/ISA/206, Communication Relating to the Results of the Partial International Search, PCT International Application No. PCT/US2009/068000, Apr. 6, 2010.
Y. S. Kim et al., Purification and Properties of Malonyl-COA Synthetase From *Rhizobium japonicum*, Biochem.J., 273 (1991), pp. 511-516.
Y. S. Kim et al., Steady-State Kinetics of Malonyl-COA Synthetase From *Bradyrhizobium japonicum* and Evidence for Malonyl-AMP Formation in the Reaction, Biochem.J., 297 (1994), pp. 327-333.
F. Lombo et al., Enhancing the Atom Economy of Polyketide Biosynthetic Processes Through Metabolic Engineering, Biotechnol. Prog., 17 (2001), pp. 612-617.
J-W. Jong et al., The Active Site and Substrates Binding Mode of Malonyl-COA Synthetase Determined by Transferred Nuclear Overhauser Effect Spectroscopy, Site-Directed Mutagenesis, and Comparative Modeling Studies, Protein Science, 9 (2000), pp. 1294-1303.
J. H. An et al., A Gene Cluster Encoding Malonyl-COA Decarboxylase (MATA) Malonyl-COA Synthetase (MATB) and a Punative Dicarboxylate Carrier Protein (MATC) in *Rhizobium trifolii*, Cloning, Sequencing and Expression of the Enzymes in *Escherichia coli*, Eur. J. Biochem., 257 (1998), pp. 395-402.

* cited by examiner

*Primary Examiner* — Hope Robinson

(57) ABSTRACT

Described are methods of reducing the amount of byproduct organic acids during fermentation of an organism, based on expression of a heterologous malonyl-CoA synthetase. A polyunsaturated fatty acid ["PUFA"]-producing strain of the oleaginous yeast *Yarrowia lipolytica* was engineered to express a heterologous malonyl-CoA synthetase gene. The expression did not effect the production of PUFAs, but did result in a reduced amount of malonates when compared to the amount of malonates produced in the parental strain not expressing malonyl-CoA synthetase.

10 Claims, 8 Drawing Sheets

Figure 2:
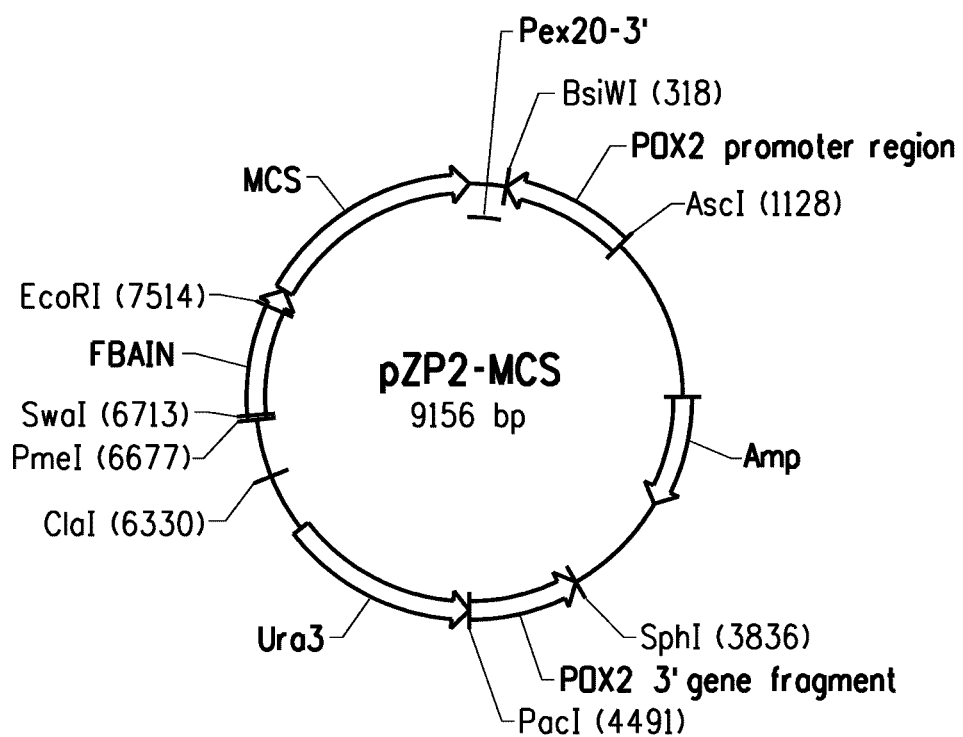

```
  1                                                        50
(1)   ATGGTCTCCAACCACCTGTTCGACGCCATGCCGAGCTGCCGCTCCCGGAGA  (SEQ ID NO:1)
(1)   ---GTGAGCAACCATCTTTTCGACGCCATGCCGGGCTGCCGCGCCCGGTGA  (SEQ ID NO:3)
 51                                                       100
(51)  CGCACCTTTCATTCGAATCGACACAACGCTCGGACTTACGATGACG       (SEQ ID NO:1)
(48)  CGCACCGTTCATCCGATCGATAAACGCGCACATGGACCTATGATGACG    (SEQ ID NO:3)
101                                                       150
(101) CCATTGCTCTTTCCGGTCGAATCGCTCGGAGCTATGGACGCACTCGGCATT  (SEQ ID NO:1)
(98)  CGATCGCTCTTTCCGGCCGTATTGCCGGCGACGCGCTCGGCATT        (SEQ ID NO:3)
151                                                       200
(151) CGACCCGGAGACAGAGTTGCCGTGCAGGTCGAGAAGTCTGCCGAGGCGTT   (SEQ ID NO:1)
(148) CGCCCCGGCGACCGGGGTGCGGTGCAGGTCGAGAAAAGTGCCGAGGCGTT  (SEQ ID NO:3)
201                                                       250
(201) GATTCTCTACCTGGCCTGTCTCTTCGAACCGGAGCTGTCTACCTGCCTCTCA (SEQ ID NO:1)
(198) GATCCTCTATCTCGCCTGTCTCTTCGAACGCGGCGCTGTCTACCTGCCTCA  (SEQ ID NO:3)
251                                                       300
(251) ACACTGCCTACACCCTGGCCGAGCTCGACTACTTCATCGGCGATGCCGAA   (SEQ ID NO:1)
(248) ACACCGCCTATACGCTGGCTGAGCTCGATTACTTTATCGGCGATGCGGAG   (SEQ ID NO:3)
301                                                       350
(301) CCGCGTCTGGTGGTCGTTGCTCCCCGCAGCTCGAGGTGGCGTGGAGACAAT  (SEQ ID NO:1)
(298) CCGCGTTTGGTGGTTGCGCCGGCGGCGGCGTCGAGGCGCGTGGAGACAAT   (SEQ ID NO:3)
351                                                       400
(351) TGCCAAGCGACACGGTGCTATCGTCGAAACCCTCGACGCCGATGGACGAG   (SEQ ID NO:1)
(348) CGCCAAGCGCCACGGGCGCCGATCGTCGAAACGCTCGATGCTCGATGGCCGCG (SEQ ID NO:3)
401                                                       450
(401) GCTCCTTGCTGGACCTGCTAGAGATGAGCCTGCCGACTTTGTCGATGCT    (SEQ ID NO:1)
(398) GCTCATTGCTGGATCTCGCACGGCGATGAGCCGGCCGACTTTGTCGATGCC  (SEQ ID NO:3)
```

FIG. 1A

```
     451                                              500
(451) TCGCGATCTGCCGACGATCTGGCTGCTATTCTCTACACTTCCGGTACAAC  (SEQ ID NO:1)
(448) TCGCGTTCCGCGGATGATCTGGCCGCGATCCTCTACACGTCGGGAACGAC  (SEQ ID NO:3)
     501                                              550
(501) CGGACGATCGAAGGGTGCCATGCTTACTCATGGCAATCTGCTCTCCAACG  (SEQ ID NO:1)
(498) CGGACGCTCCAAGGGGCGATGCTCACGCATGGGAACCTGCTCTCGAACG  (SEQ ID NO:3)
     551                                              600
(551) CTCTCACCTTGCGAGACTATTGGAGAGTTACCGCAGACGATCGACTCATC  (SEQ ID NO:1)
(548) CCCTGACCTTGCGAGACTATTGGCGCGTCACCGCTGACGATCGGCTGATC  (SEQ ID NO:3)
     601                                              650
(601) CATGCCTTGCCAATCTTTCACACTCATGGTCTGTTCGTTGCTACGAACGT  (SEQ ID NO:1)
(598) CATGCCTTGCCGATCTTCCACACGCATGGGCTGTTCGTCGCCACGAACGT  (SEQ ID NO:3)
     651                                              700
(651) CACACTGCTTGCAGGAGCCTCGATGTTTCTGCTCTCCAAGTTCGATGCCG  (SEQ ID NO:1)
(648) CACACTGCTTGCCGGGCCCTCGATGTTCCTGCTGTCGAAATTCGACGCCG  (SEQ ID NO:3)
     701                                              750
(701) ACGAGGTCGTTTCTCATGCCACAGGCCACCATGCTTATGGGCGTGCCC    (SEQ ID NO:1)
(698) ACGAGGTCGTTTCACTGATGCCACAGGCAACTATGCTGATGGGCGTGCCG  (SEQ ID NO:3)
     751                                              800
(751) ACATTCTACGTTCGATTGCTGCAGAGTCCTCGACTCGAGAAGGGTGCTGT  (SEQ ID NO:1)
(748) ACCTTCTACGTGCGCCTCCTGCAAAGCCCGCGCCTCGAAAAAGGGGCGGT  (SEQ ID NO:3)
     801                                              850
(801) GGCCAGCATCAGACTGTTCATTTCTGGATCAGCTCCCTTGCTTGCCGAAA  (SEQ ID NO:1)
(798) CGCCAGCATCCGCCTCTTCATTTCCGGTTCGGCTTGCTGCCGAAA       (SEQ ID NO:3)
     851                                              900
(851) CCCACGCCGAGTTTCATGCTCGTACTGGTCACGCCATTCTCGAGCGATAC  (SEQ ID NO:1)
(848) CCCATGCCGAGTTCCATGCGCTACGCGGTCACGCCATTCTCGAGCGCTAC  (SEQ ID NO:3)
```

FIG. 1B

```
 (901) GGCATGACGGAAACCAACATGAATACTTCCAACCCCTACGAGGGCAAGCG     (SEQ ID NO:1)
                                                      950
 (898) GGCATGACGGAAACCAATATGAACACGTCCAACCCCTATGAGGGCAAACG     (SEQ ID NO:3)
                                                     1000
 (951) TATTGCCGAACCGTTGGTTTCCTCTGCCCGACGTCACTGTGCGAGTCA       (SEQ ID NO:1)
 (948) GATTGCCGGAACGGTTGGTTTCCCGCTGCCTGATGTGACGGTGCGCGTCA     (SEQ ID NO:3)
                                                     1050
(1001) CCGATCCCGCCACCGGTCTCGTTCTTCCACCTGAAGAGACTGGCATGATC     (SEQ ID NO:1)
 (998) CCGATCCCCGCCACCGGGCTCGTGCTGCCACCTGAAGAGACGGGCATGATC    (SEQ ID NO:3)
                                                     1100
(1051) GAGATCAAGGGACCCAAGCGTCTTCAAGGGCTATTGGCGAATGCCCGAAAA    (SEQ ID NO:1)
(1048) GAGATCAAGGGACCGAACGTCTTCAAGGGCTATTGGCCATGCCGAAAA       (SEQ ID NO:3)
                                                     1150
(1101) GACCGCTGCCGAGTTTACCGCAGACGTTTCTTTATCTCTGAGATCTCG       (SEQ ID NO:1)
(1098) GACCGCGGCCGAATTCACCGCCGACGTTTCTTCTTCATCAGCCGATCTCG     (SEQ ID NO:3)
                                                     1200
(1151) GCAAGATCGACCGAGAAGGTTACGTTCACATTGTGGGACGAGGCAAGGAC     (SEQ ID NO:1)
(1148) GCAAGATCGACCGGGAAGGTTATGTCCACATCGTCGGTCGCGGCAAGGAT     (SEQ ID NO:3)
                                                     1250
(1201) CTGGTTCATTTCCGGTGCCTACAACATCTATCCCAAAGAGGTCGAAGGCGA    (SEQ ID NO:1)
(1198) CTGGTGATCTCGGGTGGATACAACAACATCTATCCGAAAGAGGTCGAAGGCGA  (SEQ ID NO:3)
                                                     1300
(1251) GATCGACCAGATCGAGGGTGTGGTCGAGTCTCGCTGTCATTGGTGTTCCTC    (SEQ ID NO:1)
(1248) GATCGACCAGATCGAGGGTGTGGTTGAGAGCGCTGTGATCGGTGTGCCGC     (SEQ ID NO:3)
                                                     1350
(1301) ATCCCGATTTCGGAGAAGGTGTCACCGCTGTGTCGTGTGCAAACCTGGT      (SEQ ID NO:1)
(1298) ATCCCGATTTCGGAGAAGGCGTAACGGCTGTCGTCGTGTATGTAAGCCCGGGC  (SEQ ID NO:3)
```

FIG. 1C

```
       1351                                          1400
(1351) GCCGTTCTCGACGAAAAGAGACCATCGTGTCTGCTCTGCAGGACCGTCTTGC  (SEQ ID NO:1)
(1348) GCCGTCCTCGATGAAAAGAGACCATCGTCGTCAGCGCCCTCCAGGACCGTCTCGC (SEQ ID NO:3)
       1401                                          1450
(1401) CCGATACAAGCAACCCAAGCGGATTATCTTTGCCGACGATCTGCCTCGAA   (SEQ ID NO:1)
(1398) CCGCTACAAACAACCCAAGCGCATCATCTTCGCCGACGACCTGCCGCGCA   (SEQ ID NO:3)
       1451                                          1500
(1451) ACACTATGGGAAAGGTTCAGAAGAACATTCTTCGACAGCAATACGCCGAT   (SEQ ID NO:1)
(1448) ACACTATGGGTAAGGTTCAGAAGAATATCCTGCGGCAGCAATACGCCGAT   (SEQ ID NO:3)
       1501    1518
(1501) CTCTACACCAGACGATAA                                   (SEQ ID NO:1)
(1498) CTTTATACCAGGAGTAA                                    (SEQ ID NO:3)
```

FIG. 1D

SEQUENCE LISTING

<160> NUMBER OF SEQ ID NOS: 22

<210> SEQ ID NO 1
<211> LENGTH: 1515
<212> TYPE: DNA
<213> ORGANISM: Rhizobium leguminosarum bv. viciae 3841
<220> FEATURE:
<221> NAME/KEY: CDS
<222> LOCATION: (1)..(1515)
<223> OTHER INFORMATION: GenBank Accession No. YP_766603

<400> SEQUENCE: 1

```
gtg agc aac cat ctt ttc gac gcc atg cgg gct gcc gcg ccc ggt gac       48
Val Ser Asn His Leu Phe Asp Ala Met Arg Ala Ala Ala Pro Gly Asp
1               5                   10                  15 gca ccg ttc atc cgg atc gat aac gcg cgc aca tgg acc tat gat gac       96
Ala Pro Phe Ile Arg Ile Asp Asn Ala Arg Thr Trp Thr Tyr Asp Asp
            20                  25                  30 gcg atc gct ctt tcc ggc cgt att gcc ggc gcg atg gac gcg ctc ggc      144
Ala Ile Ala Leu Ser Gly Arg Ile Ala Gly Ala Met Asp Ala Leu Gly
        35                  40                  45 att cgc ccc ggc gac cgg gtg gcg gtg cag gtc gag aaa agt gcc gag      192
Ile Arg Pro Gly Asp Arg Val Ala Val Gln Val Glu Lys Ser Ala Glu
    50                  55                  60 gcg ttg atc ctc tat ctc gcc tgt ctt cga acc ggc gcc gtc tac ctg      240
Ala Leu Ile Leu Tyr Leu Ala Cys Leu Arg Thr Gly Ala Val Tyr Leu
65                  70                  75                  80 ccg ctc aac acc gcc tat acg ctg gct gag ctc gat tac ttt atc ggc      288
Pro Leu Asn Thr Ala Tyr Thr Leu Ala Glu Leu Asp Tyr Phe Ile Gly
                85                  90                  95 gat gcg gag ccg cgt ttg gtg gtg gtt gcg ccg gcg gct cga ggc ggc      336
Asp Ala Glu Pro Arg Leu Val Val Val Ala Pro Ala Ala Arg Gly Gly
            100                 105                 110 gtg gag aca atc gcc aag cgc cac ggc gcg atc gtc gaa acg ctc gat      384
Val Glu Thr Ile Ala Lys Arg His Gly Ala Ile Val Glu Thr Leu Asp
        115                 120                 125 gct gat ggc cgc ggc tca ttg ctg gat ctc gca cgc gat gag ccg gcc      432
Ala Asp Gly Arg Gly Ser Leu Leu Asp Leu Ala Arg Asp Glu Pro Ala
    130                 135                 140 gac ttt gtc gat gcc tcg cgt tcc gcg gat gat ctg gcc gcg atc ctc      480
Asp Phe Val Asp Ala Ser Arg Ser Ala Asp Asp Leu Ala Ala Ile Leu
145                 150                 155                 160
```

```
tac acg tcg gga acg acc gga cgc tcc aag ggg gcg atg ctc acg cat      528
Tyr Thr Ser Gly Thr Thr Gly Arg Ser Lys Gly Ala Met Leu Thr His
            165                 170                 175 ggg aac ctg ctc tcg aac gcc ctg acc ttg cga gac tat tgg cgc gtc      576
Gly Asn Leu Leu Ser Asn Ala Leu Thr Leu Arg Asp Tyr Trp Arg Val
            180                 185                 190 acc gct gac gat cgg ctg atc cat gcc ttg ccg atc ttc cac acg cat      624
Thr Ala Asp Asp Arg Leu Ile His Ala Leu Pro Ile Phe His Thr His
            195                 200                 205 ggg ctg ttc gtc gcc acg aac gtc aca ctg ctt gcc ggc gcc tcg atg      672
Gly Leu Phe Val Ala Thr Asn Val Thr Leu Leu Ala Gly Ala Ser Met
            210                 215                 220 ttc ctg ctg tcg aaa ttc gac gcc gac gag gtc gtt tca ctg atg cca      720
Phe Leu Leu Ser Lys Phe Asp Ala Asp Glu Val Val Ser Leu Met Pro
225                 230                 235                 240 cag gca act atg ctg atg ggc gtg ccg acc ttc tac gtg cgc ctc ctg      768
Gln Ala Thr Met Leu Met Gly Val Pro Thr Phe Tyr Val Arg Leu Leu
                245                 250                 255 caa agc ccg cgc ctc gaa aaa ggg gcg gtc gcc agc atc cgc ctc ttc      816
Gln Ser Pro Arg Leu Glu Lys Gly Ala Val Ala Ser Ile Arg Leu Phe
                260                 265                 270 att tcc ggt tcg gct ccc ctg ctg gcc gaa acc cat gcc gag ttc cat      864
Ile Ser Gly Ser Ala Pro Leu Leu Ala Glu Thr His Ala Glu Phe His
                275                 280                 285 gcg cgt acc ggt cac gcc att ctc gag cgc tac ggc atg acg gaa acc      912
Ala Arg Thr Gly His Ala Ile Leu Glu Arg Tyr Gly Met Thr Glu Thr
            290                 295                 300 aat atg aac acg tcc aac ccc tat gag ggc aaa cgg att gcc gga acg      960
Asn Met Asn Thr Ser Asn Pro Tyr Glu Gly Lys Arg Ile Ala Gly Thr
305                 310                 315                 320 gtt ggt ttc ccg ctg cct gat gtg acg gtg cgc gtc acc gat ccc gcc     1008
Val Gly Phe Pro Leu Pro Asp Val Thr Val Arg Val Thr Asp Pro Ala
                325                 330                 335 acc ggg ctc gtg ctg cca cct gaa gag acg ggc atg atc gag atc aag     1056
Thr Gly Leu Val Leu Pro Pro Glu Glu Thr Gly Met Ile Glu Ile Lys
                340                 345                 350 gga ccg aac gtc ttc aag ggc tat tgg cgc atg ccg gaa aag acc gcg     1104
Gly Pro Asn Val Phe Lys Gly Tyr Trp Arg Met Pro Glu Lys Thr Ala
            355                 360                 365 gcc gaa ttc acc gcc gac ggt ttc ttc atc agc ggc gat ctc ggc aag     1152
Ala Glu Phe Thr Ala Asp Gly Phe Phe Ile Ser Gly Asp Leu Gly Lys
            370                 375                 380 atc gac cgg gaa ggt tat gtc cac atc gtc ggt cgc ggc aag gat ctg     1200
Ile Asp Arg Glu Gly Tyr Val His Ile Val Gly Arg Gly Lys Asp Leu
385                 390                 395                 400 gtg atc tcg ggt gga tac aac atc tat ccg aaa gag gtc gaa ggc gag     1248
Val Ile Ser Gly Gly Tyr Asn Ile Tyr Pro Lys Glu Val Glu Gly Glu
                405                 410                 415 atc gac cag atc gag ggt gtg gtt gag agc gct gtg atc ggt gtg ccg     1296
Ile Asp Gln Ile Glu Gly Val Val Glu Ser Ala Val Ile Gly Val Pro
                420                 425                 430 cat ccc gat ttc gga gaa ggc gta acg gct gtc gtc gta tgt aag ccc     1344
His Pro Asp Phe Gly Glu Gly Val Thr Ala Val Val Val Cys Lys Pro
            435                 440                 445 ggc gcc gtc ctc gat gaa aag acc atc gtc agc gcc ctc cag gac cgt     1392
Gly Ala Val Leu Asp Glu Lys Thr Ile Val Ser Ala Leu Gln Asp Arg
450                 455                 460 ctc gcc cgc tac aaa caa ccc aag cgc atc atc ttc gcc gac gac ctg     1440
Leu Ala Arg Tyr Lys Gln Pro Lys Arg Ile Ile Phe Ala Asp Asp Leu
```

```
                465                 470                 475                 480
ccg cgc aac act atg ggt aag gtt cag aag aat atc ctg cgg cag caa        1488
Pro Arg Asn Thr Met Gly Lys Val Gln Lys Asn Ile Leu Arg Gln Gln
                        485                 490                 495 tac gcc gat ctt tat acc agg agg taa                                    1515
Tyr Ala Asp Leu Tyr Thr Arg Arg
                500

<210> SEQ ID NO 2
<211> LENGTH: 504
<212> TYPE: PRT
<213> ORGANISM: Rhizobium leguminosarum bv. viciae 3841

<400> SEQUENCE: 2

Val Ser Asn His Leu Phe Asp Ala Met Arg Ala Ala Pro Gly Asp
1               5                   10                  15

Ala Pro Phe Ile Arg Ile Asp Asn Ala Arg Thr Trp Thr Tyr Asp Asp
                20                  25                  30

Ala Ile Ala Leu Ser Gly Arg Ile Ala Gly Ala Met Asp Ala Leu Gly
            35                  40                  45

Ile Arg Pro Gly Asp Arg Val Ala Val Gln Val Glu Lys Ser Ala Glu
50                  55                  60

Ala Leu Ile Leu Tyr Leu Ala Cys Leu Arg Thr Gly Ala Val Tyr Leu
65                  70                  75                  80

Pro Leu Asn Thr Ala Tyr Thr Leu Ala Glu Leu Asp Tyr Phe Ile Gly
                85                  90                  95

Asp Ala Glu Pro Arg Leu Val Val Ala Pro Ala Ala Arg Gly Gly
                100                 105                 110

Val Glu Thr Ile Ala Lys Arg His Gly Ala Ile Val Glu Thr Leu Asp
            115                 120                 125

Ala Asp Gly Arg Gly Ser Leu Leu Asp Leu Ala Arg Asp Glu Pro Ala
        130                 135                 140

Asp Phe Val Asp Ala Ser Arg Ser Ala Asp Leu Ala Ala Ile Leu
145                 150                 155                 160

Tyr Thr Ser Gly Thr Thr Gly Arg Ser Lys Gly Ala Met Leu Thr His
                165                 170                 175

Gly Asn Leu Leu Ser Asn Ala Leu Thr Leu Arg Asp Tyr Trp Arg Val
            180                 185                 190

Thr Ala Asp Asp Arg Leu Ile His Ala Leu Pro Ile Phe His Thr His
        195                 200                 205

Gly Leu Phe Val Ala Thr Asn Val Thr Leu Leu Ala Gly Ala Ser Met
    210                 215                 220

Phe Leu Leu Ser Lys Phe Asp Ala Asp Glu Val Val Ser Leu Met Pro
225                 230                 235                 240

Gln Ala Thr Met Leu Met Gly Val Pro Thr Phe Tyr Val Arg Leu Leu
                245                 250                 255

Gln Ser Pro Arg Leu Glu Lys Gly Ala Val Ala Ser Ile Arg Leu Phe
            260                 265                 270

Ile Ser Gly Ser Ala Pro Leu Leu Ala Glu Thr His Ala Glu Phe His
        275                 280                 285

Ala Arg Thr Gly His Ala Ile Leu Glu Arg Tyr Gly Met Thr Glu Thr
    290                 295                 300

Asn Met Asn Thr Ser Asn Pro Tyr Glu Gly Lys Arg Ile Ala Gly Thr
305                 310                 315                 320

Val Gly Phe Pro Leu Pro Asp Val Thr Val Arg Val Thr Asp Pro Ala
```

```
                    325                 330                 335
Thr Gly Leu Val Leu Pro Pro Glu Glu Thr Gly Met Ile Glu Ile Lys
                340                 345                 350

Gly Pro Asn Val Phe Lys Gly Tyr Trp Arg Met Pro Glu Lys Thr Ala
            355                 360                 365

Ala Glu Phe Thr Ala Asp Gly Phe Phe Ile Ser Gly Asp Leu Gly Lys
        370                 375                 380

Ile Asp Arg Glu Gly Tyr Val His Ile Val Gly Arg Gly Lys Asp Leu
385                 390                 395                 400

Val Ile Ser Gly Gly Tyr Asn Ile Tyr Pro Lys Glu Val Glu Gly Glu
                405                 410                 415

Ile Asp Gln Ile Glu Gly Val Val Glu Ser Ala Val Ile Gly Val Pro
            420                 425                 430

His Pro Asp Phe Gly Glu Gly Val Thr Ala Val Val Cys Lys Pro
        435                 440                 445

Gly Ala Val Leu Asp Glu Lys Thr Ile Val Ser Ala Leu Gln Asp Arg
    450                 455                 460

Leu Ala Arg Tyr Lys Gln Pro Lys Arg Ile Ile Phe Ala Asp Asp Leu
465                 470                 475                 480

Pro Arg Asn Thr Met Gly Lys Val Gln Lys Asn Ile Leu Arg Gln Gln
                485                 490                 495

Tyr Ala Asp Leu Tyr Thr Arg Arg
            500

<210> SEQ ID NO 3
<211> LENGTH: 1518
<212> TYPE: DNA
<213> ORGANISM: Rhizobium leguminosarum bv. viciae 3841
<220> FEATURE:
<221> NAME/KEY: CDS
<222> LOCATION: (1)..(1518)
<223> OTHER INFORMATION: synthetic malonyl-CoA synthetase (codon-
      optimized for Yarrowia lipolytica)

<400> SEQUENCE: 3 atg gtc tcc aac cac ctg ttc gac gcc atg cga gct gcc gct ccc gga    48
Met Val Ser Asn His Leu Phe Asp Ala Met Arg Ala Ala Ala Pro Gly
1               5                   10                  15 gac gca cct ttc att cga atc gac aac gct cgg acc tgg act tac gat    96
Asp Ala Pro Phe Ile Arg Ile Asp Asn Ala Arg Thr Trp Thr Tyr Asp
            20                  25                  30 gac gcc att gct ctt tcc ggt cga atc gct gga gct atg gac gca ctc    144
Asp Ala Ile Ala Leu Ser Gly Arg Ile Ala Gly Ala Met Asp Ala Leu
        35                  40                  45 ggc att cga ccc gga gac aga gtt gcc gtg cag gtc gag aag tct gcc    192
Gly Ile Arg Pro Gly Asp Arg Val Ala Val Gln Val Glu Lys Ser Ala
    50                  55                  60 gag gcg ttg att ctc tac ctg gcc tgt ctt cga acc gga gct gtc tac    240
Glu Ala Leu Ile Leu Tyr Leu Ala Cys Leu Arg Thr Gly Ala Val Tyr
65                  70                  75                  80 ctg cct ctc aac act gcc tac acc ctg gcc gag ctc gac tac ttc atc    288
Leu Pro Leu Asn Thr Ala Tyr Thr Leu Ala Glu Leu Asp Tyr Phe Ile
                85                  90                  95 ggc gat gcc gaa ccg cgt ctg gtg gtc gtt gct ccc gca gct cga ggt    336
Gly Asp Ala Glu Pro Arg Leu Val Val Val Ala Pro Ala Ala Arg Gly
            100                 105                 110 ggc gtg gag aca att gcc aag cga cac ggt gct atc gtc gaa acc ctc    384
Gly Val Glu Thr Ile Ala Lys Arg His Gly Ala Ile Val Glu Thr Leu
        115                 120                 125
```

```
gac gcc gat gga cga ggc tcc ttg ctg gac ctt gct aga gat gag cct    432
Asp Ala Asp Gly Arg Gly Ser Leu Leu Asp Leu Ala Arg Asp Glu Pro
130                 135                 140 gcc gac ttt gtc gat gct tcg cga tct gcc gac gat ctg gct gct att    480
Ala Asp Phe Val Asp Ala Ser Arg Ser Ala Asp Asp Leu Ala Ala Ile
145                 150                 155                 160 ctc tac act tcc ggt aca acc gga cga tcg aag ggt gcc atg ctt act    528
Leu Tyr Thr Ser Gly Thr Thr Gly Arg Ser Lys Gly Ala Met Leu Thr
                165                 170                 175 cat ggc aat ctg ctc tcc aac gct ctc acc ttg cga gac tat tgg aga    576
His Gly Asn Leu Leu Ser Asn Ala Leu Thr Leu Arg Asp Tyr Trp Arg
            180                 185                 190 gtt acc gca gac gat cga ctc atc cat gcc ttg cca atc ttt cac act    624
Val Thr Ala Asp Asp Arg Leu Ile His Ala Leu Pro Ile Phe His Thr
        195                 200                 205 cat ggt ctg ttc gtt gct acg aac gtc aca ctg ctt gca gga gcc tcg    672
His Gly Leu Phe Val Ala Thr Asn Val Thr Leu Leu Ala Gly Ala Ser
    210                 215                 220 atg ttt ctg ctc tcc aag ttc gat gcc gac gag gtc gtt tct ctc atg    720
Met Phe Leu Leu Ser Lys Phe Asp Ala Asp Glu Val Val Ser Leu Met
225                 230                 235                 240 cca cag gcc acc atg ctt atg ggc gtg ccc aca ttc tac gtt cga ttg    768
Pro Gln Ala Thr Met Leu Met Gly Val Pro Thr Phe Tyr Val Arg Leu
                245                 250                 255 ctg cag agt cct cga ctc gag aag ggt gct gtg gcc agc atc aga ctg    816
Leu Gln Ser Pro Arg Leu Glu Lys Gly Ala Val Ala Ser Ile Arg Leu
            260                 265                 270 ttc att tct gga tca gct ccc ttg ctt gcc gaa acc cac gcc gag ttt    864
Phe Ile Ser Gly Ser Ala Pro Leu Leu Ala Glu Thr His Ala Glu Phe
        275                 280                 285 cat gct cgt act ggt cac gcc att ctc gag cga tac ggc atg acg gaa    912
His Ala Arg Thr Gly His Ala Ile Leu Glu Arg Tyr Gly Met Thr Glu
    290                 295                 300 acc aac atg aat act tcc aac ccc tac gag ggc aag cgt att gcc gga    960
Thr Asn Met Asn Thr Ser Asn Pro Tyr Glu Gly Lys Arg Ile Ala Gly
305                 310                 315                 320 acc gtt ggt ttt cct ctg ccc gac gtc act gtg cga gtc acc gat ccc    1008
Thr Val Gly Phe Pro Leu Pro Asp Val Thr Val Arg Val Thr Asp Pro
                325                 330                 335 gcc acc ggt ctc gtt ctt cca cct gaa gag act ggc atg atc gag atc    1056
Ala Thr Gly Leu Val Leu Pro Pro Glu Glu Thr Gly Met Ile Glu Ile
            340                 345                 350 aag gga ccc aac gtc ttc aag ggc tat tgg cga atg ccc gaa aag acc    1104
Lys Gly Pro Asn Val Phe Lys Gly Tyr Trp Arg Met Pro Glu Lys Thr
        355                 360                 365 gct gcc gag ttt acc gca gac ggt ttc ttt atc tct gga gat ctc ggc    1152
Ala Ala Glu Phe Thr Ala Asp Gly Phe Phe Ile Ser Gly Asp Leu Gly
    370                 375                 380 aag atc gac cga gaa ggt tac gtt cac att gtg gga cga ggc aag gac    1200
Lys Ile Asp Arg Glu Gly Tyr Val His Ile Val Gly Arg Gly Lys Asp
385                 390                 395                 400 ctg gtc att tcc ggt ggc tac aac atc tat ccc aaa gag gtc gaa ggc    1248
Leu Val Ile Ser Gly Gly Tyr Asn Ile Tyr Pro Lys Glu Val Glu Gly
                405                 410                 415 gag atc gac cag atc gag ggt gtg gtc gag tct gct gtc att ggt gtt    1296
Glu Ile Asp Gln Ile Glu Gly Val Val Glu Ser Ala Val Ile Gly Val
            420                 425                 430 cct cat ccc gat ttc gga gaa ggt gtc acc gct gtt gtc gtg tgc aaa    1344
Pro His Pro Asp Phe Gly Glu Gly Val Thr Ala Val Val Val Cys Lys
```

```
                        435                 440                 445
cct ggt gcc gtt ctc gac gaa aag acc atc gtg tct gct ctg cag gac      1392
Pro Gly Ala Val Leu Asp Glu Lys Thr Ile Val Ser Ala Leu Gln Asp
        450                 455                 460 cgt ctt gcc cga tac aag caa ccc aag cgg att atc ttt gcc gac gat      1440
Arg Leu Ala Arg Tyr Lys Gln Pro Lys Arg Ile Ile Phe Ala Asp Asp
465                 470                 475                 480 ctg cct cga aac act atg gga aag gtt cag aag aac att ctt cga cag      1488
Leu Pro Arg Asn Thr Met Gly Lys Val Gln Lys Asn Ile Leu Arg Gln
                485                 490                 495 caa tac gcc gat ctc tac acc aga cga taa                              1518
Gln Tyr Ala Asp Leu Tyr Thr Arg Arg
            500                 505

<210> SEQ ID NO 4
<211> LENGTH: 505
<212> TYPE: PRT
<213> ORGANISM: Rhizobium leguminosarum bv. viciae 3841

<400> SEQUENCE: 4

Met Val Ser Asn His Leu Phe Asp Ala Met Arg Ala Ala Pro Gly
1               5                   10                  15

Asp Ala Pro Phe Ile Arg Ile Asp Asn Ala Arg Thr Trp Thr Tyr Asp
                20                  25                  30

Asp Ala Ile Ala Leu Ser Gly Arg Ile Ala Gly Ala Met Asp Ala Leu
            35                  40                  45

Gly Ile Arg Pro Gly Asp Arg Val Ala Val Gln Val Glu Lys Ser Ala
        50                  55                  60

Glu Ala Leu Ile Leu Tyr Leu Ala Cys Leu Arg Thr Gly Ala Val Tyr
65                  70                  75                  80

Leu Pro Leu Asn Thr Ala Tyr Thr Leu Ala Glu Leu Asp Tyr Phe Ile
                85                  90                  95

Gly Asp Ala Glu Pro Arg Leu Val Val Val Ala Pro Ala Ala Arg Gly
            100                 105                 110

Gly Val Glu Thr Ile Ala Lys Arg His Gly Ala Ile Val Glu Thr Leu
        115                 120                 125

Asp Ala Asp Gly Arg Gly Ser Leu Leu Asp Leu Ala Arg Asp Glu Pro
    130                 135                 140

Ala Asp Phe Val Asp Ala Ser Arg Ser Ala Asp Asp Leu Ala Ala Ile
145                 150                 155                 160

Leu Tyr Thr Ser Gly Thr Thr Gly Arg Ser Lys Gly Ala Met Leu Thr
                165                 170                 175

His Gly Asn Leu Leu Ser Asn Ala Leu Thr Leu Arg Asp Tyr Trp Arg
            180                 185                 190

Val Thr Ala Asp Asp Arg Leu Ile His Ala Leu Pro Ile Phe His Thr
        195                 200                 205

His Gly Leu Phe Val Ala Thr Asn Val Thr Leu Leu Ala Gly Ala Ser
    210                 215                 220

Met Phe Leu Leu Ser Lys Phe Asp Ala Asp Glu Val Val Ser Leu Met
225                 230                 235                 240

Pro Gln Ala Thr Met Leu Met Gly Val Pro Thr Phe Tyr Val Arg Leu
                245                 250                 255

Leu Gln Ser Pro Arg Leu Glu Lys Gly Ala Val Ala Ser Ile Arg Leu
            260                 265                 270

Phe Ile Ser Gly Ser Ala Pro Leu Leu Ala Glu Thr His Ala Glu Phe
        275                 280                 285
```

```
His Ala Arg Thr Gly His Ala Ile Leu Glu Arg Tyr Gly Met Thr Glu
        290                 295                 300

Thr Asn Met Asn Thr Ser Asn Pro Tyr Glu Gly Lys Arg Ile Ala Gly
305                 310                 315                 320

Thr Val Gly Phe Pro Leu Pro Asp Val Thr Val Arg Val Thr Asp Pro
                325                 330                 335

Ala Thr Gly Leu Val Leu Pro Pro Glu Glu Thr Gly Met Ile Glu Ile
            340                 345                 350

Lys Gly Pro Asn Val Phe Lys Gly Tyr Trp Arg Met Pro Glu Lys Thr
        355                 360                 365

Ala Ala Glu Phe Thr Ala Asp Gly Phe Phe Ile Ser Gly Asp Leu Gly
    370                 375                 380

Lys Ile Asp Arg Glu Gly Tyr Val His Ile Val Gly Arg Gly Lys Asp
385                 390                 395                 400

Leu Val Ile Ser Gly Gly Tyr Asn Ile Tyr Pro Lys Glu Val Glu Gly
                405                 410                 415

Glu Ile Asp Gln Ile Glu Gly Val Val Glu Ser Ala Val Ile Gly Val
            420                 425                 430

Pro His Pro Asp Phe Gly Glu Gly Val Thr Ala Val Val Cys Lys
        435                 440                 445

Pro Gly Ala Val Leu Asp Glu Lys Thr Ile Val Ser Ala Leu Gln Asp
    450                 455                 460

Arg Leu Ala Arg Tyr Lys Gln Pro Lys Arg Ile Ile Phe Ala Asp Asp
465                 470                 475                 480

Leu Pro Arg Asn Thr Met Gly Lys Val Gln Lys Asn Ile Leu Arg Gln
                485                 490                 495

Gln Tyr Ala Asp Leu Tyr Thr Arg Arg
            500                 505

<210> SEQ ID NO 5
<211> LENGTH: 504
<212> TYPE: PRT
<213> ORGANISM: Rhizobium trifolii
<220> FEATURE:
<221> NAME/KEY: MISC_FEATURE
<222> LOCATION: (1)..(504)
<223> OTHER INFORMATION: GenBank Accession No. AF117694; GenBank
      Accession No. AAC83455

<400> SEQUENCE: 5

Met Ser Asn His Leu Phe Asp Ala Met Arg Ala Ala Pro Gly Asn
1               5                   10                  15

Ala Pro Phe Ile Arg Ile Asp Asn Thr Arg Thr Trp Thr Tyr Asp Asp
                20                  25                  30

Ala Phe Ala Leu Ser Gly Arg Ile Ala Ser Ala Met Asp Ala Leu Gly
            35                  40                  45

Ile Arg Pro Gly Asp Arg Val Ala Val Gln Val Glu Lys Ser Ala Glu
        50                  55                  60

Ala Leu Ile Leu Tyr Leu Ala Cys Leu Arg Ser Gly Ala Val Tyr Leu
65                  70                  75                  80

Pro Leu Asn Thr Ala Tyr Thr Leu Ala Glu Leu Asp Tyr Phe Ile Gly
                85                  90                  95

Asp Ala Glu Pro Arg Leu Val Val Ala Ser Ser Ala Arg Ala Gly
            100                 105                 110

Val Glu Thr Ile Ala Lys Pro Arg Gly Ala Ile Val Glu Thr Leu Asp
        115                 120                 125
```

Ala Ala Gly Ser Gly Ser Leu Leu Asp Leu Ala Arg Asp Glu Pro Ala
            130                 135                 140

Asp Phe Val Asp Ala Ser Arg Ser Ala Asp Asp Leu Ala Ala Ile Leu
145                 150                 155                 160

Tyr Thr Ser Gly Thr Thr Gly Arg Ser Lys Gly Ala Met Leu Thr His
                165                 170                 175

Gly Asn Leu Leu Ser Asn Ala Leu Thr Leu Arg Asp Phe Trp Arg Val
            180                 185                 190

Thr Ala Gly Asp Arg Leu Ile His Ala Leu Pro Ile Phe His Thr His
        195                 200                 205

Gly Leu Phe Val Ala Thr Asn Val Thr Leu Leu Ala Gly Ala Ser Met
210                 215                 220

Phe Leu Leu Ser Lys Phe Asp Pro Glu Glu Ile Leu Ser Leu Met Pro
225                 230                 235                 240

Gln Ala Thr Met Leu Met Gly Val Pro Thr Phe Tyr Val Arg Leu Leu
                245                 250                 255

Gln Ser Pro Arg Leu Asp Lys Gln Ala Val Ala Asn Ile Arg Leu Phe
            260                 265                 270

Ile Ser Gly Ser Ala Pro Leu Leu Ala Glu Thr His Thr Glu Phe Gln
        275                 280                 285

Ala Arg Thr Gly His Ala Ile Leu Glu Arg Tyr Gly Met Thr Glu Thr
290                 295                 300

Asn Met Asn Thr Ser Asn Pro Tyr Glu Gly Lys Arg Ile Ala Gly Thr
305                 310                 315                 320

Val Gly Phe Pro Leu Pro Asp Val Thr Val Arg Val Thr Asp Pro Ala
                325                 330                 335

Thr Gly Leu Ala Leu Pro Pro Glu Gln Thr Gly Met Ile Glu Ile Lys
            340                 345                 350

Gly Pro Asn Val Phe Lys Gly Tyr Trp Arg Met Pro Glu Lys Thr Ala
        355                 360                 365

Ala Glu Phe Thr Ala Asp Gly Phe Phe Ile Ser Gly Asp Leu Gly Lys
370                 375                 380

Ile Asp Arg Asp Gly Tyr Val His Ile Val Gly Arg Gly Lys Asp Leu
385                 390                 395                 400

Val Ile Ser Gly Gly Tyr Asn Ile Tyr Pro Lys Glu Val Glu Gly Glu
                405                 410                 415

Ile Asp Gln Ile Glu Gly Val Val Glu Ser Ala Val Ile Gly Val Pro
            420                 425                 430

His Pro Asp Phe Gly Glu Gly Val Thr Ala Val Val Arg Lys Pro
        435                 440                 445

Gly Ala Ala Leu Asp Glu Lys Ala Ile Val Ser Ala Leu Gln Asp Arg
450                 455                 460

Leu Ala Arg Tyr Lys Gln Pro Lys Arg Ile Ile Phe Ala Glu Asp Leu
465                 470                 475                 480

Pro Arg Asn Thr Met Gly Lys Val Gln Lys Asn Ile Leu Arg Gln Gln
                485                 490                 495

Tyr Ala Asp Leu Tyr Thr Arg Thr
            500

<210> SEQ ID NO 6
<211> LENGTH: 4238
<212> TYPE: DNA
<213> ORGANISM: Artificial Sequence
<220> FEATURE:

<223> OTHER INFORMATION: Plasmid pMCS

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgagctcggt acctcgcgaa      420
tgcatctaga tccatggtct ccaaccacct gttcgacgcc atgcgagctg ccgctcccgg      480
agacgcacct ttcattcgaa tcgacaacgc tcggacctgg acttacgatg acgccattgc      540
tctttccggt cgaatcgctg gagctatgga cgcactcggc attcgacccg gagacagagt      600
tgccgtgcag gtcgagaagt ctgccgaggc gttgattctc tacctggcct gtcttcgaac      660
cggagctgtc tacctgcctc tcaacactgc ctacaccctg gccgagctcg actacttcat      720
cggcgatgcc gaaccgcgtc tggtggtcgt tgctcccgca gtcgaggtg gcgtggagac      780
aattgccaag cgacacggtg ctatcgtcga aaccctcgac gccgatggac gaggctcctt      840
gctggacctt gctagagatg agcctgccga ctttgtcgat gcttcgcgat ctgccgacga      900
tctggctgct attctctaca cttccggtac aaccggacga tcgaagggtg ccatgcttac      960
tcatggcaat ctgctctcca acgctctcac cttgcgagac tattggagag ttaccgcaga     1020
cgatcgactc atccatgcct tgccaatctt tcacactcat ggtctgttcg ttgctacgaa     1080
cgtcacactg cttgcaggag cctcgatgtt tctgctctcc aagttcgatg ccgacgaggt     1140
cgtttctctc atgccacagg ccaccatgct tatgggcgtg cccacattct acgttcgatt     1200
gctgcagagt cctcgactcg agaagggtgc tgtggccagc atcagactgt tcatttctgg     1260
atcagctccc ttgcttgccg aaacccacgc cgagtttcat gctcgtactg gtcacgccat     1320
tctcgagcga tacggcatga cggaaaccaa catgaatact tccaaccect acgagggcaa     1380
gcgtattgcc ggaaccgttg gtttcctct gcccgacgtc actgtgcgag tcaccgatcc     1440
cgccaccggt ctcgttcttc cacctgaaga gactggcatg atcgagatca agggacccaa     1500
cgtcttcaag ggctattggc gaatgcccga aaagaccgct gccgagttta ccgcagacgg     1560
tttctttatc tctggagatc tcggcaagat cgaccgagaa ggttacgttc acattgtggg     1620
acgaggcaag gacctggtca tttccggtgg ctacaacatc tatcccaaag aggtcgaagg     1680
cgagatcgac cagatcgagg gtgtggtcga gtctgctgtc attggtgttc ctcatcccga     1740
tttcggagaa ggtgtcaccg ctgttgtcgt gtgcaaacct ggtgccgttc tcgacgaaaa     1800
gaccatcgtg tctgctctgc aggaccgtct tgcccgatac aagcaaccca agcggattat     1860
ctttgccgac gatctgcctc gaaacactat gggaaaggtt cagaagaaca ttcttcgaca     1920
gcaatacgcc gatctctaca ccagacgata agcggccgca tcggatcccg ggcccgtcga     1980
ctgcagaggc ctgcatgcaa gcttggcgta atcatggtca tagctgtttc ctgtgtgaaa     2040
ttgttatccg ctcacaattc cacacaacat acgagccgga agcataaagt gtaaagcctg     2100
gggtgcctaa tgagtgagct aactcacatt aattgcgttg cgctcactgc ccgctttcca     2160
gtcgggaaac ctgtcgtgcc agctgcatta atgaatcggc caacgcgcgg ggagaggcgg     2220
tttgcgtatt gggcgctctt ccgcttcctc gctcactgac tcgctgcgct cggtcgttcg     2280
```

```
gctgcggcga gcggtatcag ctcactcaaa ggcggtaata cggttatcca cagaatcagg    2340
ggataacgca ggaaagaaca tgtgagcaaa aggccagcaa aaggccagga accgtaaaaa    2400
ggccgcgttg ctggcgtttt tccataggct ccgcccccct gacgagcatc acaaaaatcg    2460
acgctcaagt cagaggtggc gaaacccgac aggactataa agataccagg cgtttccccc    2520
tggaagctcc ctcgtgcgct ctcctgttcc gaccctgccg cttaccggat acctgtccgc    2580
ctttctccct tcgggaagcg tggcgctttc tcatagctca cgctgtaggt atctcagttc    2640
ggtgtaggtc gttcgctcca agctgggctg tgtgcacgaa ccccccgttc agcccgaccg    2700
ctgcgcctta tccggtaact atcgtcttga gtccaacccg gtaagacacg acttatcgcc    2760
actggcagca gccactggta acaggattag cagagcgagg tatgtaggcg gtgctacaga    2820
gttcttgaag tggtggccta actacggcta cactagaaga acagtatttg gtatctgcgc    2880
tctgctgaag ccagttacct tcggaaaaag agttggtagc tcttgatccg gcaaacaaac    2940
caccgctggt agcggtggtt tttttgtttg caagcagcag attacgcgca gaaaaaaagg    3000
atctcaagaa gatcctttga tcttttctac ggggtctgac gctcagtgga acgaaaactc    3060
acgttaaggg attttggtca tgagattatc aaaaaggatc ttcacctaga tccttttaaa    3120
ttaaaaatga agttttaaat caatctaaag tatatatgag taaacttggt ctgacagtta    3180
ccaatgctta atcagtgagg cacctatctc agcgatctgt ctatttcgtt catccatagt    3240
tgcctgactc cccgtcgtgt agataactac gatacgggag ggcttaccat ctggccccag    3300
tgctgcaatg ataccgcgag acccacgctc accggctcca gatttatcag caataaacca    3360
gccagccgga agggccgagc gcagaagtgg tcctgcaact ttatccgcct ccatccagtc    3420
tattaattgt tgccgggaag ctagagtaag tagttcgcca gttaatagtt tgcgcaacgt    3480
tgttgccatt gctacaggca tcgtggtgtc acgctcgtcg tttggtatgg cttcattcag    3540
ctccggttcc caacgatcaa ggcgagttac atgatccccc atgttgtgca aaaaagcggt    3600
tagctccttc ggtcctccga tcgttgtcag aagtaagttg gccgcagtgt tatcactcat    3660
ggttatggca gcactgcata attctcttac tgtcatgcca tccgtaagat gcttttctgt    3720
gactggtgag tactcaacca agtcattctg agaatagtgt atgcggcgac cgagttgctc    3780
ttgcccggcg tcaatacggg ataataccgc gccacatagc agaactttaa aagtgctcat    3840
cattggaaaa cgttcttcgg ggcgaaaact ctcaaggatc ttaccgctgt tgagatccag    3900
ttcgatgtaa cccactcgtg cacccaactg atcttcagca tcttttactt tcaccagcgt    3960
ttctgggtga gcaaaaacag gaaggcaaaa tgccgcaaaa aagggaataa gggcgacacg    4020
gaaatgttga atactcatac tcttcctttt tcaatattat tgaagcattt atcagggtta    4080
ttgtctcatg agcggataca tatttgaatg tatttagaaa aataaacaaa taggggttcc    4140
gcgcacattt ccccgaaaag tgccacctga cgtctaagaa accattatta tcatgacatt    4200
aacctataaa aataggcgta tcacgaggcc ctttcgtc                            4238

<210> SEQ ID NO 7
<211> LENGTH: 9156
<212> TYPE: DNA
<213> ORGANISM: Artificial Sequence
<220> FEATURE:
<223> OTHER INFORMATION: Plasmid pZP2-MCS

<400> SEQUENCE: 7
ggccgcaagt gtggatgggg aagtgagtgc ccggttctgt gtgcacaatt ggcaatccaa    60
```

| | |
|---|---|
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc gggcaacggt ttcacttgag tgcagtggct | 240 |
| agtgctctta ctcgtacagt gtgcaatact gcgtatcata gtctttgatg tatatcgtat | 300 |
| tcattcatgt tagttgcgta cgggcgtcgt tgcttgtgtg atttttgagg acccatccct | 360 |
| ttggtatata agtatactct ggggttaagg ttgcccgtgt agtctaggtt atagttttca | 420 |
| tgtgaaatac cgagagccga gggagaataa acggggtat ttggacttgt tttttcgcg | 480 |
| gaaaagcgtc gaatcaaccc tgcgggcctt gcaccatgtc cacgacgtgt ttctcgcccc | 540 |
| aattcgcccc ttgcacgtca aaattaggcc tccatctaga cccctccata acatgtgact | 600 |
| gtggggaaaa gtataaggga aaccatgcaa ccatagacga cgtgaaagac ggggaggaac | 660 |
| caatggaggc caaagaaatg gggtagcaac agtccaggag acagacaagg agacaaggag | 720 |
| agggcgcccg aaagatcgga aaacaaaca tgtccaattg gggcagtgac ggaaacgaca | 780 |
| cggacacttc agtacaatgg accgaccatc tccaagccag ggttattccg gtatcacctt | 840 |
| ggccgtaacc tcccgctggt acctgatatt gtacacgttc acattcaata tactttcagc | 900 |
| tacaataaga gaggctgttt gtcgggcatg tgtgtccgtc gtatgggggtg atgtccgagg | 960 |
| gcgaaattcg ctacaagctt aactctggcg cttgtccagt atgaatagac aagtcaagac | 1020 |
| cagtggtgcc atgattgaca gggaggtaca agacttcgat actcgagcat tactcggact | 1080 |
| tgtggcgatt gaacagacgg gcgatcgctt ctccccgta ttgccggcgc gccagctgca | 1140 |
| ttaatgaatc ggccaacgcg cggggagagg cggtttgcgt attgggcgct cttccgcttc | 1200 |
| ctcgctcact gactcgctgc gctcggtcgt tcggctgcgg cgagcggtat cagctcactc | 1260 |
| aaaggcggta atacggttat ccacagaatc aggggataac gcaggaaaga acatgtgagc | 1320 |
| aaaaggccag caaaaggcca ggaaccgtaa aaaggccgcg ttgctggcgt ttttccatag | 1380 |
| gctccgcccc cctgacgagc atcacaaaaa tcgacgctca agtcagaggt ggcgaaaccc | 1440 |
| gacaggacta taaagatacc aggcgtttcc ccctggaagc tccctcgtgc gctctcctgt | 1500 |
| tccgaccctg ccgcttaccg gatacctgtc cgcctttctc ccttcgggaa gcgtggcgct | 1560 |
| ttctcatagc tcacgctgta ggtatctcag ttcggtgtag gtcgttcgct ccaagctggg | 1620 |
| ctgtgtgcac gaaccccccg ttcagcccga ccgctgcgcc ttatccggta actatcgtct | 1680 |
| tgagtccaac ccggtaagac acgacttatc gccactggca gcagccactg gtaacaggat | 1740 |
| tagcagagcg aggtatgtag gcggtgctac agagttcttg aagtggtggc ctaactacgg | 1800 |
| ctacactaga agaacagtat ttggtatctg cgctctgctg aagccagtta ccttcggaaa | 1860 |
| aagagttggt agctcttgat ccggcaaaca accaccgct ggtagcggtg ttttttttgt | 1920 |
| ttgcaagcag cagattacgc gcagaaaaaa aggatctcaa gaagatcctt tgatcttttc | 1980 |
| tacggggtct gacgctcagt ggaacgaaaa ctcacgttaa gggattttgg tcatgagatt | 2040 |
| atcaaaaagg atcttcacct agatcctttt aaattaaaaa tgaagtttta aatcaatcta | 2100 |
| aagtatatat gagtaaactt ggtctgacag ttaccaatgc ttaatcagtg aggcacctat | 2160 |
| ctcagcgatc tgtctatttc gttcatccat agttgcctga ctccccgtcg tgtagataac | 2220 |
| tacgatacgg gagggcttac catctggccc cagtgctgca atgataccgc gagacccacg | 2280 |
| ctcaccggct ccagatttat cagcaataaa ccagccagcc ggaagggccg agcgcagaag | 2340 |
| tggtcctgca actttatccg cctccatcca gtctattaat tgttgccggg aagctagagt | 2400 |
| aagtagttcg ccagttaata gtttgcgcaa cgttgttgcc attgctacag gcatcgtggt | 2460 |

```
gtcacgctcg tcgtttggta tggcttcatt cagctccggt tcccaacgat caaggcgagt   2520
tacatgatcc cccatgttgt gcaaaaaagc ggttagctcc ttcggtcctc cgatcgttgt   2580
cagaagtaag ttggccgcag tgttatcact catggttatg gcagcactgc ataattctct   2640
tactgtcatg ccatccgtaa gatgcttttc tgtgactggt gagtactcaa ccaagtcatt   2700
ctgagaatag tgtatgcggc gaccgagttg ctcttgcccg gcgtcaatac gggataatac   2760
cgcgccacat agcagaactt taaaagtgct catcattgga aaacgttctt cggggcgaaa   2820
actctcaagg atcttaccgc tgttgagatc cagttcgatg taacccactc gtgcacccaa   2880
ctgatcttca gcatctttta ctttcaccag cgtttctggg tgagcaaaaa caggaaggca   2940
aaatgccgca aaaagggaa tagggcgac acggaaatgt tgaatactca tactcttcct   3000
ttttcaatat tattgaagca tttatcaggg ttattgtctc atgagcggat acatatttga   3060
atgtatttag aaaaataaac aaataggggt tccgcgcaca tttccccgaa aagtgccacc   3120
tgatgcggtg tgaaataccg cacagatgcg taaggagaaa ataccgcatc aggaaattgt   3180
aagcgttaat attttgttaa aattcgcgtt aaattttttgt taaatcagct catttttttaa   3240 ccaataggcc gaaatcggca aaatcccctta taaatcaaaa gaatagaccg agataggggtt   3300 gagtgttgtt ccagtttgga acaagagtcc actattaaag aacgtggact ccaacgtcaa   3360
agggcgaaaa accgtctatc agggcgatgg cccactacgt gaaccatcac cctaatcaag   3420 ttttttggg tcgaggtgcc gtaaagcact aaatcggaac cctaaaggga gccccgcatt   3480
tagagcttga cggggaaagc cggcgaacgt ggcgagaaag gaagggaaga aagcgaaagg   3540
agcgggcgct agggcgctgg caagtgtagc ggtcacgctg cgcgtaacca ccacacccgc   3600
cgcgcttaat gcgccgctac agggcgcgtc cattcgccat tcaggctgcg caactgttgg   3660
gaagggcgat cggtgcgggc ctcttcgcta ttacgccagc tggcgaaagg gggatgtgct   3720
gcaaggcgat taagttgggt aacgccaggg ttttcccagt cacgacgttg taaaacgacg   3780
gccagtgaat tgtaatacga ctcactatag ggcgaattgg gcccgacgtc gcatgcgctg   3840
atgacacttt ggtctgaaag agatgcattt tgaatcccaa acttgcagtg cccaagtgac   3900
atacatctcc gcgttttgga aaatgttcag aaacagttga ttgtgttgga atggggaatg   3960
gggaatggaa aaatgactca agtatcaatt ccaaaaactt ctctggctgg cagtacctac   4020
tgtccatact actgcatttt ctccagtcag gccactctat actcgacgac acagtagtaa   4080
aacccagata atttcgacat aaacaagaaa acagacccaa taatatttat atatagtcag   4140
ccgtttgtcc agttcagact gtaatagccg aaaaaaaatc caaagtttct attctaggaa   4200
aatatattcc aatatttta attcttaatc tcatttattt tattctagcg aaatacattt   4260
cagctacttg agacatgtga tacccacaaa tcggattcgg actcggttgt tcagaagagc   4320
atatggcatt cgtgctcgct tgttcacgta ttcttcctgt tccatctctt ggccgacaat   4380
cacacaaaaa tgggggtttt ttttttaattc taatgattca ttacagcaaa attgagatat   4440
agcagaccac gtattccata atcaccaagg aagttcttgg gcgtcttaat taagtcatac   4500
acaagtcagc tttcttcgag cctcatataa gtataagtag ttcaacgtat tagcactgta   4560
cccagcatct ccgtatcgag aaacacaaca acatgcccca ttggacagat catgcggata   4620
cacaggttgt gcagtatcat acatactcga tcagacaggt cgtctgacca tcatacaagc   4680
tgaacaagcg ctccatactt gcacgctctc tatatacaca gttaaattac atatccatag   4740
tctaacctct aacagttaat cttctggtaa gcctcccagc cagccttctg gtatcgcttg   4800
```

```
gcctcctcaa taggatctcg gttctggccg tacagacctc ggccgacaat tatgatatcc    4860
gttccggtag acatgacatc ctcaacagtt cggtactgct gtccgagagc gtctcccttg    4920
tcgtcaagac ccaccccggg ggtcagaata agccagtcct cagagtcgcc cttaggtcgg    4980
ttctgggcaa tgaagccaac cacaaactcg gggtcggatc gggcaagctc aatggtctgc    5040
ttggagtact cgccagtggc cagagagccc ttgcaagaca gctcggccag catgagcaga    5100
cctctggcca gcttctcgtt gggagagggg actaggaact ccttgtactg ggagttctcg    5160
tagtcagaga cgtcctcctt cttctgttca gagacagttt cctcggcacc agctcgcagg    5220
ccagcaatga ttccggttcc gggtacaccg tgggcgttgg tgatatcgga ccactcggcg    5280
attcggtgac accggtactg gtgcttgaca gtgttgccaa tatctgcgaa ctttctgtcc    5340
tcgaacagga agaaaccgtg cttaagagca agttccttga gggggagcac agtgccggcg    5400
taggtgaagt cgtcaatgat gtcgatatgg gtttttgatca tgcacacata aggtccgacc    5460
ttatcggcaa gctcaatgag ctccttggtg gtggtaacat ccagagaagc acacaggttg    5520
gttttcttgg ctgccacgag cttgagcact cgagcggcaa aggcggactt gtggacgtta    5580
gctcgagctt cgtaggaggg cattttggtg gtgaagagga gactgaaata aatttagtct    5640
gcagaacttt ttatcggaac cttatctggg gcagtgaagt atatgttatg gtaatagtta    5700
cgagttagtt gaacttatag atagactgga ctatacggct atcggtccaa attagaaaga    5760
acgtcaatgg ctctctgggc gtcgcctttg ccgacaaaaa tgtgatcatg atgaaagcca    5820
gcaatgacgt tgcagctgat attgttgtcg gccaaccgcg ccgaaaacgc agctgtcaga    5880
cccacagcct ccaacgaaga atgtatcgtc aaagtgatcc aagcacactc atagttggag    5940
tcgtactcca aaggcggcaa tgacgagtca gacagatact cgtcaaacgg taggttagtg    6000
cttggtatat gagttgtagg catgacaatt tggaaagggg tggactttgg gaatattgtg    6060
ggatttcaat accttagttt gtacagggta attgttacaa atgatacaaa gaactgtatt    6120
tcttttcatt tgttttaatt ggttgtatat caagtccgtt agacgagctc agtgccttgg    6180
cttttggcac tgtatttcat ttttagaggt acactacatt cagtgaggta tggtaaggtt    6240
gagggcataa tgaaggcacc ttgtactgac agtcacagac ctctcaccga gaattttatg    6300
agatatactc gggttcattt taggctcatc gatgagccta aaatgaaccc gagtatatct    6360
cataaaattc tcggtgagag gtctgtgact gtcagtacaa ggtgccttca ttatgccctc    6420
aaccttacca tacctcactg aatgtagtgt acctctaaaa atgaaataca gtgccaaaag    6480
ccaaggcact gagctcgtct aacggacttg atatacaacc aattaaaaca atgaaaaga     6540 aatacagttc tttgtatcat ttgtaacaat taccctgtac aaactaaggt attgaaatcc    6600
cacaatattc ccaaagtcca ccccttcca aattgtcatg cctacaactc atataccaag     6660
cactaaccta ccgtttaaac agtgtacgca gatctactat agaggaacat ttaaattgcc    6720
ccggagaaga cggccaggcc gcctagatga caaattcaac aactcacagc tgactttctg    6780
ccattgccac taggggggg cctttttata tggccaagcc aagctctcca cgtcggttgg     6840
gctgcaccca acaataaatg ggtagggttg caccaacaaa gggatgggat gggggtaga    6900 agatacgagg ataacgggc tcaatggcac aaataagaac gaatactgcc attaagactc    6960
gtgatccagc gactgacacc attgcatcat ctaagggcct caaaactacc tcggaactgc    7020
tgcgctgatc tggacaccac agaggttccg agcactttag gttgcaccaa atgtcccacc    7080
aggtgcaggc agaaaacgct ggaacagcgt gtacagtttg tcttaacaaa aagtgagggc    7140
gctgaggtcg agcagggtgg tgtgacttgt tatagccttt agagctgcga aagcgcgtat    7200
```

-continued

```
ggatttggct catcaggcca gattgagggt ctgtggacac atgtcatgtt agtgtacttc    7260
aatcgccccc tggatatagc cccgacaata ggccgtggcc tcattttttt gccttccgca    7320
catttccatt gctcggtacc cacaccttgc ttctcctgca cttgccaacc ttaatactgg    7380
tttacattga ccaacatctt acaagcgggg ggcttgtcta gggtatatat aaacagtggc    7440
tctcccaatc ggttgccagt ctcttttttc ctttctttcc ccacagattc gaaatctaaa    7500
ctacacatca cagaattccg agccgtgagt atccacgaca agatcagtgt cgagacgacg    7560
cgttttgtgt aatgacacaa tccgaaagtc gctagcaaca cacactctct acacaaacta    7620
acccagctct ggtaccatgg tctccaacca cctgttcgac gccatgcgag ctgccgctcc    7680
cggagacgca cctttcattc gaatcgacaa cgctcggacc tggacttacg atgacgccat    7740 tgctcttttcc ggtcgaatcg ctggagctat ggacgcactc ggcattcgac ccggagacag    7800
agttgccgtg caggtcgaga agtctgccga ggcgttgatt ctctacctgg cctgtcttcg    7860
aaccggagct gtctacctgc ctctcaacac tgcctacacc ctggccgagc tcgactactt    7920
catcggcgat gccgaaccgc gtctggtggt cgttgctccc gcagctcgag gtggcgtgga    7980
gacaattgcc aagcgacacg tgctatcgt cgaaaccctc gacgccgatg gacgaggctc    8040
cttgctggac cttgctagag atgagcctgc cgactttgtc gatgcttcgc gatctgccga    8100
cgatctggct gctattctct acacttccgg tacaaccgga cgatcgaagg gtgccatgct    8160
tactcatggc aatctgctct ccaacgctct caccttgcga gactattgga gagttaccgc    8220
agacgatcga ctcatccatg ccttgccaat ctttcacact catggtctgt tcgttgctac    8280
gaacgtcaca ctgcttgcag gagcctcgat gtttctgctc tccaagttcg atgccgacga    8340
ggtcgtttct ctcatgccac aggccaccat gcttatgggc gtgcccacat tctacgttcg    8400
attgctgcag agtcctcgac tcgagaaggg tgctgtggcc agcatcagac tgttcatttc    8460
tggatcagct cccttgcttg ccgaaaccca cgccgagttt catgtctgta ctggtcacgc    8520
cattctcgag cgatacggca tgacggaaac caacatgaat acttccaacc cctacgaggg    8580
caagcgtatt gccggaaccg ttggttttcc tctgcccgac gtcactgtgc gagtcaccga    8640
tcccgccacc ggtctcgttc ttccacctga agagactggc atgatcgaga tcaagggacc    8700
caacgtcttc aagggctatt ggcgaatgcc cgaaaagacc gctgccgagt ttaccgcaga    8760
cggtttcttt atctctggag atctcggcaa gatcgaccga gaaggttacg ttcacattgt    8820
gggacgaggc aaggacctgg tcatttccgg tggctacaac atctatccca agaggtcga    8880 aggcgagatc gaccagatcg agggtgtggt cgagtctgct gtcattggtg ttcctcatcc    8940
cgatttcgga gaaggtgtca ccgctgttgt cgtgtgcaaa cctggtgccg ttctcgacga    9000
aaagaccatc gtgtctgctc tgcaggaccg tcttgcccga tacaagcaac ccaagcggat    9060
tatctttgcc gacgatctgc ctcgaaacac tatgggaaag gttcagaaga acattcttcg    9120
acagcaatac gccgatctct acaccagacg ataagc                              9156
```

<210> SEQ ID NO 8
<211> LENGTH: 496
<212> TYPE: PRT
<213> ORGANISM: Rhizobium etli CFN 42
<220> FEATURE:
<221> NAME/KEY: MISC_FEATURE
<222> LOCATION: (1)..(496)
<223> OTHER INFORMATION: GenBank Accession No. YP_468459

<400> SEQUENCE: 8

```
Met Arg Ala Ala Ala Pro Asp Asn Ala Gln Phe Ile Arg Thr Gly Ser
1               5                   10                  15

Gly Gln Thr Trp Thr Tyr Gly Asp Ala Phe Ala Leu Ser Gly Arg Ile
            20                  25                  30

Ala Gly Ala Met Asp Thr Leu Gly Ile Arg Pro Gly Asp Arg Val Ala
        35                  40                  45

Val Gln Val Asp Lys Ser Ala Glu Ala Leu Ile Leu Tyr Leu Ala Cys
    50                  55                  60

Val Arg Ser Gly Ala Val Tyr Leu Pro Leu Asn Thr Ala Tyr Thr Leu
65                  70                  75                  80

Ala Glu Leu Asp Tyr Phe Leu Gly Asp Ala Glu Pro Arg Leu Val Val
                85                  90                  95

Val Ala Ser Gly Ala Arg Glu Gly Val Glu Thr Ile Ala Lys Arg His
        100                 105                 110

Gly Ala Ile Val Glu Thr Leu Asp Ala Asp Gly Ser Gly Ser Leu Leu
        115                 120                 125

Asp Leu Ala Arg Asp Glu Pro Ala Asp Phe Val Asp Ala Ser Arg Ala
    130                 135                 140

Ala Asp Asp Leu Ala Ala Ile Leu Tyr Thr Ser Gly Thr Thr Gly Arg
145                 150                 155                 160

Ser Lys Gly Ala Met Leu Thr His Gly Asn Leu Leu Ser Asn Ala Leu
                165                 170                 175

Thr Leu Arg Asp Tyr Trp Arg Val Thr Ala Asp Arg Leu Ile His
            180                 185                 190

Ala Leu Pro Ile Phe His Thr His Gly Leu Phe Val Ala Thr Asn Val
        195                 200                 205

Thr Leu Leu Ala Gly Ala Ser Met Phe Leu Leu Ser Lys Phe Asp Ala
    210                 215                 220

Asp Glu Val Ile Ser Leu Met Pro Gln Ala Thr Met Leu Met Gly Val
225                 230                 235                 240

Pro Thr Phe Tyr Val Arg Leu Leu Gln Ser Pro Arg Phe Gly Lys Glu
                245                 250                 255

Ala Ala Ala Lys Ile Arg Leu Phe Ile Ser Gly Ser Ala Pro Leu Leu
            260                 265                 270

Ala Glu Thr His Thr Glu Phe Gln Ala Arg Thr Gly His Ala Ile Leu
        275                 280                 285

Glu Arg Tyr Gly Met Thr Glu Thr Asn Met Asn Thr Ser Asn Pro Tyr
    290                 295                 300

Asp Gly Lys Arg Ile Ala Gly Thr Val Gly Leu Pro Leu Pro Gly Val
305                 310                 315                 320

Thr Val Arg Val Thr Asp Pro Ala Thr Gly Gln Val Leu Pro Pro Glu
                325                 330                 335

Gln Thr Gly Met Ile Glu Ile Lys Gly Pro Asn Val Phe Lys Gly Tyr
            340                 345                 350

Trp Arg Met Pro Glu Lys Thr Ala Ala Glu Phe Thr Gly Asp Gly Phe
        355                 360                 365

Phe Ile Ser Gly Asp Leu Gly Lys Ile Asp Ser Asp Gly Tyr Val His
    370                 375                 380

Ile Val Gly Arg Gly Lys Asp Leu Val Ile Ser Gly Gly Tyr Asn Ile
385                 390                 395                 400

Tyr Pro Lys Glu Val Glu Ser Glu Ile Asp Gln Ile Glu Gly Val Val
                405                 410                 415

Glu Ser Ala Val Ile Gly Val Pro His Pro Asp Phe Gly Glu Gly Val
```

```
                420                 425                 430
Thr Ala Val Val Arg Lys Pro Gly Ala Ala Leu Asp Glu Lys Thr
            435                 440                 445
Ile Ile Ser Ala Leu Gln Asp Arg Leu Ala Arg Tyr Lys Gln Pro Lys
        450                 455                 460
Arg Ile Ile Phe Ala Glu Asp Leu Pro Arg Asn Thr Met Gly Lys Val
465                 470                 475                 480
Gln Lys Asn Ile Leu Arg Gln Gln Tyr Ala Asp Leu Tyr Thr Gly Thr
            485                 490                 495
```

<210> SEQ ID NO 9
<211> LENGTH: 510
<212> TYPE: PRT
<213> ORGANISM: Sinorhizobium medicae WSM419
<220> FEATURE:
<221> NAME/KEY: MISC_FEATURE
<222> LOCATION: (1)..(510)
<223> OTHER INFORMATION: GenBank Accession No. YP_001313848

<400> SEQUENCE: 9

```
Met Ser Asn His Leu Phe Asp Ala Ile Arg Arg Ala Ser Arg Pro Asp
1               5                   10                  15
Ser Val Phe Ile Leu Ala Ala Asp Glu Arg Val Trp Thr Tyr Gly Asp
                20                  25                  30
Met Leu Glu His Ser Gly Arg Leu Ala Ser Ala Leu Val Ser Leu Gly
            35                  40                  45
Val Gln Pro Gly Asp Arg Val Ala Val Gln Val Glu Lys Ser Pro Glu
        50                  55                  60
Ala Leu Met Leu Tyr Leu Ala Cys Leu Arg Ala Gly Ala Val Tyr Leu
65                  70                  75                  80
Pro Leu Asn Thr Ala Tyr Thr Leu Thr Glu Leu Asp Tyr Phe Phe Gly
                85                  90                  95
Asp Ala Glu Pro Arg Leu Ile Val Cys Ala Pro Ala Ala Lys Glu Gly
            100                 105                 110
Ile Ser Lys Ile Ala Ala Tyr Arg Ser Ala Gly Val Glu Thr Leu Asp
        115                 120                 125
Asp Lys Gly Gly Gly Ser Leu Ile Glu Leu Ala Leu Gly Glu Thr Pro
130                 135                 140
Asp Phe Ser Asp Leu Asp Arg Arg Ala Asp Leu Ala Ala Ile Leu
145                 150                 155             160
Tyr Thr Ser Gly Thr Thr Gly Arg Ser Lys Gly Ala Met Leu Thr His
                165                 170                 175
Asp Asn Leu Leu Ser Asn Ala Val Thr Leu Arg Asp His Trp Arg Phe
            180                 185                 190
Thr Ala Asp Asp Arg Leu Ile His Ala Leu Pro Ile Phe His Thr His
        195                 200                 205
Gly Leu Phe Val Ala Ser Asn Val Ile Leu Ala Gly Ala Ser Met
210                 215                 220
Phe Phe Leu Pro Lys Phe Asp Ala Asn Glu Val Leu Ser Leu Met Pro
225                 230                 235                 240
Arg Ser Thr Thr Met Met Gly Val Pro Thr Phe Tyr Val Arg Leu Val
                245                 250                 255
Gln Asn Pro Gly Leu Thr Arg Glu Val Thr Ala Gly Met Arg Leu Phe
            260                 265                 270
Val Ser Gly Ser Ala Pro Leu Leu Ala Glu Thr His Arg Thr Phe Ala
        275                 280                 285
```

```
His Met Thr Gly His Ala Ile Leu Glu Arg Tyr Gly Met Thr Glu Thr
    290                 295                 300

Asn Met Asn Thr Ser Asn Pro Tyr Asp Gly Glu Arg Ile Ala Gly Thr
305                 310                 315                 320

Val Gly Phe Pro Leu Pro Gly Ile Ser Leu Arg Val Ala Asp Pro Glu
                325                 330                 335

Ser Gly Lys Pro Leu Pro Asn Gly Asp Thr Gly Met Ile Glu Val Lys
            340                 345                 350

Gly Pro Asn Val Phe Lys Gly Tyr Trp Arg Met Pro Glu Lys Thr Gln
        355                 360                 365

Ala Glu Phe Arg Ala Asp Gly Phe Phe Ile Thr Gly Asp Leu Gly Lys
370                 375                 380

Ile Asp Asp Arg Gly Tyr Val His Ile Val Gly Arg Gly Lys Asp Leu
385                 390                 395                 400

Val Ile Ser Gly Gly Tyr Asn Ile Tyr Pro Lys Glu Val Glu Thr Glu
                405                 410                 415

Ile Asp Gln Met Pro Gly Val Val Glu Thr Ala Val Ile Gly Val Pro
            420                 425                 430

His Pro Asp Phe Gly Glu Gly Val Thr Ala Val Val Arg Lys Pro
        435                 440                 445

Gly Ala Thr Ile Asp Glu Arg Ala Ile Leu Gly Gly Leu Glu Gly Arg
450                 455                 460

Leu Ala Arg Tyr Lys Gln Pro Lys Arg Val Ile Phe Val Glu Asp Leu
465                 470                 475                 480

Pro Arg Asn Thr Met Gly Lys Val Gln Lys Asn Val Leu Arg Glu Ala
                485                 490                 495

Tyr Ala Asp Leu Tyr Ala Glu Ala Gly Ala Gly Ala Arg Ile
            500                 505                 510

<210> SEQ ID NO 10
<211> LENGTH: 506
<212> TYPE: PRT
<213> ORGANISM: Mesorhizobium sp. BNC1
<220> FEATURE:
<221> NAME/KEY: MISC_FEATURE
<222> LOCATION: (1)..(506)
<223> OTHER INFORMATION: GenBank Accession No. YP_674146

<400> SEQUENCE: 10

Met Thr Asn His Met Phe Asp Ala Ile Ala Thr Ala Ala Asn Arg Arg
1               5                   10                  15

Glu Ala Pro Phe Ile Phe Thr Pro Ser Gly Arg Val Trp Thr Tyr Gly
            20                  25                  30

Asp Leu Leu Asp Phe Ser Ala Arg Met Ala Asn Arg Leu Val Thr Leu
        35                  40                  45

Gly Val Lys Pro Gly Asp Arg Val Ala Val Gln Val Glu Lys Ser Pro
    50                  55                  60

Glu Ala Leu Ile Leu Tyr Val Ala Cys Leu Arg Ala Gly Ala Val Tyr
65                  70                  75                  80

Leu Pro Leu Asn Ile Asp Tyr Thr Gln Ala Glu Leu Glu Tyr Phe Ile
                85                  90                  95

Gly Asp Ala Glu Pro Ala Leu Val Val Ala Thr Pro Ser Ala Gly Ala
            100                 105                 110

Gly Ile Ala Ser Leu Ala Arg Gln His Gly Gly Arg Val Glu Thr Leu
        115                 120                 125
```

Asp Glu Phe Gly Gly Ser Leu Val Ala Asp Leu Ala Ala Pro Ala
130                 135                 140

Asp Phe Ala Asp Ile Pro Arg Gly Pro Asp Leu Ala Ala Ile Leu
145                 150                 155                 160

Tyr Thr Ser Gly Thr Thr Gly Arg Ser Lys Gly Ala Met Leu Ser His
                165                 170                 175

Asp Asn Leu Leu Ser Asn Ala Lys Thr Leu Ile Ser His Trp Arg Phe
                180                 185                 190

Thr Ala Gly Asp Arg Leu Ile His Ala Leu Pro Ile Phe His Thr His
                195                 200                 205

Gly Leu Phe Val Ala Ser Asn Val Ile Met Leu Ser Gly Ala Ser Met
210                 215                 220

Asp Phe Leu Pro Lys Phe Asp Pro Lys Ala Val Leu Gly Leu Met Glu
225                 230                 235                 240

Thr Ala Thr Cys Leu Met Gly Val Pro Thr Phe Tyr Thr Arg Leu Leu
                245                 250                 255

Glu Ser Glu Ala Leu Ser Ala Glu Lys Thr Ala Asn Met Arg Leu Phe
                260                 265                 270

Ile Ser Gly Ser Ala Pro Leu Leu Ala Glu Thr His His Ala Phe Ala
                275                 280                 285

Glu Arg Thr Gly His Ala Ile Leu Glu Arg Tyr Gly Met Thr Glu Thr
290                 295                 300

Asn Met Asn Thr Ser Asn Pro Tyr Asp Gly Glu Arg Ile Ala Gly Thr
305                 310                 315                 320

Val Gly Phe Pro Leu Ser Gly Val Ser Ile Arg Ile Thr Asp Pro Glu
                325                 330                 335

Ser Gly Ala Val Leu Gly Thr Gly Glu Ile Gly Met Ile Glu Ile Lys
                340                 345                 350

Gly Pro Asn Val Phe Lys Gly Tyr Trp Arg Met Pro Glu Lys Thr Ala
                355                 360                 365

Ala Glu Phe Arg Ala Asp Gly Tyr Phe Ile Ser Gly Asp Leu Gly Lys
                370                 375                 380

Ile Asp Glu Arg Gly Tyr Ile His Ile Val Gly Arg Gly Lys Asp Leu
385                 390                 395                 400

Ile Ile Thr Gly Gly Tyr Asn Val Tyr Pro Lys Glu Val Glu Thr Glu
                405                 410                 415

Ile Asp Gln Ile Asp Gly Val Lys Glu Ser Ala Val Ile Gly Leu Pro
                420                 425                 430

His Pro Asp Phe Gly Glu Gly Val Thr Ala Val Val Arg Ser Pro
                435                 440                 445

Gly Ser Thr Ile Ser Ala Ser Asp Val Leu Ile Ala Leu Gln Gly Arg
450                 455                 460

Leu Ala Lys Tyr Lys Gln Pro Lys Thr Val His Phe Leu Pro Asp Leu
465                 470                 475                 480

Pro Arg Asn Thr Met Gly Lys Val Gln Lys Asn Val Leu Arg Glu Thr
                485                 490                 495

Phe Asn Asp Ile Tyr Lys Ala Pro Arg Ala
                500                 505

<210> SEQ ID NO 11
<211> LENGTH: 504
<212> TYPE: PRT
<213> ORGANISM: Mesorhizobium loti MAFF303099
<220> FEATURE:
<221> NAME/KEY: MISC_FEATURE
<222> LOCATION: (1)..(504)
<223> OTHER INFORMATION: GenBank Accession No. NP_105559

<400> SEQUENCE: 11

```
Met Ser Asn His Leu Phe Asp Ala Phe Arg Ser Arg Met Pro Ala Pro
1               5                   10                  15

Gly His Leu Leu Met Glu Thr Asp Gly Arg Ser Leu Ser Tyr Gly
            20                  25                  30

Asp Met Leu Ala Arg Ser Ala Gln Phe Ala His Ala Leu Leu Gln Leu
            35                  40                  45

Asp Val Glu Pro Gly Asp Arg Val Ala Val Gln Val Glu Lys Ser Pro
        50                  55                  60

Glu Ala Leu Leu Leu Tyr Leu Ala Cys Val Arg Ala Gly Ala Val Phe
65              70                  75                  80

Leu Pro Leu Asn Thr Ala Tyr Thr Leu Thr Glu Leu Gly Tyr Phe Phe
                85                  90                  95

Gly Asp Ala Ala Pro Arg Val Ile Val Cys Asp Pro Ala Arg Ala Ala
            100                 105                 110

Asp Ile Gly Arg Met Val Glu Pro Ser Gly Ala Val Val Thr Leu
            115                 120                 125

Asp Arg Asn Gly Arg Gly Ser Leu Ala Asp Gln Ala Ser Arg Leu Pro
    130                 135                 140

Ser Asp Phe His Asp Val Ala Arg Gly Pro Asp Leu Ala Ala Ile
145                 150                 155                 160

Leu Tyr Thr Ser Gly Thr Thr Gly Arg Ser Lys Gly Ala Met Leu Ser
                165                 170                 175

His Glu Asn Leu Ala Ser Asn Ala Arg Val Leu Val Glu Gln Trp Arg
            180                 185                 190

Phe Thr Ser Gly Asp Val Leu Ile His Ala Leu Pro Ile Phe His Thr
            195                 200                 205

His Gly Leu Phe Val Ala Thr Asn Val Val Leu Met Ala Gly Ala Ala
        210                 215                 220

Met Leu Phe Glu Gln Lys Phe Asp Pro Ala Arg Ile Val Ala Leu Leu
225                 230                 235                 240

Pro Arg Gly Thr Ala Leu Met Gly Val Pro Thr Phe Tyr Val Arg Leu
                245                 250                 255

Leu Gln Gln Asp Gly Leu Asp Arg Gln Ala Ala Lys Thr Ile Arg Leu
            260                 265                 270

Phe Val Ser Gly Ser Ala Pro Leu Leu Ala Asp Thr His Lys Ala Trp
            275                 280                 285

Arg Glu Arg Thr Gly His Ala Ile Leu Glu Arg Tyr Gly Met Thr Glu
    290                 295                 300

Thr Asn Met Asn Thr Ser Asn Pro Tyr Glu Gly Glu Arg Arg Ala Gly
305                 310                 315                 320

Thr Val Gly Phe Pro Leu Pro Gly Val Ala Leu Arg Ile Ala Asp Pro
                325                 330                 335

Asp Thr Gly Lys Pro Leu Ala Gln Gly Glu Val Gly Met Ile Glu Val
            340                 345                 350

Lys Gly Pro Asn Val Phe Gly Tyr Trp Arg Met Pro Glu Lys Thr
            355                 360                 365

Lys Ala Glu Phe Arg Ala Asp Gly Phe Phe Ile Thr Gly Asp Leu Gly
    370                 375                 380

Met Val Asp Thr Asp Gly Tyr Val His Ile Val Gly Arg Gly Lys Asp
385                 390                 395                 400
```

```
Leu Ile Ile Ser Gly Gly Tyr Asn Ile Tyr Pro Lys Glu Leu Glu Ser
                405                 410                 415

Glu Ile Asp Ala Leu Asp Gly Val Ser Glu Ser Ala Val Ile Gly Val
                420                 425                 430

Ala His Pro Asp Phe Gly Glu Gly Val Thr Ala Val Val Arg Ala
            435                 440                 445

Pro Gly Ala Ala Ile Thr Gly Ala Glu Val Leu Gly Ala Ile Ala Gly
            450                 455                 460

Arg Leu Ala Arg Tyr Lys His Pro Lys Gln Val Ile Phe Val Asp Glu
465                 470                 475                 480

Leu Pro Arg Asn Thr Met Gly Lys Val Gln Lys Asn Leu Leu Arg Asp
                485                 490                 495

Ala Tyr Lys Asp Leu Tyr Thr Ser
            500
```

<210> SEQ ID NO 12
<211> LENGTH: 508
<212> TYPE: PRT
<213> ORGANISM: Bradyrhizobium sp. BTAi1
<220> FEATURE:
<221> NAME/KEY: MISC_FEATURE
<222> LOCATION: (1)..(508)
<223> OTHER INFORMATION: GenBank Accession No. YP_001236428

<400> SEQUENCE: 12

```
Met Asn Gln Thr Ala Asn Ala Asn Leu Phe Ala Arg Leu Phe Asp Gly
1               5                   10                  15

Leu Asp Asp Pro Ser Arg Leu Ala Ile Glu Thr His Asp Gly Gln Arg
                20                  25                  30

Ile Thr Tyr Gly Asp Leu Ile Ala Arg Ala Gly Gln Met Ala Asn Val
            35                  40                  45

Leu Val Ser Arg Gly Val Lys Pro Gly Asp Arg Val Ala Ala Gln Thr
        50                  55                  60

Glu Lys Ser Val Ser Gly Leu Val Leu Tyr Leu Ala Thr Val Arg Ala
65                  70                  75                  80

Gly Gly Val Tyr Leu Pro Leu Asn Thr Ala Tyr Thr Leu Asn Glu Leu
                85                  90                  95

Asp Tyr Phe Ile Gly Asp Ala Glu Pro Thr Val Val Cys Asp Pro
                100                 105                 110

Ala Lys Ala Glu Gly Ile Arg Thr Leu Ala Ala Lys Val Gly Ala Thr
            115                 120                 125

Val Asp Thr Leu Asp Ala Ser Gly Lys Gly Ser Leu Thr Glu Ala Ala
        130                 135                 140

Asp Lys Ala Ala Thr Ala Phe Thr Thr Val Pro Arg Gly Ala Asp Asp
145                 150                 155                 160

Leu Ala Ala Ile Leu Tyr Thr Ser Gly Thr Thr Gly Arg Ser Lys Gly
                165                 170                 175

Ala Met Leu Ser His Asp Asn Leu Ala Ser Asn Ser Leu Thr Leu Ile
                180                 185                 190

Asp Tyr Trp Arg Phe Thr Lys Asp Asp Val Leu Ile His Ala Leu Pro
            195                 200                 205

Ile Tyr His Thr His Gly Leu Phe Val Ala Ser Asn Val Thr Leu Phe
        210                 215                 220

Ala Arg Ala Ser Met Ile Phe Leu Pro Lys Leu Asp Pro Asp Leu Ile
225                 230                 235                 240
```

Ile Asn Leu Met Ala Arg Ala Thr Val Leu Met Gly Val Pro Thr Phe
            245                 250                 255

Tyr Thr Arg Leu Leu Gln Asn Pro Arg Leu Asn Lys Glu Thr Thr Ser
        260                 265                 270

His Met Arg Leu Phe Ile Ser Gly Ser Ala Pro Leu Leu Ala Asp Thr
    275                 280                 285

His Arg Glu Trp Phe Ala Arg Thr Gly His Ala Val Leu Glu Arg Tyr
290                 295                 300

Gly Met Thr Glu Thr Asn Met Asn Thr Ser Asn Pro Tyr Asp Gly Glu
305                 310                 315                 320

Arg Val Pro Gly Ala Val Gly Phe Pro Leu Pro Gly Val Ser Val Arg
                325                 330                 335

Val Thr Asp Pro Glu Thr Gly Lys Glu Leu Ala Arg Asp Glu Ile Gly
            340                 345                 350

Met Ile Glu Val Lys Gly Pro Asn Val Phe Lys Gly Tyr Trp Arg Met
        355                 360                 365

Pro Glu Lys Thr Lys Ser Glu Phe Arg Pro Asp Gly Phe Phe Ile Thr
    370                 375                 380

Gly Asp Leu Gly Lys Ile Asp Thr Gln Gly Tyr Val His Ile Val Gly
385                 390                 395                 400

Arg Gly Lys Asp Leu Val Ile Ser Gly Gly Phe Asn Val Tyr Pro Lys
                405                 410                 415

Glu Ile Glu Ser Glu Ile Asp Ala Met Pro Gly Val Val Glu Ser Ala
            420                 425                 430

Val Ile Gly Val Pro His Ala Asp Phe Gly Glu Gly Val Thr Ala Val
        435                 440                 445

Val Val Arg His Pro Gly Ala Asp Val Asn Glu Ala Ser Val Leu Lys
    450                 455                 460

Gly Leu Asp Gly Arg Leu Ala Lys Phe Lys Met Pro Lys Arg Val Phe
465                 470                 475                 480

Val Val Asp Glu Leu Pro Arg Asn Thr Met Gly Lys Val Gln Lys Asn
                485                 490                 495

Val Leu Arg Asp Gln Tyr Lys Asp Ile Tyr Thr Lys
            500                 505

<210> SEQ ID NO 13
<211> LENGTH: 504
<212> TYPE: PRT
<213> ORGANISM: Rhodopseudomonas palustris BisA53
<220> FEATURE:
<221> NAME/KEY: MISC_FEATURE
<222> LOCATION: (1)..(504)
<223> OTHER INFORMATION: GenBank Accession No. YP_779412

<400> SEQUENCE: 13

Met Asn Ala Asn Leu Phe Ser Arg Leu Phe Asp Gly Leu Val Glu Ala
1               5                   10                  15

Asp Lys Leu Ala Ile Glu Thr Leu Glu Gly Glu Arg Ile Ser Tyr Gly
            20                  25                  30

Asp Leu Val Ala Arg Ser Gly Arg Met Ala Asn Val Leu Val Ala Arg
        35                  40                  45

Gly Val Lys Pro Gly Asp Arg Val Ala Ala Gln Ala Glu Lys Ser Val
    50                  55                  60

Ala Ala Leu Val Leu Tyr Leu Ala Thr Val Arg Ala Gly Ala Val Tyr
65                  70                  75                  80

Leu Pro Leu Asn Thr Ala Tyr Thr Leu His Glu Leu Asp Tyr Phe Ile

```
            85                  90                  95
Gly Asp Ala Glu Pro Lys Leu Val Val Cys Asp Pro Ala Lys Arg Glu
            100                 105                 110

Gly Ile Ala Ala Leu Ala Gln Lys Val Gly Ala Gly Val Glu Thr Leu
            115                 120                 125

Asp Ala Lys Gly Gln Gly Ser Leu Ser Glu Ala Ala Gln Ala Ser
            130                 135                 140

Val Asp Phe Ala Thr Val Pro Arg Glu Gly Asp Asp Leu Ala Ala Ile
145                 150                 155                 160

Leu Tyr Thr Ser Gly Thr Thr Gly Arg Ser Lys Gly Ala Met Leu Ser
                    165                 170                 175

His Asp Asn Leu Ala Ser Asn Ser Leu Thr Leu Val Glu Phe Trp Arg
                    180                 185                 190

Phe Thr Pro Asp Asp Val Leu Ile His Ala Leu Pro Ile Tyr His Thr
                    195                 200                 205

His Gly Leu Phe Val Ala Ser Asn Val Thr Leu Phe Ala Arg Ala Ser
            210                 215                 220

Met Ile Phe Leu Pro Lys Phe Asp Pro Asp Ala Ile Ile Gln Leu Met
225                 230                 235                 240

Ser Arg Ala Ser Val Leu Met Gly Val Pro Thr Phe Tyr Thr Arg Leu
                    245                 250                 255

Leu Gln Ser Asp Gly Leu Thr Lys Glu Ala Ala Arg His Met Arg Leu
                    260                 265                 270

Phe Ile Ser Gly Ser Ala Pro Leu Leu Ala Asp Thr His Arg Glu Trp
                    275                 280                 285

Ala Ser Arg Thr Gly His Ala Val Leu Glu Arg Tyr Gly Met Thr Glu
            290                 295                 300

Thr Asn Met Asn Thr Ser Asn Pro Tyr Asp Gly Ala Arg Val Pro Gly
305                 310                 315                 320

Ala Val Gly Pro Ala Leu Pro Gly Val Ser Leu Arg Val Val Asp Pro
                    325                 330                 335

Glu Thr Gly Ala Glu Leu Ser Pro Gly Glu Ile Gly Met Ile Glu Val
            340                 345                 350

Lys Gly Pro Asn Val Phe Gln Gly Tyr Trp Arg Met Pro Glu Lys Thr
            355                 360                 365

Lys Ala Glu Phe Arg Asp Asp Gly Phe Phe Ile Thr Gly Asp Leu Gly
            370                 375                 380

Lys Ile Asp Ala Asp Gly Tyr Val Phe Ile Val Gly Arg Gly Lys Asp
385                 390                 395                 400

Leu Val Ile Thr Gly Gly Phe Asn Val Tyr Pro Lys Glu Val Glu Ser
                    405                 410                 415

Glu Ile Asp Ala Ile Ser Gly Val Val Glu Ser Ala Val Ile Gly Val
            420                 425                 430

Pro His Ala Asp Leu Gly Glu Gly Val Thr Ala Val Val Arg Asp
            435                 440                 445

Lys Gly Ala Ser Val Asp Glu Ala Val Leu Gly Ala Leu Gln Gly
            450                 455                 460

Gln Leu Ala Lys Phe Lys Met Pro Lys Arg Val Leu Phe Val Asp Asp
465                 470                 475                 480

Leu Pro Arg Asn Thr Met Gly Lys Val Gln Lys Asn Val Leu Arg Glu
                    485                 490                 495

Ala Tyr Ala Lys Leu Tyr Ala Lys
            500
```

<210> SEQ ID NO 14
<211> LENGTH: 508
<212> TYPE: PRT
<213> ORGANISM: Azorhizobium caulinodans ORS 571
<220> FEATURE:
<221> NAME/KEY: MISC_FEATURE
<222> LOCATION: (1)..(508)
<223> OTHER INFORMATION: GenBank Accession No. YP_001526214

<400> SEQUENCE: 14

```
Met Thr Ser Gln Asn His Phe Phe Ala Ala Ile Arg Ala Ala Met Pro
1               5                   10                  15

Asp Leu Ser Lys Pro Leu Ala Thr His Pro Asp Gly Ala Met Glu Thr
            20                  25                  30

Tyr Gly Asp Ala Leu Ala Leu Ser Ala Arg Leu Ala Asn Val Leu Val
        35                  40                  45

Lys Arg Gly Val Lys Pro Gly Asp Arg Val Ala Val Gln Val Glu Lys
    50                  55                  60

Ser Trp Thr Ala Phe Val Leu Tyr Leu Ala Ala Leu Arg Ala Gly Ala
65                  70                  75                  80

Val Tyr Leu Pro Leu Asn Thr Ala Tyr Thr Leu Ala Glu Leu Glu Tyr
                85                  90                  95

Phe Leu Ser Asp Ala Glu Pro Thr Val Val Val Arg Pro Glu Val
            100                 105                 110

Ala Gly Asp Val Lys Ala Leu Ala Ala Lys Leu Gly Val Pro His Val
        115                 120                 125

Glu Thr Leu Gly Ser Asp Gly Lys Gly Ser Leu Thr Glu Ala Ala Ala
    130                 135                 140

Gly Glu Ser Glu Ser Phe Glu Asp Val Pro Arg Ala Ala Asp Leu
145                 150                 155                 160

Ala Gly Ile Leu Tyr Thr Ser Gly Thr Thr Gly Arg Ala Lys Gly Ala
                165                 170                 175

Met Leu Thr His Glu Asn Leu Leu Ser Asn Ala Val Thr Leu Arg Asp
            180                 185                 190

Tyr Trp Arg Phe Thr Ser Asp Asp Val Leu Ile His Ala Leu Pro Ile
        195                 200                 205

Phe His Thr His Gly Leu Phe Val Ala Gly Asp Ile Ile Leu Met Ala
    210                 215                 220

Gly Ala Ser Met Ile Phe Cys Pro Lys Phe Asp Ala Ser Glu Val Leu
225                 230                 235                 240

Arg Leu Met Pro Lys Ala Thr Thr Leu Met Gly Val Pro Thr Phe Tyr
                245                 250                 255

Thr Arg Leu Leu Asp His Pro Gly Leu Thr Arg Glu Ala Thr His
            260                 265                 270

Met Arg Leu Phe Val Ser Gly Ser Ala Pro Leu Leu Ala Glu Thr His
        275                 280                 285

Arg Ala Phe Gln Glu Lys Thr Gly Lys Ala Ile Leu Glu Arg Tyr Gly
    290                 295                 300

Met Thr Glu Thr Gly Met Asn Thr Ser Asn Pro Tyr Asp Gly Glu Arg
305                 310                 315                 320

Ile Ala Gly Thr Val Gly Phe Pro Leu Pro Gly Val Ser Val Arg Ile
                325                 330                 335

Thr Asp Pro Ala Thr Gly Ala Val Leu Gly Ala Asp Glu Ile Gly Ser
            340                 345                 350
```

```
Ile Glu Val Lys Gly Pro Asn Val Phe Lys Gly Tyr Trp Lys Leu Pro
            355                 360                 365

Glu Lys Thr Ala Ser Glu Phe His Asp Gly Phe Phe Ile Thr Gly Asp
    370                 375                 380

Leu Gly Lys Ile Asp Ala Arg Gly Tyr Val His Ile Val Gly Arg Gly
385                 390                 395                 400

Lys Asp Leu Val Ile Thr Gly Gly Phe Asn Val Tyr Pro Lys Glu Val
                405                 410                 415

Glu Gly Glu Ile Asp Ala Leu Pro Gly Val Leu Glu Ser Ala Val Ile
            420                 425                 430

Gly Leu Pro His Lys Asp Phe Gly Gly Val Thr Ala Val Ile Val
            435                 440                 445

Arg Thr Pro Gly Ala Ser Leu Thr Glu Ala Glu Val His Gln Ala Leu
    450                 455                 460

Glu Gly Arg Leu Ala Lys Phe Lys Leu Pro Lys Lys Val Phe Phe Val
465                 470                 475                 480

Asp Glu Leu Pro Arg Asn Thr Met Gly Lys Val Gln Lys Asn Ile Leu
                485                 490                 495

Arg Asp Thr Tyr Lys Asp Thr Tyr Arg Ser Val Ala
            500                 505

<210> SEQ ID NO 15
<211> LENGTH: 503
<212> TYPE: PRT
<213> ORGANISM: Rhodopseudomonas palustris BisB5
<220> FEATURE:
<221> NAME/KEY: MISC_FEATURE
<222> LOCATION: (1)..(503)
<223> OTHER INFORMATION: GenBank Accession No. YP_567622

<400> SEQUENCE: 15

Met Asn Ala Asn Leu Phe Ala Arg Leu Phe Asp Ala Leu Asp Asp Pro
1               5                   10                  15

Asn Arg Leu Ala Ile Glu Thr Ala Ala Gly Thr Ile Ser Tyr Gly
            20                  25                  30

Asp Leu Ile Ala Arg Ala Gly Arg Val Ala Asn Val Leu Val Ala Arg
        35                  40                  45

Gly Val Lys Thr Gly Asp Arg Val Ala Gln Thr Glu Lys Ser Val
    50                  55                  60

Glu Ala Leu Val Leu Tyr Leu Ala Thr Val Arg Ala Gly Ala Val Tyr
65                  70                  75                  80

Leu Pro Leu Asn Thr Ala Tyr Thr Leu His Glu Leu Asp Tyr Phe Ile
                85                  90                  95

Thr Asp Ala Glu Pro Ser Leu Val Val Cys Asp Pro Ser Lys Arg Asp
            100                 105                 110

Gly Ile Ala Ala Ile Ala Ala Lys Val Lys Ala Ala Val Glu Thr Leu
        115                 120                 125

Gly Gly Asp Gly Gln Gly Ser Leu Thr Asp Ala Ala Gln Ala Ser
    130                 135                 140

Ala Glu Phe Thr Thr Val Pro Arg Ser Ala Asp Leu Ala Ala Ile
145                 150                 155                 160

Leu Tyr Thr Ser Gly Thr Thr Gly Arg Ser Lys Gly Ala Met Leu Ser
                165                 170                 175

His Asp Asn Leu Ala Ser Asn Ser Leu Thr Leu Val Asp Tyr Trp Arg
            180                 185                 190

Phe Thr Pro Asp Asp Val Leu Ile His Ala Leu Pro Ile Tyr His Thr
```

```
                195                 200                 205
His Gly Leu Phe Val Ala Ser Asn Val Thr Leu Phe Ala Arg Ala Ala
210                 215                 220

Met Ile Phe Leu Pro Lys Leu Asp Pro Asp Arg Ile Ile Asp Leu Met
225                 230                 235                 240

Pro Arg Ala Thr Val Leu Met Gly Val Pro Thr Phe Tyr Thr Arg Leu
                245                 250                 255

Leu Gln Ser Pro Arg Leu Thr Gln Gln Ala Thr Arg His Met Arg Leu
            260                 265                 270

Phe Ile Ser Gly Ser Ala Pro Leu Leu Ala Asp Thr His Arg Glu Trp
        275                 280                 285

Ala Ala Arg Thr Gly His Ala Val Leu Glu Arg Tyr Gly Met Thr Glu
    290                 295                 300

Thr Asn Met Asn Thr Ser Asn Pro Tyr Glu Gly Glu Arg Val Pro Gly
305                 310                 315                 320

Ala Val Gly Phe Pro Leu Pro Gly Val Ser Ala Arg Val Thr Asp Pro
                325                 330                 335

Glu Thr Gly Arg Glu Leu Ala Arg Gly Glu Ile Gly Met Ile Glu Val
            340                 345                 350

Lys Gly Pro Asn Val Phe Lys Gly Tyr Trp Arg Met Pro Glu Lys Thr
        355                 360                 365

Arg Ser Glu Phe Arg Asp Asp Gly Phe Phe Ile Thr Gly Asp Leu Gly
    370                 375                 380

Lys Ile Asp Glu Arg Gly Tyr Val His Ile Leu Gly Arg Gly Lys Asp
385                 390                 395                 400

Leu Val Ile Thr Gly Gly Phe Asn Val Tyr Pro Lys Glu Ile Glu Ser
                405                 410                 415

Glu Ile Asp Ala Met Pro Gly Val Val Glu Ser Ala Val Ile Gly Val
            420                 425                 430

Pro His Ala Asp Phe Gly Glu Gly Val Thr Ala Val Val Val Arg Asp
        435                 440                 445

Lys Gly Ala Ala Ile Asp Glu Ala Gln Val Leu Ser Gly Leu Asp Gly
    450                 455                 460

Gln Ile Ala Lys Phe Lys Met Pro Lys Lys Val Ile Phe Val Asp Asp
465                 470                 475                 480

Leu Pro Arg Asn Thr Met Gly Lys Val Gln Lys Asn Val Leu Arg Asp
                485                 490                 495

Thr Tyr Ala Asp Ile Tyr Lys
            500

<210> SEQ ID NO 16
<211> LENGTH: 508
<212> TYPE: PRT
<213> ORGANISM: Bradyrhizobium sp. ORS278
<220> FEATURE:
<221> NAME/KEY: MISC_FEATURE
<222> LOCATION: (1)..(508)
<223> OTHER INFORMATION: GenBank Accession No. YP_001202443

<400> SEQUENCE: 16

Met Asn His Ala Ala Asn Thr Asn Leu Phe Ala Arg Leu Phe Asp Gly
1               5                   10                  15

Leu Asp Asp Pro Ser Arg Leu Ala Ile Glu Thr His Asp Gly Gln Arg
            20                  25                  30

Ile Thr Tyr Gly Asp Leu Val Ala Arg Ala Gly Gln Met Ala Asn Val
        35                  40                  45
```

```
Leu Val Ser Arg Gly Val Lys Pro Gly Asp Arg Val Ala Ala Gln Thr
     50                  55                  60
Glu Lys Ser Val Ser Gly Leu Val Leu Tyr Leu Ala Thr Val Arg Ala
 65                  70                  75                  80
Gly Gly Val Tyr Leu Pro Leu Asn Thr Ala Tyr Thr Leu Asn Glu Leu
                 85                  90                  95
Asp Tyr Phe Ile Gly Asp Ala Glu Pro Thr Val Val Cys Asp Pro
             100                 105                 110
Ser Lys Ala Glu Gly Ile Gly Ala Leu Ala Ala Lys Val Gly Ala Lys
             115                 120                 125
Val Glu Thr Leu Asp Ala Ser Gly Arg Gly Ser Leu Thr Asp Ala Ala
 130                 135                 140
Asp Lys Ala Glu Thr Ala Phe Ile Thr Val Pro Arg Ala Pro Asp Asp
145                 150                 155                 160
Leu Ala Ala Ile Leu Tyr Thr Ser Gly Thr Thr Gly Arg Ser Lys Gly
                 165                 170                 175
Ala Met Leu Ser His Asp Asn Leu Ala Ser Asn Ser Leu Thr Leu Ile
                 180                 185                 190
Asp Tyr Trp Arg Phe Thr Arg Asp Asp Val Leu Ile His Ala Leu Pro
             195                 200                 205
Ile Tyr His Thr His Gly Leu Phe Val Ala Ser Asn Val Thr Leu Phe
             210                 215                 220
Ala Arg Ala Ser Met Ile Phe Leu Pro Lys Leu Asp Pro Asp Leu Ile
225                 230                 235                 240
Ile Asn Leu Met Ala Arg Ala Thr Val Leu Met Gly Val Pro Thr Phe
                 245                 250                 255
Tyr Thr Arg Leu Leu Gln Asn Pro Arg Leu Ser Lys Glu Thr Thr Ser
                 260                 265                 270
His Met Arg Leu Phe Ile Ser Gly Ser Ala Pro Leu Leu Ala Asp Thr
                 275                 280                 285
His Arg Glu Trp Phe Ala Arg Thr Gly His Ala Val Leu Glu Arg Tyr
             290                 295                 300
Gly Met Thr Glu Thr Asn Met Asn Thr Ser Asn Pro Tyr Ala Gly Glu
305                 310                 315                 320
Arg Val Pro Gly Ala Val Gly Phe Pro Leu Pro Gly Val Ser Val Arg
                 325                 330                 335
Val Thr Asp Pro Glu Thr Gly Lys Glu Leu Ala Arg Asp Asp Ile Gly
                 340                 345                 350
Met Ile Glu Val Lys Gly Pro Asn Val Phe Lys Gly Tyr Trp Arg Met
             355                 360                 365
Pro Glu Lys Thr Lys Ser Glu Phe Arg Pro Asp Gly Phe Phe Ile Thr
             370                 375                 380
Gly Asp Leu Gly Lys Ile Asp Pro Gln Gly Tyr Val His Ile Val Gly
385                 390                 395                 400
Arg Gly Lys Asp Leu Val Ile Ser Gly Gly Phe Asn Val Tyr Pro Lys
                 405                 410                 415
Glu Ile Glu Ser Glu Ile Asp Ala Met Pro Gly Val Val Glu Ser Ala
             420                 425                 430
Val Ile Gly Val Pro His Ala Asp Phe Gly Glu Gly Val Thr Ala Val
             435                 440                 445
Val Val Arg Gln Pro Gly Ala Asp Val Ser Glu Val Gly Val Leu Lys
 450                 455                 460
```

```
Gly Leu Asp Gly Arg Leu Ala Lys Phe Lys Met Pro Lys Arg Val Phe
465                 470                 475                 480

Val Val Asp Glu Leu Pro Arg Asn Thr Met Gly Lys Val Gln Lys Asn
                485                 490                 495

Val Leu Arg Asp Gln Tyr Lys Asp Ile Tyr Thr Lys
            500                 505
```

<210> SEQ ID NO 17
<211> LENGTH: 509
<212> TYPE: PRT
<213> ORGANISM: Xanthobacter autotrophicus Py2
<220> FEATURE:
<221> NAME/KEY: MISC_FEATURE
<222> LOCATION: (1)..(509)
<223> OTHER INFORMATION: GenBank Accession No. YP_001415433

<400> SEQUENCE: 17

```
Met Ser Asp Asn His Leu Phe Gly Ala Ile Arg Ala Ala Met Pro Ala
1               5                   10                  15

Leu Asp Ala Pro Leu Ala Thr Leu Met Asp Gly Arg Val Glu Thr Tyr
            20                  25                  30

Gly Asp Ala Leu Ala Leu Ser Ala Arg Leu Ala His Leu Leu Val Ala
        35                  40                  45

Arg Gly Val Lys Pro Gly Asp Arg Val Ala Val Gln Val Glu Lys Ser
50                  55                  60

Trp Pro Ala Leu Ala Leu Tyr Leu Ala Thr Val Arg Ala Gly Gly Val
65                  70                  75                  80

Tyr Leu Pro Leu Asn Thr Ala Tyr Thr Leu Asn Glu Val Glu Tyr Phe
                85                  90                  95

Leu Ser Asp Ala Glu Pro Thr Leu Phe Val Cys Pro Pro His Ile Glu
            100                 105                 110

Ala Glu Ala Arg Ala Leu Ala Thr Arg Leu Gly Val Pro Ser Val Glu
        115                 120                 125

Thr Leu Gly Ala Asp Gly Thr Gly Ser Leu Thr Asp Gly Ala Ala His
    130                 135                 140

Leu Pro Thr Glu Phe Ala Asp Val Pro Arg Gly Pro Glu Asp Leu Gly
145                 150                 155                 160

Gly Ile Leu Tyr Thr Ser Gly Thr Thr Gly Arg Ala Lys Gly Ala Met
                165                 170                 175

Leu Ser His Asp Asn Leu Leu Ser Asn Ala Leu Thr Leu Lys Asp Glu
            180                 185                 190

Trp Arg Phe Thr Gly Asp Asp Val Leu Leu His Ala Leu Pro Ile Phe
        195                 200                 205

His Thr His Gly Leu Phe Val Ala Ser Asn Ile Val Leu Leu Ala Gly
    210                 215                 220

Ala Ala Met Val Phe Arg Ala Lys Phe Asp Pro Arg Glu Ala Leu Glu
225                 230                 235                 240

Leu Met Ala Ala Gly Thr Val Ser Leu Met Gly Val Pro Thr Phe
                245                 250                 255

Tyr Thr Arg Leu Leu Asp Gln Gln Gly Leu Thr Arg Glu Ala Thr Ala
            260                 265                 270

Lys Met Arg Leu Phe Val Ser Gly Ser Ala Pro Leu Leu Ala Glu Thr
        275                 280                 285

His Arg Ala Phe Phe Glu Arg Thr Gly His Ala Ile Leu Glu Arg Tyr
    290                 295                 300

Gly Met Thr Glu Thr Gly Met Asn Thr Ser Asn Pro Tyr Asp Gly Glu
```

```
                305                 310                 315                 320
Arg Ile Ala Gly Thr Val Gly Phe Pro Leu Pro Gly Ile Val Leu Arg
                325                 330                 335

Val Thr Asp Pro Glu Thr Gly Arg Val Leu Pro Thr Asp Asp Ile Gly
                340                 345                 350

Met Ile Glu Val Lys Gly Pro Asn Val Phe Lys Gly Tyr Trp Arg Met
                355                 360                 365

Pro Glu Lys Thr Ala Ala Glu Phe Arg Asp Gly Phe Phe Ile Thr Gly
                370                 375                 380

Asp Leu Gly Lys Ile Asp Ala Arg Gly Tyr Val His Ile Val Gly Arg
385                 390                 395                 400

Gly Lys Asp Leu Val Ile Thr Gly Gly Phe Asn Val Tyr Pro Lys Glu
                405                 410                 415

Val Glu Gly Glu Ile Asp Ala Ile Pro Gly Val Ala Glu Ser Ala Val
                420                 425                 430

Ile Gly Val Pro His Pro Asp Phe Gly Glu Gly Val Thr Ala Val Val
                435                 440                 445

Val Lys Val Ala Gly Ala Ser Leu Thr Glu Ala Asp Ile His Ala Ala
                450                 455                 460

Leu Glu Ser Arg Leu Ala Lys Phe Lys Gln Pro Lys Arg Val Phe Phe
465                 470                 475                 480

Val Pro Glu Leu Pro Arg Asn Thr Met Gly Lys Val Gln Lys Asn Val
                485                 490                 495

Leu Arg Glu Thr Tyr Lys Asp Ile Phe Arg Ala Val Ala
                500                 505

<210> SEQ ID NO 18
<211> LENGTH: 511
<212> TYPE: PRT
<213> ORGANISM: Rhodopseudomonas palustris HaA2
<220> FEATURE:
<221> NAME/KEY: MISC_FEATURE
<222> LOCATION: (1)..(511)
<223> OTHER INFORMATION: GenBank Accession No. YP_483951

<400> SEQUENCE: 18

Met Asn Ala His Gly Asn Thr Asn Met Asn Ala Asn Leu Phe Ala Arg
1               5                   10                  15

Leu Phe Asp Ala Pro Gly Asp Pro Asp Lys Arg Ala Ile Glu Thr Ala
                20                  25                  30

Asp Gly Gly Ser Ile Ser Tyr Gly Glu Leu Val Ala Arg Ala Gly Arg
            35                  40                  45

Val Ala Asn Val Leu Ile Ala Arg Gly Val Lys Ile Gly Asp Arg Val
    50                  55                  60

Ala Ala Gln Thr Glu Lys Ser Val Glu Ala Leu Val Leu Tyr Leu Ala
65                  70                  75                  80

Thr Val Arg Ala Gly Ala Val Tyr Leu Pro Leu Asn Thr Ala Tyr Thr
                85                  90                  95

Leu His Glu Leu Asp Tyr Phe Ile Thr Asp Ala Glu Pro Ser Leu Val
                100                 105                 110

Val Cys Asp Pro Ala Thr Arg Asp Gly Ile Ala Ile Ala Ala Lys
                115                 120                 125

Val Asn Ala Ala Val Glu Thr Leu Asp Ala Gly Gly Gln Gly Ser Leu
                130                 135                 140

Thr Asp Ala Ala Ala Gln Ala Ser Ser Asp Phe Ala Thr Val Pro Arg
145                 150                 155                 160
```

Glu Gly Ser Asp Leu Ala Ala Ile Leu Tyr Thr Ser Gly Thr Thr Gly
                165                 170                 175

Arg Ser Lys Gly Ala Met Leu Ser His Asp Asn Leu Ala Ser Asn Ser
            180                 185                 190

Leu Thr Leu Val Asp Tyr Trp Arg Phe Ser Pro Asp Val Leu Ile
        195                 200                 205

His Ala Leu Pro Ile Tyr His Thr His Gly Leu Phe Val Ala Ser Asn
210                 215                 220

Val Thr Leu Phe Ala Arg Ala Ser Met Ile Phe Leu Pro Lys Leu Asp
225                 230                 235                 240

Pro Glu Arg Ile Ile Asp Leu Met Pro Arg Ala Thr Val Leu Met Gly
                245                 250                 255

Val Pro Thr Phe Tyr Thr Arg Leu Leu Gln Ser Pro Arg Leu Thr Lys
            260                 265                 270

Asp Ala Thr Ser His Met Arg Leu Phe Ile Ser Gly Ser Ala Pro Leu
        275                 280                 285

Leu Ala Glu Thr His Arg Glu Trp Ser Ala Arg Thr Gly His Ala Val
290                 295                 300

Leu Glu Arg Tyr Gly Met Thr Glu Thr Asn Met Asn Thr Ser Asn Pro
305                 310                 315                 320

Tyr Asp Gly Glu Arg Val Pro Gly Ala Val Gly Phe Pro Leu Pro Gly
                325                 330                 335

Val Ser Val Arg Val Thr Asp Pro Asp Ala Gly Arg Glu Leu Pro Arg
            340                 345                 350

Gly Glu Ile Gly Met Ile Glu Val Lys Gly Pro Asn Val Phe Lys Gly
        355                 360                 365

Tyr Trp Arg Met Pro Glu Lys Thr Ala Ala Glu Phe Arg Pro Asp Gly
370                 375                 380

Phe Phe Ile Thr Gly Asp Leu Gly Lys Ile Asp Glu Arg Gly Tyr Val
385                 390                 395                 400

His Ile Leu Gly Arg Gly Lys Asp Leu Val Ile Thr Gly Gly Phe Asn
                405                 410                 415

Val Tyr Pro Lys Glu Ile Glu Ser Glu Ile Asp Ala Met Pro Gly Val
            420                 425                 430

Val Glu Ser Ala Val Ile Gly Leu Pro His Ala Asp Phe Gly Glu Gly
        435                 440                 445

Val Thr Ala Val Val Arg Ser Ser Gln Ser Ser Leu Asp Glu Ala
450                 455                 460

Glu Val Leu Lys Ser Leu Asp Gly Gln Ile Ala Lys Phe Lys Met Pro
465                 470                 475                 480

Lys Lys Val Ile Ile Val Asp Glu Leu Pro Arg Asn Thr Met Gly Lys
                485                 490                 495

Val Gln Lys Asn Val Leu Arg Ser Thr Tyr Lys Asp Ile Tyr Lys
            500                 505                 510

<210> SEQ ID NO 19
<211> LENGTH: 532
<212> TYPE: PRT
<213> ORGANISM: Oligotropha carboxidovorans OM5
<220> FEATURE:
<221> NAME/KEY: MISC_FEATURE
<222> LOCATION: (1)..(532)
<223> OTHER INFORMATION: GenBank Accession No. YP_002210100

<400> SEQUENCE: 19

```
Met Arg Arg Gly Phe Gly Lys Ala Lys Thr Pro Leu Met Leu Asp Gln
1               5                   10                  15

Pro Met Thr Thr Pro Ala Lys Pro Thr Pro Ala Asn Ala Asn Leu Tyr
            20                  25                  30

Ala Arg Leu Phe Asn Asp Met Lys Glu Pro Leu Lys Thr Ala Ile Glu
            35                  40                  45

Pro Asp Gly Gly Thr Pro Ile Ser Tyr Arg Glu Leu Asp Ala Gln Ala
50                  55                  60

Ala Arg Tyr Ala Asn Tyr Leu Thr Ala Cys Gly Val Lys Thr Gly Asp
65                  70                  75                  80

Arg Val Ala Val Gln Val Glu Lys Ser Thr Ala Ala Val Met Leu Tyr
                85                  90                  95

Leu Ala Thr Val Arg Ala Gly Ala Ile Phe Leu Pro Leu Asn Thr Ala
            100                 105                 110

Tyr Thr Leu Asn Glu Leu Asp Tyr Phe Gly Asp Ala Glu Pro Ala
            115                 120                 125

Leu Ile Val Cys Asp Pro Ser Lys Ala Glu Gly Ile Ala Lys Ile Ala
130                 135                 140

Gln Pro Ile Gly Ala Arg Val Glu Thr Leu Asp Ser Glu Gly Arg Gly
145                 150                 155                 160

Ser Leu Ala Asp Gly Ala Thr Lys Ser Ala Asp Ser Phe Thr Thr Val
            165                 170                 175

Gln Arg Glu Gly Ser Asp Leu Ala Ala Ile Leu Tyr Thr Ser Gly Thr
            180                 185                 190

Thr Gly Arg Ser Lys Gly Ala Met Leu Thr His Asp Asn Leu Ala Ser
            195                 200                 205

Asn Ser Leu Ser Leu Val Glu Ile Trp His Phe Thr Asp Lys Asp Val
210                 215                 220

Leu Ile His Ala Leu Pro Ile Tyr His Thr His Gly Leu Phe Val Ala
225                 230                 235                 240

Ile Asn Val Cys Leu Phe Ser Gly Ala Thr Met Ile Phe Leu Lys Lys
            245                 250                 255

Leu Asp Thr Asp Arg Ile Ile Asp Leu Met Pro Arg Ser Thr Val Leu
            260                 265                 270

Met Gly Val Pro Thr Phe Tyr Val Arg Leu Leu Gln Asn Pro Arg Leu
            275                 280                 285

Thr Lys Glu Ala Ala Ser His Met Arg Leu Phe Ile Ser Gly Ser Ala
            290                 295                 300

Pro Leu Leu Ala Glu Thr His Arg Glu Trp Ser Ala Arg Thr Gly His
305                 310                 315                 320

Ala Val Leu Glu Arg Tyr Gly Met Thr Glu Thr Asn Met Ser Thr Ser
            325                 330                 335

Asn Pro Tyr Asp Gly Asp Arg Val Pro Gly Ala Val Gly Phe Pro Leu
            340                 345                 350

Pro Gly Val Thr Met Arg Val Thr Asp Pro Glu Thr Gly Arg Glu Leu
            355                 360                 365

Ala Arg Asp Glu Ile Gly Met Leu Glu Val Lys Gly Pro Asn Val Phe
370                 375                 380

Lys Gly Tyr Trp Arg Met Pro Glu Lys Thr Lys Thr Glu Phe Arg Glu
385                 390                 395                 400

Asp Gly Phe Phe Ile Thr Gly Asp Leu Gly Lys Ile Asp Pro Arg Gly
            405                 410                 415

Tyr Val His Ile Ile Gly Arg Gly Lys Asp Leu Val Ile Ser Gly Gly
```

```
                    420                 425                 430
Phe Asn Val Tyr Pro Lys Glu Ile Glu Ser Glu Ile Asp Ala Ile Pro
                435                 440                 445

Gly Val Val Glu Ser Ala Val Ile Gly Val Pro His Ala Asp Phe Gly
450                 455                 460

Glu Gly Val Thr Ala Val Val Pro Asp Lys Thr Ala Lys Leu Asp
465                 470                 475                 480

Glu Ala Ala Ile Leu His Ala Leu Asp Gly Arg Leu Ala Lys Phe Lys
                485                 490                 495

Leu Pro Lys Arg Val Leu Phe Ile Asn Glu Leu Pro Arg Asn Thr Met
                500                 505                 510

Gly Lys Val Gln Lys Asn Ile Leu Arg Asp Thr Tyr Ala Thr Leu Tyr
            515                 520                 525

Thr Gly Ala Lys
            530

<210> SEQ ID NO 20
<211> LENGTH: 503
<212> TYPE: PRT
<213> ORGANISM: Rhodopseudomonas palustris CGA009
<220> FEATURE:
<221> NAME/KEY: MISC_FEATURE
<222> LOCATION: (1)..(503)
<223> OTHER INFORMATION: GenBank Accession No. NP_945574

<400> SEQUENCE: 20

Met Asn Ala Asn Leu Phe Ala Arg Leu Phe Asp Lys Leu Asp Asp Pro
1               5                   10                  15

His Lys Leu Ala Ile Glu Thr Ala Ala Gly Asp Lys Ile Ser Tyr Ala
                20                  25                  30

Glu Leu Val Ala Arg Ala Gly Arg Val Ala Asn Val Leu Val Ala Arg
            35                  40                  45

Gly Leu Gln Val Gly Asp Arg Val Ala Ala Gln Thr Glu Lys Ser Val
        50                  55                  60

Glu Ala Leu Val Leu Tyr Leu Ala Thr Val Arg Ala Gly Gly Val Tyr
65                  70                  75                  80

Leu Pro Leu Asn Thr Ala Tyr Thr Leu His Glu Leu Asp Tyr Phe Ile
                85                  90                  95

Thr Asp Ala Glu Pro Lys Ile Val Val Cys Asp Pro Ser Lys Arg Asp
                100                 105                 110

Gly Ile Ala Ala Ile Ala Ala Lys Val Gly Ala Thr Val Glu Thr Leu
            115                 120                 125

Gly Pro Asp Gly Arg Gly Ser Leu Thr Asp Ala Ala Ala Gly Ala Ser
        130                 135                 140

Glu Ala Phe Ala Thr Ile Asp Arg Gly Ala Asp Leu Ala Ala Ile
145                 150                 155                 160

Leu Tyr Thr Ser Gly Thr Thr Gly Arg Ser Lys Gly Ala Met Leu Ser
                165                 170                 175

His Asp Asn Leu Ala Ser Asn Ser Leu Thr Leu Val Asp Tyr Trp Arg
                180                 185                 190

Phe Thr Pro Asp Asp Val Leu Ile His Ala Leu Pro Ile Tyr His Thr
            195                 200                 205

His Gly Leu Phe Val Ala Ser Asn Val Thr Leu Phe Ala Arg Gly Ser
        210                 215                 220

Met Ile Phe Leu Pro Lys Phe Asp Pro Asp Lys Ile Leu Asp Leu Met
225                 230                 235                 240
```

```
Ala Arg Ala Thr Val Leu Met Gly Val Pro Thr Phe Tyr Thr Arg Leu
                245                 250                 255

Leu Gln Ser Pro Arg Leu Thr Lys Glu Thr Thr Gly His Met Arg Leu
            260                 265                 270

Phe Ile Ser Gly Ser Ala Pro Leu Leu Ala Asp Thr His Arg Glu Trp
        275                 280                 285

Ser Ala Lys Thr Gly His Ala Val Leu Glu Arg Tyr Gly Met Thr Glu
    290                 295                 300

Thr Asn Met Asn Thr Ser Asn Pro Tyr Asp Gly Asp Arg Val Pro Gly
305                 310                 315                 320

Ala Val Gly Pro Ala Leu Pro Gly Val Ser Ala Arg Val Thr Asp Pro
                325                 330                 335

Glu Thr Gly Lys Glu Leu Pro Arg Gly Asp Ile Gly Met Ile Glu Val
            340                 345                 350

Lys Gly Pro Asn Val Phe Lys Gly Tyr Trp Arg Met Pro Glu Lys Thr
        355                 360                 365

Lys Ser Glu Phe Arg Asp Asp Gly Phe Phe Ile Thr Gly Asp Leu Gly
    370                 375                 380

Lys Ile Asp Glu Arg Gly Tyr Val His Ile Leu Gly Arg Gly Lys Asp
385                 390                 395                 400

Leu Val Ile Thr Gly Gly Phe Asn Val Tyr Pro Lys Glu Ile Glu Ser
                405                 410                 415

Glu Ile Asp Ala Met Pro Gly Val Val Glu Ser Ala Val Ile Gly Val
            420                 425                 430

Pro His Ala Asp Phe Gly Glu Gly Val Thr Ala Val Val Val Arg Asp
        435                 440                 445

Lys Gly Ala Thr Ile Asp Glu Ala Gln Val Leu His Gly Leu Asp Gly
    450                 455                 460

Gln Leu Ala Lys Phe Lys Met Pro Lys Lys Val Ile Phe Val Asp Asp
465                 470                 475                 480

Leu Pro Arg Asn Thr Met Gly Lys Val Gln Lys Asn Val Leu Arg Glu
                485                 490                 495

Thr Tyr Lys Asp Ile Tyr Lys
            500

<210> SEQ ID NO 21
<211> LENGTH: 509
<212> TYPE: PRT
<213> ORGANISM: Bradyrhizobium japonicum USDA 110
<220> FEATURE:
<221> NAME/KEY: MISC_FEATURE
<222> LOCATION: (1)..(509)
<223> OTHER INFORMATION: GenBank Accession No. NP_767149

<400> SEQUENCE: 21

Met Asn Arg Ala Ala Asn Ala Asn Leu Phe Ser Arg Leu Phe Asp Gly
1               5                   10                  15

Leu Asp Asp Pro Lys Arg Leu Ala Ile Glu Thr His Asp Gly Ala Arg
            20                  25                  30

Ile Ser Tyr Gly Asp Leu Ile Ala Arg Ala Gly Gln Met Ala Asn Val
        35                  40                  45

Leu Val Ala Arg Gly Val Lys Pro Gly Asp Arg Val Ala Val Gln Val
    50                  55                  60

Glu Lys Ser Val Ala Asn Ile Val Leu Tyr Leu Ala Thr Val Arg Ala
65                  70                  75                  80
```

```
Gly Ala Val Tyr Leu Pro Leu Asn Thr Ala Tyr Thr Leu Asn Glu Leu
                85                  90                  95
Asp Tyr Phe Ile Gly Asp Ala Glu Pro Ser Leu Val Val Cys Asp Pro
            100                 105                 110
Ser Lys Ala Glu Gly Leu Ala Pro Ile Ala Ala Lys Val Lys Ala Gly
        115                 120                 125
Val Glu Thr Leu Gly Pro Asp Gly Lys Gly Ser Leu Thr Glu Ala Ala
    130                 135                 140
Asp Lys Ala Ser Ser Ala Phe Thr Thr Val Pro Arg Glu Asn Asp Asp
145                 150                 155                 160
Leu Ala Ala Ile Leu Tyr Thr Ser Gly Thr Thr Gly Arg Ser Lys Gly
                165                 170                 175
Ala Met Leu Thr His Asp Asn Leu Ala Ser Asn Ser Leu Ser Leu Val
            180                 185                 190
Gly Tyr Trp Arg Phe Thr Asp Lys Asp Val Leu Ile His Ala Leu Pro
        195                 200                 205
Ile Tyr His Thr His Gly Leu Phe Val Ala Thr Asn Val Thr Leu Phe
    210                 215                 220
Ser Arg Ala Ser Met Ile Phe Leu Pro Lys Leu Asp Pro Asp Leu Ile
225                 230                 235                 240
Ile Lys Leu Met Ala Arg Ala Thr Val Leu Met Gly Val Pro Thr Phe
                245                 250                 255
Tyr Thr Arg Leu Leu Gln Asn Ala Ala Leu Ser Arg Glu Thr Thr Arg
            260                 265                 270
His Met Arg Leu Phe Ile Ser Gly Ser Ala Pro Leu Leu Ala Glu Thr
        275                 280                 285
His Arg Glu Trp Ser Ala Arg Thr Gly His Ala Val Leu Glu Arg Tyr
    290                 295                 300
Gly Met Thr Glu Thr Asn Met Asn Thr Ser Asn Pro Tyr Asp Gly Glu
305                 310                 315                 320
Arg Val Pro Gly Ala Val Gly Phe Pro Leu Pro Gly Val Ser Leu Arg
                325                 330                 335
Val Thr Asp Pro Glu Thr Gly Lys Glu Leu Pro Arg Glu Glu Ile Gly
            340                 345                 350
Met Ile Glu Val Lys Gly Pro Asn Val Phe Lys Gly Tyr Trp Arg Met
        355                 360                 365
Pro Glu Lys Thr Lys Ala Glu Phe Arg Pro Asp Gly Phe Phe Ile Thr
    370                 375                 380
Gly Asp Leu Gly Lys Ile Asp Gly Lys Gly Tyr Val His Ile Leu Gly
385                 390                 395                 400
Arg Gly Lys Asp Leu Val Ile Ser Gly Gly Phe Asn Val Tyr Pro Lys
                405                 410                 415
Glu Ile Glu Ser Glu Ile Asp Ala Met Pro Gly Val Val Glu Ser Ala
            420                 425                 430
Val Ile Gly Val Pro His Ala Asp Phe Gly Glu Gly Val Thr Ala Val
        435                 440                 445
Leu Val Cys Asn Lys Gly Ala Glu Val Ser Glu Ala Ser Val Leu Lys
    450                 455                 460
Ala Leu Asp Gly Arg Leu Ala Lys Phe Lys Met Pro Lys Arg Val Phe
465                 470                 475                 480
Val Val Asp Glu Leu Pro Arg Asn Thr Met Gly Lys Val Gln Lys Asn
                485                 490                 495
Val Leu Arg Asp Thr Tyr Lys Asp Ile Tyr Ala Lys Lys
```

<210> SEQ ID NO 22
<211> LENGTH: 503
<212> TYPE: PRT
<213> ORGANISM: Paracoccus denitrificans PD1222
<220> FEATURE:
<221> NAME/KEY: MISC_FEATURE
<222> LOCATION: (1)..(503)
<223> OTHER INFORMATION: GenBank Accession No. ZP_00629462

<400> SEQUENCE: 22

```
Met Ser Asp Asn Leu Phe Asp Leu Leu Thr Ala Gly Ile Ser Asp Pro
1               5                   10                  15

Glu Ala Val Ala Ile Glu Thr Gln Ala Gly Glu Arg Ile Arg Tyr Gly
                20                  25                  30

Asp Leu Ile Ala Arg Ser Gly Arg Met Ala Asn Ala Leu Ala Ala Phe
            35                  40                  45

Gly Val Gln Pro Gly Asp Arg Val Ala Val Gln Val Glu Lys Ser Val
        50                  55                  60

Gln Ala Ile Ile Leu Tyr Leu Ala Thr Leu Arg Ala Gly Ala Val Phe
65                  70                  75                  80

Leu Pro Leu Asn Thr Gly Tyr Thr Pro Ala Glu Ile Gly Tyr Phe Leu
                85                  90                  95

Gly Asp Ala Glu Pro Arg Val Phe Val Cys Asp Pro Ala Arg Gln Glu
            100                 105                 110

Ala Leu Arg Gly Pro Thr Glu Ala Ala Gly Ala Arg Met Val Thr Leu
        115                 120                 125

Asp Ala Glu Gly Arg Gly Ser Leu Thr Asp Ala Ala Asp Ala Ala Pro
130                 135                 140

Glu Ala Phe Ala Thr Val Ala Arg Asp Ser Asp Leu Ala Ala Leu
145                 150                 155                 160

Leu Tyr Thr Ser Gly Thr Thr Gly Arg Ser Lys Gly Ala Met Leu Thr
                165                 170                 175

His Gly Asn Leu Val Ser Asn Ala Gln Val Leu Arg Glu Ala Trp Arg
            180                 185                 190

Phe Thr Ala Gln Asp Val Leu Ile His Ala Leu Pro Ile Phe His Thr
        195                 200                 205

His Gly Leu Phe Val Ala Thr Asn Val Val Leu Phe Ser Gly Ala Ser
    210                 215                 220

Met Ile Phe Leu Pro Lys Phe Asp Val Asp Arg Ile Phe Glu Gly Met
225                 230                 235                 240

Ala Arg Ala Thr Val Leu Met Gly Val Pro Thr Phe Tyr Val Arg Leu
                245                 250                 255

Leu Gln Asp Asp Met Leu Asn Ala Glu Thr Thr Ala Asn Met Arg Leu
            260                 265                 270

Phe Val Ser Gly Ser Ala Pro Leu Leu Ala Glu Thr His Arg Glu Trp
        275                 280                 285

Gln Ala Arg Thr Gly His Ala Ile Leu Glu Arg Tyr Gly Met Thr Glu
    290                 295                 300

Thr Asn Met Asn Ala Ser Asn Pro Tyr Asp Gly Glu Arg Ile Ala Gly
305                 310                 315                 320

Thr Val Gly Leu Pro Leu Pro Gly Thr Glu Ile Val Val Thr Asp Pro
                325                 330                 335

Glu Thr Gly Ala Glu Leu Pro Arg Gly Glu Ile Gly Met Ile Glu Val
            340                 345                 350
```

```
Arg Gly Pro Asn Val Phe Lys Gly Tyr Trp Arg Met Pro Glu Lys Thr
        355                 360                 365

Ala Ala Glu Leu Arg Asp Asn Gly Phe Phe Ile Thr Gly Asp Leu Gly
    370                 375                 380

Lys Phe Asp Glu Arg Gly Tyr Leu His Ile Val Gly Arg Gly Lys Asp
385                 390                 395                 400

Leu Ile Ile Thr Gly Gly Tyr Asn Val Tyr Pro Lys Glu Ile Glu Thr
                405                 410                 415

Glu Ile Asp Ala Leu Pro Gly Val Val Glu Ser Ala Val Ile Gly Leu
            420                 425                 430

Pro His Arg Asp Phe Gly Glu Gly Val Thr Ala Val Val Val Pro Thr
            435                 440                 445

Gly Ser Pro Ala Leu Thr Glu Ala Asp Val Leu Ala Pro Leu Glu Gly
    450                 455                 460

Arg Leu Ala Lys Phe Lys Gln Pro Lys Arg Val Leu Phe Met Asp Glu
465                 470                 475                 480

Leu Pro Arg Asn Thr Met Gly Lys Val Gln Lys Asn Leu Leu Arg Asp
                485                 490                 495

Arg Phe Ala Gly Leu Tyr Asp
                500
```

REDUCING BYPRODUCTION OF MALONATES BY YEAST IN A FERMENTATION PROCESS

This application claims the benefit of U.S. Provisional Application No. 61/138,922, filed Dec. 18, 2008, the disclosure of which is hereby incorporated by reference in its entirety.

SEQUENCE LISTING

The sequence listing submitted via EFS, in compliance with 37 C.F.R. §1.52(e), is incorporated herein by reference. The sequence listing text file submitted via EFS contains the file "CL4323USNA_SequenceListing" created on Dec. 10, 2009, which is 114,688 bytes in size.

FIELD OF THE INVENTION

This invention is in the field of biotechnology. More specifically, this invention pertains to methods useful for reducing the by-production of organic acids, and in particular malonates, during fermentation of an organism, based on expression of a gene encoding malonyl-CoA synthetase.

BACKGROUND OF THE INVENTION

Fermentation is a process to produce one or more products from one or more substrates through use of a biocatalyst, wherein the biocatalyst can be a whole microorganism, an isolated enzyme, or any combination thereof.

In a batch fermentation, fermentation begins with a culturing process in which the medium is inoculated with the desired microbial organism. Growth or metabolic activity then occurs. The metabolite and biomass compositions of the system change constantly up to the time the culture is terminated. Typically, the growth rate of the microbial cells proceeds through a static lag phase, to a high-growth log phase (or exponential growth), and finally to a stationary phase, wherein growth is diminished or halted. Although production of the microbial product typically occurs during the high-growth log phase, this phase of growth cannot continue indefinitely because the medium becomes depleted of nutrients and enriched with products, if the product is secreted, and byproducts, as a result of the cultured organisms' growth. Byproducts may comprise among other things, polysaccharides, carbohydrates, amino acids, proteins, salts and various organic acids such as lactic acid, acetic acid, formic acid, proprionic acid, pyruvate, fumarate, citrate, isocitrate, glyocylate, succinate, α-ketoglutarate and malonates.

Fermentation is an important technology for biosynthesis of a variety of microbial products, including amino acids, ethanol, polyunsaturated fatty acids and antibiotics. The fermentative production and commercialization of a few chemicals have been reported (W. Crueger and A. Crueger, *Biotechnology: A Textbook of Industrial Microbiology*, Sinauer Associates: Sunderland, Mass., pp 124-174 (1990); B. Atkinson and F. Mavituna, *Biochemical Engineering and Biotechnology Handbook*, 2nd ed.; Stockton: N.Y., pp 243-364 (1991)). Biocatalytic processes, however, frequently suffer from several well-known limitations which may include: 1) a relatively small range of products; 2) low yields, titers and productivities; 3) difficulty recovering and purifying products from aqueous solutions; and, 4) generation of unwanted byproducts. Integrating upstream metabolic engineering (i.e., product synthesis) with downstream bioprocess engineering (i.e., product separation and process design) is critical to reap significant value from industrial fermentation because process limitations increase the cost of manufacture of the product of interest.

Although various biochemical, physiological and chemical/physical factors can affect the productivity of a biocatalytic process, important factors include the efficiency of the conversion of the substrate to product and the optimization of energy/carbon flow into the biochemical pathway that results in the product of interest. In consideration of these factors, a variety of metabolic engineering techniques have been developed to facilitate up-regulating desirable biochemical pathways and down-regulating undesirable biochemical pathways, such as those that compete with the biosynthetic pathway of interest or those that interfere with production of a particular end-product.

The present disclosure concerns the accumulation of malonates as byproducts during the fermentative synthesis of a product by an organism. Specifically, high productivity and minimal waste byproduct are achieved by engineering the organism to express a heterologous malonyl-CoA synthetase to enable the reaction: malonate+ATP+CoA→malonyl-CoA+AMP+pyrophosphate ["PPi"]. Conversion of the byproduct malonate to malonyl-CoA permits synthesis of fatty acids within the organism, thereby avoiding accumulation of malonate "byproducts" that can not be further utilized during the fermentation. This thereby avoids carbon and energy waste within the organism, reduces the amount of base required to maintain an optimal pH range during the fermentation process, and reduces the amount of byproduct organic acids that require neutralization within the fermentation waste steam.

Heterologous malonyl CoA synthetases have been previously expressed in microbial organisms to enable enhanced production of various polyketides (U.S. Pat. No. 6,939,691, U.S. Pat. App. Pub. No. 2003/0073205). As summarized in Lombó F., et al. (*Biotechnol. Prog.*, 17(4):612-7 (2001)), the productivity of polyketide fermentation processes in natural and heterologous hosts is frequently limited by the in vivo availability of precursors derived from α-carboxylated CoA thioesters such as malonyl-CoA and (2S)-methylmalonyl-CoA. Expression of a malonyl-CoA synthetase can alleviate this limitation and significantly increase polyketide production. Previous disclosures do not contemplate expression of a heterologous malonyl CoA synthetase to reduce production of malonates and thereby avoid carbon and energy waste by the organism.

Applicants have solved the stated problem whereby malonate "byproducts" accumulate during the fermentation of an organism, leading to carbon and energy waste, reduced synthesis of the product of interest and production of waste streams that require neutralization (thereby increasing the overall cost of manufacture). Novel organisms expressing heterologous malonyl CoA synthetase proteins are described herein.

SUMMARY OF THE INVENTION

In a first embodiment, the invention concerns a transgenic organism useful in fermentation of at least one product, comprising at least one gene encoding malonyl-CoA synthetase under control of at least one regulatory sequence; wherein the transgenic organism produces a reduced amount of malonates as a fermentation byproduct compared with the amount of malonates produced by the same organism, whether transgenic or not transgenic, provided that the organism:
 a) does not comprise a gene encoding malonyl-CoA synthetase; or,
 b) comprises a gene encoding malonyl-CoA synthetase that is not expressed.

Preferably, the organism accumulates oil in an amount of at least about 25% of its dry cell weight. The organism can be selected from the group consisting of algae, fungi, euglenoids, yeast, bacteria and stramenopiles. More preferably, the organism is an oleaginous yeast selected from the group consisting of *Yarrowia*, *Candida*, *Rhodotorula*, *Rhodosporidium*, *Cryptococcus*, *Trichosporon* and *Lipomyces*.

In a second embodiment, the regularoty comprised by the transgenic organism of invention further comprises a strong promoter.

In a third embodiment, the transgenic organism of the invention comprising at least one gene encoding malonyl-CoA synthetase can be in multicopy.

In a fourth embodiment, the transgenic organism the invention comprises at least one sequence encoding a malonyl-CoA synthetase polypeptide having an amino acid sequence selected from the group consisting of SEQ ID NO:2, SEQ ID NO:4, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 and SEQ ID NO:22.

In a fifth embodiment, the transgenic organism of the invention comprises at least one sequence encoding a malonyl-CoA synthetase wherein said sequence is selected from the group consisting of SEQ ID NO:1 and SEQ ID NO:3.

In a sixth embodiment, the transgenic organism of the invention produces a titer of the at least one product is not reduced relative to the titer of the at least one product produced by the same organism, whether transgenic or not transgenic, provided that the organism:
 a) does not comprise a gene encoding malonyl-CoA synthetase; or,
 b) comprises a gene encoding malonyl-CoA synthetase that is not expressed.

In a seventh embodiment, the transgenic organism of the invention further comprises at least one genetic mutation. This at least one genetic mutation can be a disruption in at least one native peroxisome biogenesis factor protein.

In an eighth embodiment, the invention comprises a method for manipulating the content of malonates in a transgenic organism, comprising:
 a) providing a transgenic organism useful in fermentation of at least one product where the transgenic organism comprises at least one gene encoding a malonyl-CoA synthetase under the control of suitable regulatory sequences; and,
 b) growing the organism to allow expression of the at least one gene encoding a malonyl-CoA synthetase, such that the transgenic organism makes a reduced amount of malonates as a fermentation byproduct compared with the amount of malonates made by the same organism, whether transgenic or not transgenic, provided that the organism:
  (i) does not comprise a gene encoding malonyl-CoA synthetase; or,
  (ii) comprises a gene encoding malonyl-CoA synthetase that is not expressed.

Preferably, the at least one gene encoding a malonyl-CoA synthetase polypeptide has an amino acid sequence selected from the group consisting of SEQ ID NO:2, SEQ ID NO:4, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 and SEQ ID NO:22. Furthermore, the at least one gene encoding a malonyl-CoA synthetase is selected from the group consisting of SEQ ID NO:1 and SEQ ID NO:3.

In a ninth embodiment, the transgenic *Yarrowia* sp. host cell comprises:
 a) at least one genetic mutation, wherein the mutation is a disruption in at least one native peroxisome biogenesis factor protein; and,
 b) at least one gene encoding malonyl-CoA synthetase under control of at least one regulatory sequence; and,
 c) genes encoding a functional polyunsaturated fatty acid biosynthetic pathway.

BRIEF DESCRIPTION OF THE DRAWINGS AND SEQUENCE LISTINGS

FIG. 1 consists of FIG. 1A, FIG. 1B, FIG. 1C and FIG. 1D, which together show a comparison of the DNA sequence of the *Rhizobium leguminosarum* bv. *viciae* 3841 malonyl-CoA synthetase gene (GenBank Accession No. YP_766603; SEQ ID NO:1) and the synthetic gene (SEQ ID NO:3) codon-optimized for expression in *Yarrowia lipolytica*.

FIG. 2 provides a plasmid map for pZP2-MCS.

Figure 3A:
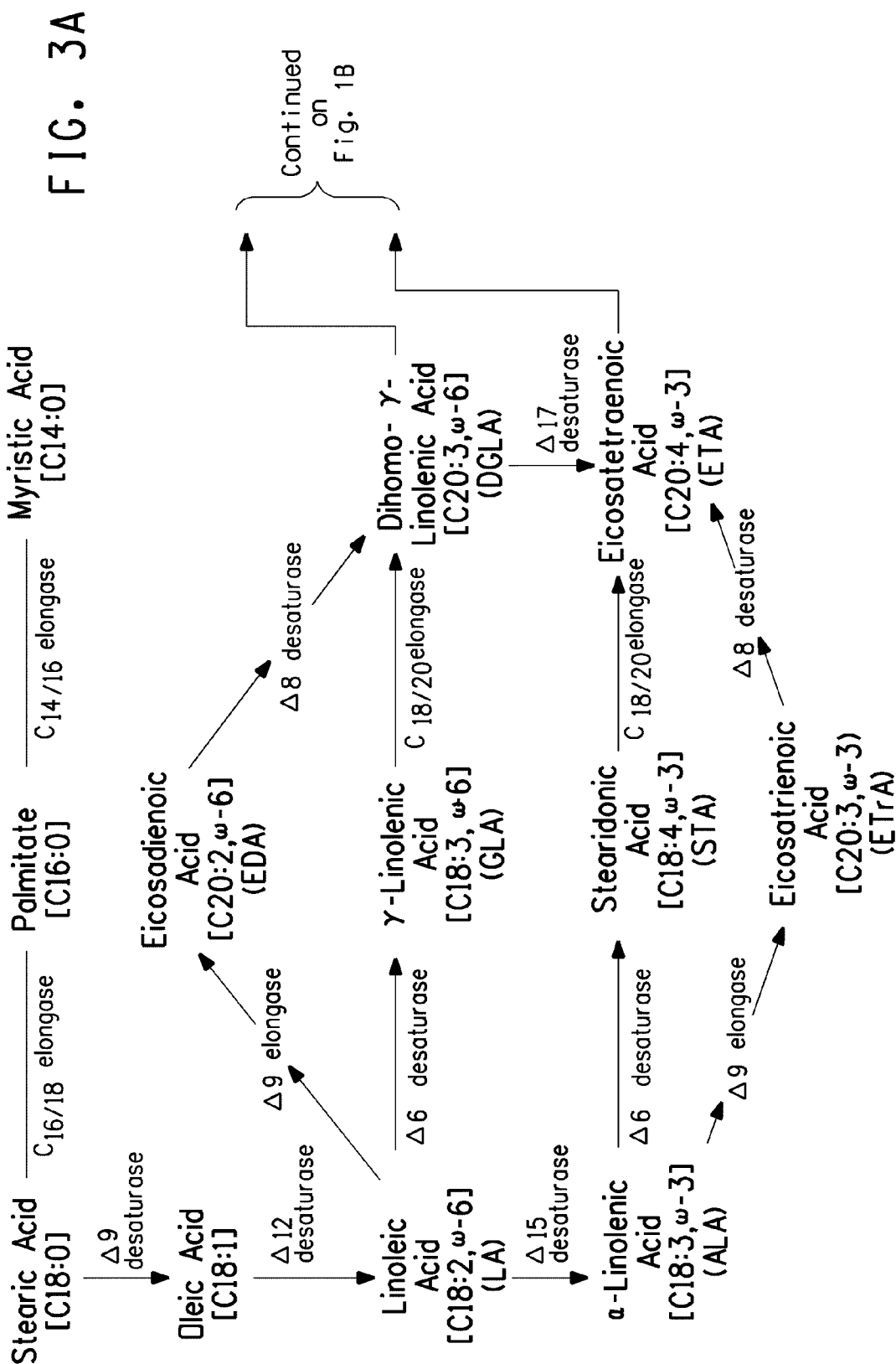
Figure 3B:
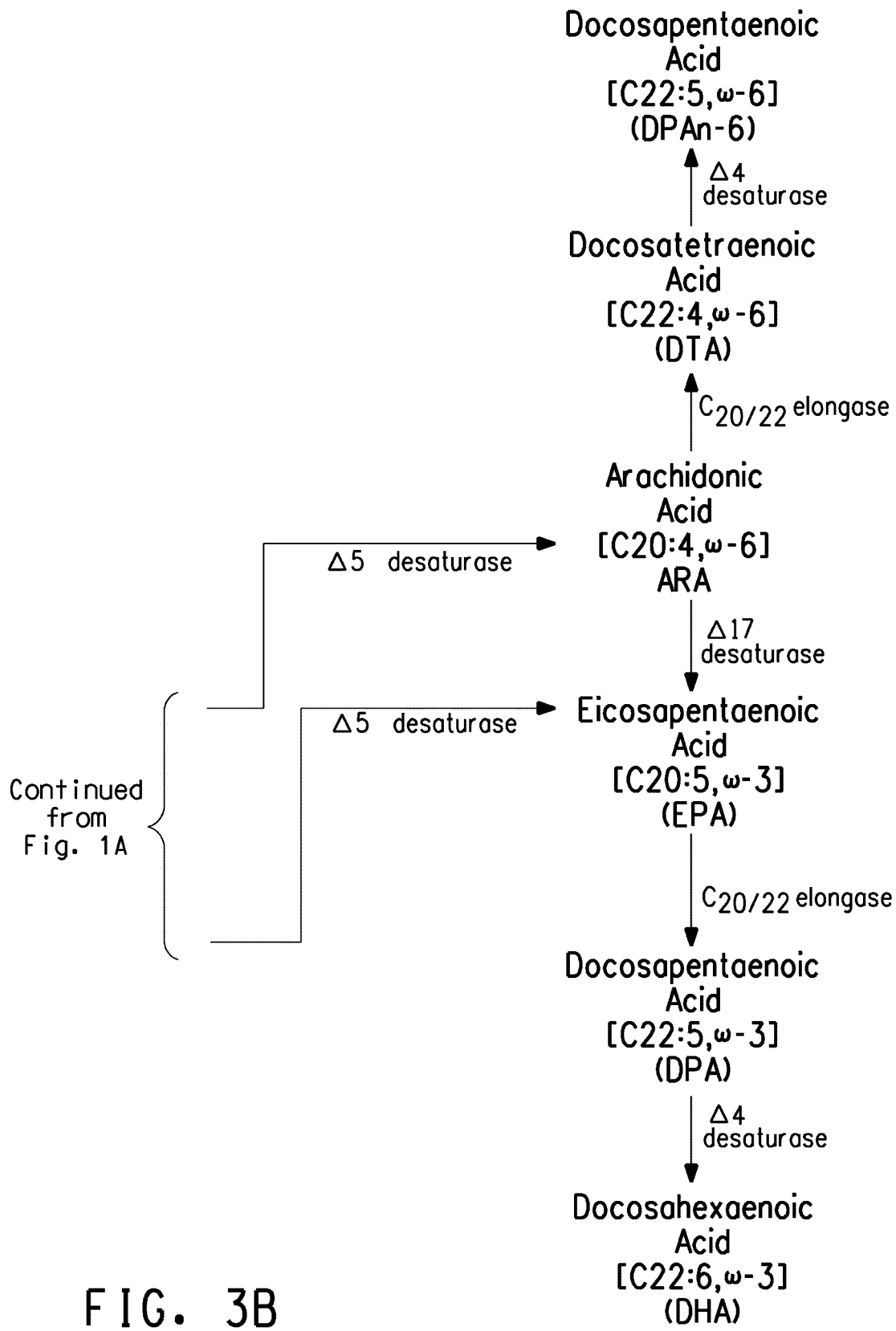

FIG. 3 consists of FIG. 3A and FIG. 3B, which together illustrate the ω-3/ω-6 fatty acid biosynthetic pathway, and should be viewed together when considering the description of this pathway.

Figure 4:
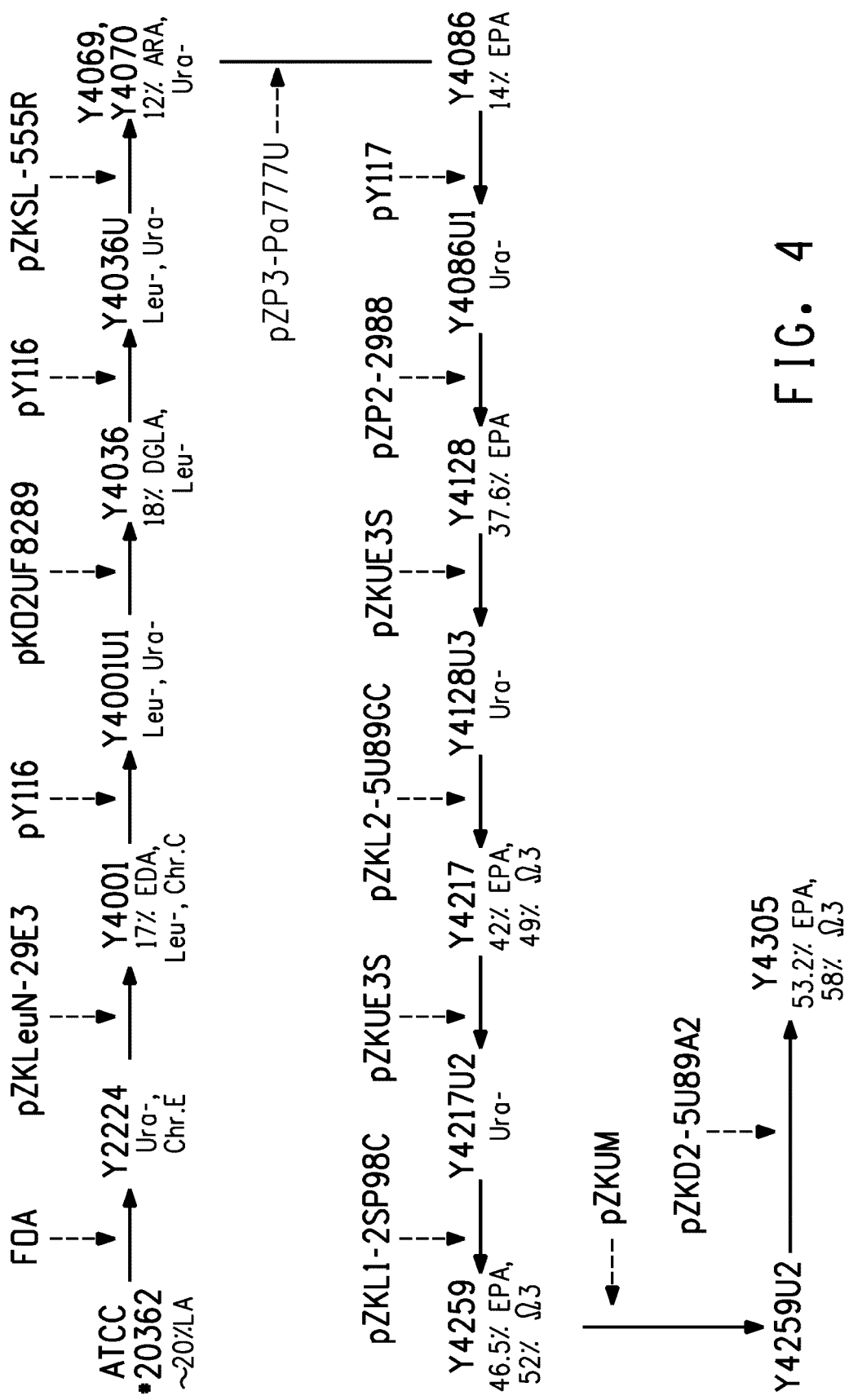

FIG. 4 diagrams the development of *Yarrowia lipolytica* strain Y4305.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-22 are ORFs encoding genes or proteins, or plasmids, as identified in Table 1.

TABLE 1

Summary Of Nucleic Acid And Protein SEQ ID Numbers

| Description and Abbreviation | Nucleic acid SEQ ID NO. | Protein SEQ ID NO. |
|---|---|---|
| *Rhizobium leguminosarum* bv. *viciae* 3841 malonyl-CoA synthetase (GenBank Accession No. YP_766603) ("rMCS") | 1 (1515 bp) | 2 (504 AA) |
| Synthetic malonyl-CoA synthetase derived from *Rhizobium leguminosarum* bv. *viciae* 3841 (GenBank Accession No. YP_766603), codon-optimized for expression in *Yarrowia lipolytica* ("MGS") | 3 (1518 bp) | 4 (505 AA) |
| *Rhizobium trifolii* malonyl-CoA synthetase (GenBank Accession No. AF117694; GenBank Accession No. AAC83455) | — | 5 (504 AA) |
| Plasmid pMCS | 6 (4238 bp) | — |
| Plasmid pZP2-MCS | 7 (9156 bp) | — |
| *Rhizobium etli* CFN 42 (GenBank Accession No. YP_468459) | — | 8 (496 AA) |
| *Sinorhizobium medicae* WSM419 (GenBank Accession No. YP_001313848) | — | 9 (510 AA) |

TABLE 1-continued

Summary Of Nucleic Acid And Protein SEQ ID Numbers

| Description and Abbreviation | Nucleic acid SEQ ID NO. | Protein SEQ ID NO. |
|---|---|---|
| *Mesorhizobium* sp. BNC1 (GenBank Accession No. YP_674146) | — | 10 (506 AA) |
| *Mesorhizobium loti* MAFF303099 (GenBank Accession No. NP_105559) | — | 11 (504 AA) |
| *Bradyrhizobium* sp. BTAi1 (GenBank Accession No. YP_001236428) | — | 12 (508 AA) |
| *Rhodopseudomonas palustris* BisA53 (GenBank Accession No. YP_779412) | — | 13 (504 AA) |
| *Azorhizobium caulinodans* ORS 571 (GenBank Accession No. YP_001526214) | — | 14 (508 AA) |
| *Rhodopseudomonas palustris* BisB5 (GenBank Accession No. YP_567622) | — | 15 (503 AA) |
| *Bradyrhizobium* sp. ORS278 (Gen Bank Accession No. YP_001202443) | — | 16 (508 AA) |
| *Xanthobacter autotrophicus* Py2 (GenBank Accession No. YP_001415433) | — | 17 (509 AA) |
| *Rhodopseudomonas palustris* HaA2 (GenBank Accession No. YP_483951) | — | 18 (511 AA) |
| *Oligotropha carboxidovorans* OM5 (GenBank Accession No. YP_002210100) | — | 19 (532 AA) |
| *Rhodopseudomonas palustris* CGA009 (GenBank Accession No. NP_945574) | — | 20 (503 AA) |
| *Bradyrhizobium japonicum* USDA 110 (GenBank Accession No. NP_767149) | — | 21 (509 AA) |
| *Paracoccus denitrificans* PD1222 (GenBank Accession No. ZP_00629462) | — | 22 (503 AA) |

DETAILED DESCRIPTION OF THE INVENTION

Described herein are generalized methods to avoid accumulation of malonate "byproducts" that cannot be further utilized during a fermentation, during production of a product. These methods rely on expression of a heterologous malonyl-CoA synthetase protein within the host. These methods have wide-spread applicability because they reduce byproduction of malonates by a variety of organisms, including algae, fungi, euglenoids, yeast, bacteria and stramenopiles, during the production of a variety of products via fermentation. These methods were performed in an oleaginous yeast, specifically, *Yarrowia lipolytica*, which had been previously genetically engineered to produce polyunsaturated fatty acids ["PUFAs"]. The genetic mutations relating to engineering production of PUFAs were found to result in increased byproduction of malonates during the fermentation (malonates accounted for ~45% of the total organic acids accumulated). Expression of a heterologous malonyl-CoA synthetase reversed this effect and resulted in substantially reduced byproduction of malonates.

In this disclosure, the following abbreviations are used:
"Open reading frame" is abbreviated as "ORF".
"Polymerase chain reaction" is abbreviated as "PCR".
"American Type Culture Collection" is abbreviated as "ATCC".
"Polyunsaturated fatty acid(s)" is abbreviated as "PUFA(s)".
"Triacylglycerols" are abbreviated as "TAGs".
"Total fatty acids" are abbreviated as "TFAs".
"Fatty acid methyl esters" are abbreviated as "FAMEs".
"Dry cell weight" is abbreviated as "DCW".
"Co enzyme A" is abbreviated as "CoA".

As used herein, the term "invention" or "present invention" is not meant to be limiting but applies generally to any of the inventions defined in the claims or described herein.

The term "malonic acid", also referred to as propanedioic acid according to International Union of Pure and Applied Chemistry ["IUPAC"] systematic nomenclature, refers to a dicarboxylic acid having the chemical structure set forth as $CH_2(COOH)_2$. The malonate or propanedioate ion is derived from malonic acid by loss of two hydrogen ions, (i.e., $CH_2(COO)_2^{2-}$). Salts and esters of malonic acid include, but are not limited to, diethyl malonate $[(C_2H_5)_2(C_3H_2O_4)]$, dimethyl malonate $[(CH_3)_2(C_3H_2O_4)]$ and disodium malonate $[Na_2(C_3H_2O_4)]$.

As used herein, "malonates" refer to the ionised form of malonic acid, as well as its esters and salts. All of these are referred to herein collectively as "malonates".

As used herein, "malonyl-CoA" [CAS Registry No. 524-14-1] refers to an acyl thioester that can be formed by the carboxylation of acetyl-CoA to malonyl-CoA. Alternatively, malonyl-CoA is produced enzymatically from the substrate malonate, via a malonyl-CoA synthetase.

As used herein, "malonyl-CoA synthetase" [EC 6.2.1.-] catalyzes the following enzymatic reaction: malonate+ATP+CoA→malonyl-CoA+AMP+pyrophosphate ["PPi"]. The enzyme was first purified from malonate-grown *Pseudomonas fluorescens* (Kim, Y. S. and S. K. Bang, J. Biol. Chem., 260:5098-5104 (1985)), although various *Rhizobia* homologs have since been isolated from bacteroids within legume nodules (see, for example, Kim, Y. S. and H. Z. Chae, Biochem. J., 273:511-516 (1991) and Kim, Y. S. and S. W. Kang, Biochem. J., 297:327-333 (1994)).

The term "rMCS" refers to a gene (SEQ ID NO:1) encoding a malonyl-CoA synthetase enzyme (SEQ ID NO:2) from *Rhizobium leguminosarum* bv. *viciae* 3841 (GenBank Accession No. YP_766603). Similarly, the term "MCS" refers to a synthetic gene encoding malonyl-CoA synthetase derived from *Rhizobium leguminosarum* bv. *viciae* 3841 that is codon-optimized for expression in *Yarrowia lipolytica* (i.e., SEQ ID NOs:3 and 4).

The term "*Rhizobium*" refers to a genus of Gram-negative soil bacteria (comprising over 30 different species) that fix nitrogen, i.e., diazotrophy. *Rhizobium* form an endosymbiotic nitrogen-fixing association with roots of legumes, such as peas, beans, clover and soy. The bacteria colonize plant cells within root nodules, convert atmospheric nitrogen to ammonia and then provide organic nitrogenous compounds such as glutamine or ureides to the plant. The plant provides the bacteria organic compounds made by photosynthesis. Based on recent studies, *R. trifolii* is a later synonym of *R. leguminosarum* (M. H. Ramírez-Bahena et al., Int. J. Syst. Evol. Microbiol., 58:2484-2490 (2008)).

"Fermentation" refers to a process that catalyzes a reaction(s) to produce product(s) from substrate(s) through use of a biocatalyst(s).

A "biocatalyst" initiates or modifies the rate of a chemical reaction between substrate(s) and product(s). The biocatalyst can be a whole microorganism, an isolated enzyme, or any combination thereof. For the purposes described herein, the biocatalyst will be a whole microorganism, such as an algae, fungus, euglenoid, yeast, bacteria or stramenopile.

A "fermenter" or "bioreactor" refers to a vessel capable of containing a fermentation process. The fermenter is a heterogeneous system having two or more phases, e.g., liquid, gas, solid. Optimal conditions for fermentation necessitate efficient transfer of mass, heat and momentum from one phase to the other. A fermenter provides for the following: 1) agitation (for mixing of cells and medium); 2) aeration, for $O_2$ supply; 3) regulation of factors like temperature, pH, pressure, aeration, nutrient feeding, liquid level, etc.; 4) sterilization and maintenance of sterility; and, 5) withdrawal of cells/medium (for continuous fermenters). Generally, 20-25% of fermenter volume is left unfilled with medium as "head space" to allow for splashing, foaming and aeration. The fermenter design varies greatly depending on the type of fermentation for which it is used. Modern fermenters are usually integrated with computers for efficient process monitoring, data acquisition, etc.

The term "broth" or "medium" refers to a liquid solution containing nutrients for culturing microorganisms, generally comprising water, an energy source, a carbon source, a nitrogen source and micronutrients. During and/or at the end of fermentation, the broth may additionally contain the biocatalyst, product synthesized by the biocatalyst, metabolic intermediates, byproducts and other media components such as salts, vitamins, amino acids, cofactors and antibiotics.

"Product" refers to any biocatalytically-produced primary product of interest that results from the fermentation. This may be a compound naturally produced by the biocatalyst or non-native genes may be genetically engineered into the microorganism for their functional expression during the fermentation.

In contrast, the term "byproduct" refers to a secondary or incidental product derived from the conversion by the biocatalyst of substrate(s) to product(s). Often, it is desirable to selectively remove "byproducts" from the fermentation system to eliminate feedback inhibition and/or to maximize biocatalyst activity. Typical fermentation byproducts may include, for example: polysaccharides, carbohydrates, amino acids, proteins, salts and various organic acids such as lactic acid, acetic acid, formic acid, proprionic acid, pyruvate, fumarate, citrate, isocitrate, glyocylate, succinate, α-ketoglutarate and malonates.

"Volumetric productivity" refers to the mass of product produced in a fermenter in a given volume per time, with units of grams/(liter hour) (abbreviated g/(L hr)). This measure is determined by the specific activity of the biocatalyst and the concentration of the biocatalyst. It is calculated from the titer, run time, and the working volume of the fermenter.

"Titer" refers to the concentration of product with units of grams/liter (abbreviated g/L).

The term "conserved domain" or "motif" refers to a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "oleaginous" refers to those organisms that tend to store their energy source in the form of oil (Weete, In: Fungal Lipid Biochemistry, 2nd Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is common for oleaginous microorganisms to accumulate in excess of about 25% of their dry cell weight as oil.

The term "oleaginous yeast" refers to those microorganisms classified as yeasts that can make oil. Examples of oleaginous yeast include, but are no means limited to, the following genera: *Yarrowia, Candida, Rhodotorula, Rhodosporidium, Cryptococcus, Trichosporon* and *Lipomyces*.

The term "lipids" refer to any fat-soluble (i.e., lipophilic), naturally-occurring molecule. Lipids are a diverse group of compounds that have many key biological functions, such as structural components of cell membranes, energy storage sources and intermediates in signaling pathways. Lipids may be broadly defined as hydrophobic or amphiphilic small molecules that originate entirely or in part from either ketoacyl or isoprene groups. The National Institute of General Medical Sciences (Bethesda, Md.) provides a general overview of lipids, based on the Lipid Metabolites and Pathways Strategy (LIPID MAPS) classification system.

The term "oil" refers to a lipid substance that is liquid at 25° C. and usually polyunsaturated. In oleaginous organisms, oil constitutes a major part of the total lipid. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

The term "triacylglycerols" ["TAGs"] refers to neutral lipids composed of three fatty acyl residues esterified to a glycerol molecule. TAGs can contain long chain PUFAs and saturated fatty acids, as well as shorter chain saturated and unsaturated fatty acids.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

Nomenclature used to describe PUFAs herein is given in Table 2. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of the Table summarizes the common names of ω-3 and ω-6 fatty acids and their precursors, the abbreviations that are used throughout the specification and the chemical name of each compound.

TABLE 2

Nomenclature of Polyunsaturated Fatty Acids And Precursors

| Common Name | Abbreviation | Chemical Name | Shorthand Notation |
|---|---|---|---|
| Myristic | — | Tetradecanoic | 14:0 |
| Palmitic | Palmitate | Hexadecanoic | 16:0 |
| Palmitoleic | — | 9-hexadecenoic | 16:1 |
| Stearic | — | Octadecanoic | 18:0 |
| Oleic | — | cis-9-octadecenoic | 18:1 |
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |

TABLE 2-continued

Nomenclature of Polyunsaturated Fatty Acids And Precursors

| Common Name | Abbreviation | Chemical Name | Shorthand Notation |
|---|---|---|---|
| Dihomo-γ-Linolenic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosatetraenoic | DTA | cis-7,10,13,16-docosatetraenoic | 22:4 ω-3 |
| Docosapentaenoic | DPAn-6 | cis-4,7,10,13,16-docosapentaenoic | 22:5 ω-6 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

Although the ω-3 ω-6 PUFAs listed in Table 2 are the most likely to be accumulated in the oil fractions of oleaginous yeast using the methods described herein, this list should not be construed as limiting or as complete.

The term "PUFA biosynthetic pathway" refers to a metabolic process that converts oleic acid to ω-6 fatty acids such as LA, EDA, GLA, DGLA, ARA, DTA and DPAn-6 and ω-3 fatty acids such as ALA, STA, ETrA, ETA, EPA, DPA and DHA. This process is well described in the literature. See e.g., Intl. App. Pub. No. WO 2006/052870. Briefly, this process involves elongation of the carbon chain through the addition of carbon atoms and desaturation of the elongated molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode them) associated with the biosynthesis of a PUFA, including: Δ4 desaturase, Δ5 desaturase, Δ6 desaturase, Δ12 desaturase, Δ15 desaturase, Δ17 desaturase, Δ9 desaturase, Δ8 desaturase, Δ9 elongase, $C_{14/16}$ elongase, $C_{16/18}$ elongase, $C_{18/20}$ elongase and/or $C_{20/22}$ elongase.

The term "desaturase" refers to a polypeptide that can desaturate adjoining carbons in a fatty acid by removing a hydrogen from one of the adjoining carbons and thereby introducing a double bond between them. Desaturation produces a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are: Δ8 desaturases, Δ5 desaturases, Δ17 desaturases, Δ12 desaturases, Δ4 desaturases, Δ6 desaturases, Δ15 desaturases and Δ9 desaturases. In the art, Δ15 and Δ17 desaturases are also occasionally referred to as "omega-3 desaturases", "ω-3 desaturases", and/or "ω-3 desaturases", based on their ability to convert ω-6 fatty acids into their ω-3 counterparts (e.g., conversion of LA into ALA and ARA into EPA, respectively). It may be desirable to empirically determine the specificity of a particular fatty acid desaturase by transforming a suitable host with the gene for the fatty acid desaturase and determining its effect on the fatty acid profile of the host.

The term "elongase" refers to a polypeptide that can elongate a fatty acid carbon chain to produce an acid 2 carbons longer than the fatty acid substrate that the elongase acts upon. This process of elongation occurs in a multi-step mechanism in association with fatty acid synthase, as described in U.S. Pat. App. Pub. No. 2005/0132442 and Intl. App. Pub. No. WO 2005/047480. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate e.g., myristic acid, a $C_{16/18}$ elongase will utilize a $C_{16}$ substrate e.g., palmitate, a $C_{18/20}$ elongase will utilize a $C_{18}$ substrate (e.g., GLA, STA, LA, ALA) and a $C_{20/22}$ elongase [also referred to as a ΔS elongase] will utilize a $C_{20}$ substrate (e.g., ARA, EPA). For the purposes herein, two distinct types of $C_{18/20}$ elongases can be defined: a Δ6 elongase will catalyze conversion of GLA and STA to DGLA and ETA, respectively, while a Δ9 elongase is able to catalyze the conversion of LA and ALA to EDA and ETrA, respectively.

It is important to note that some elongases have broad specificity and thus a single enzyme may be capable of catalyzing several elongase reactions. For example a single enzyme may thus act as both a $C_{16/18}$ elongase and a $C_{18/20}$ elongase. It may be desirable to empirically determine the specificity of a fatty acid elongase by transforming a suitable host with the gene for the fatty acid elongase and determining its effect on the fatty acid profile of the host.

The terms "conversion efficiency" and "percent substrate conversion" refer to the efficiency by which a particular enzyme, such as a desaturase, can convert substrate to product. The conversion efficiency is measured according to the following formula: ([product]/[substrate+product])*100, where 'product' includes the immediate product and all products in the pathway derived from it.

The terms "peroxisome biogenesis factor protein", "peroxin" and "Pex protein" are interchangeable and refer to proteins involved in peroxisome biogenesis and/or that participate in the process of importing cellular proteins by means of ATP hydrolysis through the peroxisomal membrane. The acronym of a gene that encodes any of these proteins is "Pex gene". A system for nomenclature of Pex genes is described by Distel et al., *J. Cell Biol.*, 135:1-3 (1996). At least 32 different Pex genes have been identified so far in various eukaryotic organisms. Many Pex genes have been isolated from the analysis of mutants that demonstrated abnormal peroxisomal functions or structures. Based on a review by Kiel, J. A. K. W., et al. (*Traffic*, 7:1291-1303 (2006)), wherein in silico analysis of the genomic sequences of 17 different fungal species was performed, the following Pex proteins were identified: Pex1p, Pex2p, Pex3p, Pex3Bp, Pex4p, Pex5p, Pex5Bp, Pex5 Cp, Pex5/20p, Pex6p, Pex7p, Pex8p, Pex10p, Pex12p, Pex13p, Pex14p, Pex15p, Pex16p, Pex17p, Pex14/17p, Pex18p, Pex19p, Pex20p, Pex21p, Pex21Bp, Pex22p, Pex22p-like and Pex26p. Thus, each of these proteins is referred to herein as a "Pex protein", a "peroxin" or a "peroxisome biogenesis factor protein", and is encoded by at least one "Pex gene".

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2nd ed., Cold Spring Harbor Laboratory: Cold Spring Harbor, N.Y. (1989), which is hereby incorporated herein by reference, particularly Chapter 11 and Table 11.1. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the thermal melting point ["$T_m$" or "Tm"] for hybrids of nucleic acids having those sequences. The relative stability, corresponding to higher Tm, of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as the Basic Local Alignment Search Tool ["BLAST"] (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation, such as, in situ hybridization of microbial colonies or bacteriophage plaques. In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The skilled artisan, having the benefit of the sequences as reported herein, may now use all or a substantial portion of the disclosed sequences for purposes known to those skilled in this art, based on the methodologies described herein.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably. They refer to nucleic acid fragments wherein changes in one or more nucleotide bases do not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment.

Moreover, the skilled artisan recognizes that homologous nucleic acid sequences are also defined by their ability to hybridize, under moderately stringent conditions, such as 0.5×SSC, 0.1% SDS, 60° C., with the sequences exemplified herein, or to any portion of the nucleotide sequences disclosed herein and which are functionally equivalent thereto. Stringency conditions can be adjusted to screen for moderately similar fragments.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have at least about 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Specificity is typically the function of post-hybridization washes, the important factors being the ionic strength and temperature of the final wash solution. For DNA-DNA hybrids, the thermal melting point ["$T_m$"] can be approximated from the equation of Meinkoth et al., *Anal. Biochem.*, 138:267-284 (1984): $T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; and, low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120 or 240 minutes.

The term "percent identity" refers to a relationship between two or more polypeptide sequences or two or more polynucleotide sequences, as determined by comparing the sequences. "Percent identity" also means the degree of sequence relatedness between polypeptide or polynucleotide sequences, as the case may be, as determined by the percentage of match between compared sequences. "Percent identity" and "percent similarity" can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Preferred methods to determine percent identity are designed to give the best match between the sequences tested. Methods to determine percent identity and percent similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, CABIOS, 5:151-153 (1989); Higgins, D. G. et al., *Comput. Appl. Biosci.*, 8:189-191 (1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. Default parameters for multiple alignment using the Clustal W method of alignment correspond to GAP PENALTY=10, GAP LENGTH PENALTY=0.2, Delay Divergent Seqs (%)=30, DNA Transition Weight=0.5, Protein Weight Matrix=Gonnet Series, DNA Weight Matrix=IUB.

The "BLASTN method of alignment" is an algorithm provided by the National Center for Biotechnology Information ["NCBI"] to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides, from other species, wherein such polypeptides have the same or similar function or activity. Suitable nucleic acid fragments, i.e., isolated polynucleotides encoding polypeptides in the methods and host cells described herein, encode polypeptides that are at least about 70-85% identical, while more preferred nucleic acid fragments encode amino acid sequences that are at least about 85-95% identical to the amino acid sequences reported herein. Although preferred ranges are described above, useful examples of percent identities include any integer percentage from 50% to 100%, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence which codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and which can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; Intl App. Pub. No. WO 99/28508).

The term "operably linked" refers to the association of nucleic acid sequences on a single nucleic acid fragment so that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences in sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA derived from nucleic acid fragments. Expression may also refer to translation of mRNA into a polypeptide. Thus, the term "expression", as used herein, also refers to the production of a functional end-product (e.g., an mRNA or a protein [either precursor or mature]).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic", "recombinant", "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction that is capable of introducing an expression cassette(s) into a cell.

The term "expression cassette" refers to a fragment of DNA containing a foreign gene and having elements in addition to the foreign gene that allow for enhanced expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence, i.e., open reading frame ["ORF"]; and, 3) a 3' untranslated region, i.e., a terminator that in eukaryotes usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct" and "construct" are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain lines displaying the desired expression level and pattern.

The term "sequence analysis software" refers to any computer algorithm or software program that is useful for the analysis of nucleotide or amino acid sequences. "Sequence analysis software" may be commercially available or independently developed. Typical sequence analysis software include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNAS-TAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" means any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

Genes encoding malonyl-CoA synthetases are found in a variety of organisms, such as *Rhizobium, Bradyrhizobium, Mesorhizobium, Azorhizobium, Sinorhizobium, Nitrobacter, Pseudomonas, Rhodopseudomonas, Oligotropha, Methylobacterium* and *Xanthobacter*. See, for example, those provided in Example 1, Table 3, corresponding to SEQ ID NOs: 8-22. The primary role of malonyl-CoA synthetase is the conversion of the substrates malonate and CoA to yield malonyl-CoA, which can then be used to produce fatty acids.

A number of studies have been performed to characterize malonyl-CoA synthetases. For example, the active sites and substrate bindings of the *Rhizobium trifolii* malonyl-CoA synthetase, determined from NMR spectroscopy, site-directed mutagenesis, and comparative modeling methods, reveal details concerning the structure of the folded protein and provide support that histidine residue number 206 (His206) therein was important to enzyme functionality, based on its role in generating the reaction intermediate malonyl-AMP (Jung, J. W., et al., *Protein Sci.*, 9:1294-1303 (2000)). The enzyme possesses several AMP binding motifs, as highlighted in FIG. 3A of Jung et al. Similar analysis concerning the malonyl-CoA synthetase of *Bradyrhizobium japonicum* USDA 110 was performed by Koo, H. M. and Y. S. Kim (*Arch. Biochem. Biophys.*, 378(1):167-74 (2000)).

The malonyl-CoA synthetase sequences in Table 3, or portions of them, may be used to search for malonyl-CoA synthetase homologs in the same or other species using sequence analysis software. In general, such computer software matches similar sequences by assigning degrees of homology to various substitutions, deletions, and other modifications. Use of software algorithms, such as the BLASTP method of alignment with a low complexity filter and the following parameters: Expect value=10, matrix=Blosum 62 (Altschul, et al., *Nucleic Acids Res.*, 25:3389-3402 (1997)), is well-known for comparing any malonyl-CoA synthetase protein in Table 3 against a database of nucleic or protein sequences and thereby identifying similar known sequences within a preferred organism.

Use of a software algorithm to comb through databases of known sequences is particularly suitable for the isolation of homologs having a relatively low percent identity to publicly available malonyl-CoA synthetase sequences, such as those described in Table 3. It is predictable that isolation would be relatively easier for malonyl-CoA synthetase homologs of at least about 70%-85% identity to publicly available malonyl-CoA synthetase sequences. Further, those sequences that are at least about 85%-90% identical would be particularly suitable for isolation and those sequences that are at least about 90%-95% identical would be the most easily isolated.

Some malonyl-CoA synthetase homologs have also been isolated by the use of motifs unique to malonyl-CoA synthetase enzymes. For example, it is well known that malonyl-CoA synthetases all possess AMP binding motifs. This region of "conserved domain" corresponds to a set of amino acids that are highly conserved at specific positions, which likely represents a region of the malonyl-CoA synthetase protein that is essential to the structure, stability or activity of the protein. Motifs are identified by their high degree of conservation in aligned sequences of a family of protein homologues. As unique "signatures", they can determine if a protein with a newly determined sequence belongs to a previously identified protein family. These motifs are useful as diagnostic tools for the rapid identification of novel malonyl-CoA synthetase genes.

Alternatively, the publicly available malonyl-CoA synthetase sequences or their motifs may be hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are hybridizable to the nucleic acid sequence to be detected. Although probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well known. Typically the probe and the sample must be mixed under conditions that permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and the sample nucleic acid occurs. The concentration of probe or target in the mixture determine the time necessary for hybridization to occur. The higher the concentration of the probe or target, the shorter the hybridization incubation time needed. Optionally, a chaotropic agent may be added, such as guanidinium chloride, guanidinium thiocyanate, sodium thiocyanate, lithium tetrachloroacetate, sodium perchlorate, rubidium tetrachloroacetate, potassium iodide or cesium trifluoroacetate. If desired, one can add formamide to the hybridization mixture, typically 30-50% (v/v) ["by volume"].

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution are unlabeled carrier nucleic acids from about 0.1 to 5 mg/mL, fragmented nucleic DNA such as calf thymus or salmon sperm DNA or yeast RNA, and optionally from about 0.5 to 2% wt/vol ["weight by volume"] glycine. Other additives may be included, such as volume exclusion agents that include polar water-soluble or swellable agents (e.g., polyethylene glycol), anionic polymers (e.g., polyacrylate or polymethylacrylate) and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed or covalently coupled to it immobilized nucleic acid probe that is unlabeled and complementary to one portion of the sequence.

Any of the malonyl-CoA synthetase nucleic acid fragments described herein or in public literature, or any identified homologs, may be used to isolate genes encoding homologous proteins from the same or other species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies, such as polymerase chain reaction ["PCR"] (U.S. Pat. No. 4,683,202); ligase chain reaction ["LCR"] (Tabor, S. et al., *Proc. Natl. Acad. Sci. U.S.A.*, 82:1074 (1985)); or strand displacement amplification ["SDA"] (Walker, et al., *Proc. Natl. Acad. Sci. U.S.A.*, 89:392 (1992)); and, 3) methods of library construction and screening by complementation.

For example, genes encoding proteins or polypeptides similar to publicly available malonyl-CoA synthetase genes or their motifs could be isolated directly by using all or a portion of those publicly available nucleic acid fragments as DNA hybridization probes to screen libraries from any desired organism using well known methods. Specific oligonucleotide probes based upon the publicly available nucleic acid sequences can be designed and synthesized by methods known in the art (Maniatis, supra). Moreover, the entire sequences can be used directly to synthesize DNA probes by methods known to the skilled artisan, such as random primers DNA labeling, nick translation or end-labeling techniques, or RNA probes using available in vitro transcription systems. In addition, specific primers can be designed and used to amplify a part or the full length of the publicly available sequences or their motifs. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of available malonyl-CoA synthetase sequences may be used in PCR protocols to amplify longer nucleic acid fragments encoding homologous genes from DNA or RNA. PCR may also be performed on a library of cloned nucleic acid fragments wherein the sequence of one primer is derived from the available nucleic acid fragments or their motifs. The sequence of the other primer takes advantage of the presence of the polyadenylic acid tracts to the 3' end of the mRNA precursor encoding genes.

The second primer sequence may also be based upon sequences derived from the cloning vector. For example, the skilled artisan can follow the RACE protocol (Frohman et al., *Proc. Natl. Acad. Sci. U.S.A.*, 85:8998 (1988)) to generate cDNAs by using PCR to amplify copies of the region between a single point in the transcript and the 3' or 5' end. Primers oriented in the 3' and 5' directions can be designed from the available sequences. Using commercially available 3' RACE or 5' RACE systems (e.g., BRL, Gaithersburg, Md.), specific 3' or 5' cDNA fragments can be isolated (Ohara et al., *Proc. Natl. Acad. Sci. U.S.A.*, 86:5673 (1989); Loh et al., *Science*, 243:217 (1989)).

Based on any of the well-known methods just discussed, it would be possible to identify and/or isolate malonyl-CoA synthetase gene homologs in any preferred organism of choice. The activity of any putative malonyl-CoA synthetase gene can readily be confirmed by standard biochemical assays (e.g., see Kim, Y. S. and S. K. Bang. Anal Biochem., 170(1):45-9 (1988)).

Acetyl-CoA is the principle building block for de novo biosynthesis of fatty acids. Although any compound that can effectively be metabolized to produce acetyl-CoA can serve as a precursor of fatty acids, glucose is often the primary source of carbon. Via glycolysis, glucose is converted to pyruvate, which is transported into the mitochondria to be converted by pyruvate dehydrogenase to acetyl-CoA. Since acetyl-CoA cannot be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ["ACC"; EC 6.4.1.2]. Fatty acid synthesis is catalyzed by a multi-enzyme fatty acid synthase complex ["FAS"; EC 2.3.1.85] and occurs by the condensation of eight two-carbon fragments (acetyl groups from acetyl-CoA) to form a 16-carbon saturated fatty acid, palmitate. More specifically, FAS catalyzes a series of 7 reactions, as summarized below (Smith, S., *FASEB J.*, 8(15):1248-59 (1994)). First, acetyl-CoA and malonyl-CoA are transferred to the acyl carrier peptide ["ACP"] of FAS. The acetyl group is then transferred to the malonyl group, forming β-ketobutyryl-ACP and releasing $CO_2$. Then, β-ketobutyryl-ACP undergoes reduction (via β-ketoacyl reductase) and dehydration (via β-hydroxyacyl dehydratase) to form a trans-monounsaturated fatty acyl group. The double bond is reduced by NADPH, yielding a saturated fatty-acyl group two carbons longer than the initial one. The ability of the butyryl-group to condense with a new malonyl group and repeat the elongation process is then regenerated. When the fatty acyl group becomes 16 carbons long, a thioesterase activity hydrolyses it, releasing free palmitate.

Fatty acid synthesis can be summarized by the following equation (ignoring $H^+$ and water): acetyl-CoA+7 malonyl-CoA+14 NADPH→palmitate+7 $CO_2$+14 $NADP^+$+8 CoA.

Further elongation and oxidation of palmitate can occur in either the mitochondrion or endoplasmic reticulum. Palmitic acid (16:0) and the C2 elongated form stearic acid (18:0) can be unsaturated to their respective monounsaturated forms, i.e., palmitoleic acid (16:1) and oleic acid (18:1). This process is catalyzed at the endoplasmic reticulum membrane and provides fatty acids for phospholipid biosynthesis. Palmitic acid may be transported back to the mitochondrial matrix or peroxisomal matrix for oxidation.

Triacylglycerols ["TAGs"], the primary storage unit for fatty acids, are formed by a series of reactions that involve: 1) esterification of one molecule of acyl-CoA to glycerol-3-phosphate via an acyltransferase to produce lysophosphatidic acid; 2) esterification of a second molecule of acyl-CoA via an acyltransferase to yield 1,2-diacylglycerol phosphate, commonly identified as phosphatidic acid; 3) removal of a phosphate by phosphatidic acid phosphatase to yield 1,2-diacylglycerol ["DAG"]; and, 4) addition of a third fatty acid by the action of an acyltransferase to form the TAG.

A wide spectrum of fatty acids can be incorporated into TAGs, including saturated and unsaturated fatty acids and short-chain and long-chain fatty acids. Some non-limiting examples of fatty acids that can be incorporated into TAGs by acyltransferases include: capric (10:0), lauric (12:0), myristic (14:0), palmitic (16:0), palmitoleic (16:1), stearic (18:0), oleic (18:1), vaccenic (18:1), linoleic (18:2), eleostearic (18:3), γ-linolenic (18:3), α-linolenic (18:3), stearidonic (18:4), arachidic (20:0), eicosadienoic (20:2), dihomo-γ-linolenic (20:3), eicosatrienoic (20:3), arachidonic (20:4), eicosatetraenoic (20:4), eicosapentaenoic (20:5), behenic (22:0), docosapentaenoic (22:5), docosahexaenoic (22:6), lignoceric (24:0), nervonic (24:1), cerotic (26:0) and montanic (28:0) fatty acids.

Described herein are methods for manipulating the content of malonates in a transgenic organism, wherein said malonates comprise the ionised form of malonic acid, as well as its esters and salts. The methods comprise:
  a) providing a transgenic organism useful in fermentation of at least one product where the transgenic organism comprises at least one gene encoding a malonyl-CoA synthetase under the control of suitable regulatory sequences; and,
  b) growing the organism to allow expression of the at least one gene encoding a malonyl-CoA synthetase, such that the transgenic organism makes a reduced amount of malonates as a fermentation byproduct compared with the amount of malonates made by the same organism, whether transgenic or not transgenic, provided that the organism:
    (i) does not comprise a gene encoding malonyl-CoA synthetase; or,
    (ii) comprises a gene encoding malonyl-CoA synthetase that is not expressed.

In some embodiments, the at least one gene encoding a malonyl-CoA synthetase is encoded by an amino acid sequence selected from the group consisting of: SEQ ID NO:2, SEQ ID NO:4, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 and SEQ ID NO:22. The malonyl-CoA synthetase of SEQ ID NO:2 may be encoded by the nucleotide sequence set forth as SEQ ID NO:1 or SEQ ID NO:3, for example.

Perferably, the at least one sequence encoding the malonyl-CoA synthetase is under the control of at least one strong promoter, and one of skill in the art will appreciate that expression of the gene may also be increased by expression in multicopy.

Also described herein are transgenic organisms comprising at least one malonyl-CoA synthetase protein, produced by the methods described above. More specifically, the specification describes a transgenic organism useful in fermentation of at least one product, comprising at least one gene encoding malonyl-CoA synthetase under control of at least one regulatory sequence; wherein the transgenic organism produces a reduced amount of malonates as a fermentation byproduct compared with the amount of malonates produced by the same organism, whether transgenic or not transgenic, provided that the organism:
  a) does not comprise a gene encoding malonyl-CoA synthetase; or,
  b) comprises a gene encoding malonyl-CoA synthetase that is not expressed.

The transgenic organism is preferably selected from the group consisting of algae, fungi, euglenoids, yeast, bacteria and stramenopiles. More preferred are those organisms classified as oleaginous, such that they accumulate at least about 25% of their dry cell weight as oil. For example, preferred oleaginous yeasts include those from the genera *Yarrowia, Candida, Rhodotorula, Rhodosporidium, Cryptococcus, Trichosporon* and *Lipomyces*.

The "at least one product" refers to any biocatalytically-produced primary product(s) of interest which results from the fermentation. The product may be a compound that is naturally produced by the organism or non-native genes may be genetically engineered into the organism for their functional expression in the fermentation, thereby resulting in a product that is not naturally produced by the organism. Notably, the expression of the heterologous malonyl-CoA synthetase will not have a substantial negative impact on the volumetric productivity or the final titer of the at least one product (when compared to the productivity in the same organism, whether transgenic or not transgenic, provided that the organism (i) does not comprise a gene encoding malonyl-CoA synthetase; or, (ii) comprises a gene encoding malonyl-CoA synthetase that is not expressed).

In some embodiments, the transgenic organisms comprising at least one malonyl-CoA synthetase further comprises at least one genetic mutation. For example, Applicants observed that disruption in at least one native peroxisome biogenesis factor protein ["PEX"] in strains of *Yarrowia lipolytica* advantageously led to increased production of polyunsaturated fatty acids ["PUFAs"] in the total lipid fraction and in the oil fraction, concurrent with increased production of byproduct malonates. Construction of several *Y. lipolytica* strains comprising PEX disruptions are described in U.S. patent application Ser. No. 12/244,950 [E.I. du Pont de Nemours & Co. Inc.]; preferred disruptions are within any of the following Pex genes: YlPex1p (GenBank Accession No. CAG82178), YlPex2p (GenBank Accession No. CAG77647), YlPex3p (GenBank Accession No. CAG78565), YlPex3Bp (GenBank Accession No. CAG83356), YlPex4p (GenBank Accession No. CAG79130), YlPex5p (GenBank Accession No. CAG78803), YlPex6p (GenBank Accession No. CAG82306), YlPex7p (GenBank Accession No. CAG78389), YlPex8p (GenBank Accession No. CAG80447), YlPex12p (GenBank Accession No. CAG81532), YlPex13p (GenBank Accession No. CAG81789), YlPex14p (GenBank Accession No. CAG79323), YlPex16p (GenBank Accession No. CAG79622), YlPex17p (GenBank Accession No. CAG84025), YlPex19p (GenBank Accession No. AAK84827), YlPex20p (GenBank Accession No. CAG79226), YlPex22p (GenBank Accession No. CAG77876) and YlPex26p (GenBank Accession No. NC_006072, antisense translation of nucleotides 117230-118387). As described in the Examples, the increased by-production of malonates in these Pex-disrupted strains of *Yarrowia* was substantially reduced by expression of a heterologous malonyl-CoA synthetase, without negatively affecting the PUFA productivity.

Thus, in one preferred embodiment of the present invention, a transgenic *Yarrowia* sp. host cell is described, the host cell comprising:
  a) at least one genetic mutation, wherein the mutation is a disruption in at least one native peroxisome biogenesis factor protein; and,
  b) at least one gene encoding malonyl-CoA synthetase under control of at least one regulatory sequence; and,
  c) genes encoding a functional polyunsaturated fatty acid biosynthetic pathway.

One of skill in the art will be capable of identifying other genetic mutations within the transgenic organism that result in production of unacceptable amounts of malonates during fermentation of the at least one product. Expression of at least one malonyl-CoA synthetase gene under the control of at least one regulatory sequence will result in a transgenic organism that produces a reduced amount of malonates as a fermentation byproduct compared with the amount of malonates produced by the same organism, whether transgenic or not transgenic, provided that the organism (i) does not comprise a gene encoding malonyl-CoA synthetase; or, (ii) comprises a gene encoding malonyl-CoA synthetase that is not expressed.

It is necessary to create and introduce a recombinant construct comprising an open reading frame ["ORF"] encoding malonyl-CoA synthetase into the organism useful in a fermentation. One of skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and 3) screening and isolating of clones. See Sambrook et al., *Molecular Cloning: A Laboratory Manual*, 2$^{nd}$ ed., Cold Spring Harbor Laboratory: Cold Spring Harbor, N.Y. (1989); Maliga et al., Methods in Plant Molecular Biology, Cold Spring Harbor, N.Y. (1995); Birren et al., Genome Analysis: Detecting Genes, v. 1, Cold Spring Harbor, N.Y. (1998); Birren et al., Genome Analysis: Analyzing DNA, v. 2, Cold Spring Harbor: NY (1998); *Plant Molecular Biology: A Laboratory Manual*, Clark, ed. Springer: NY (1997).

In general, the choice of sequences included in the construct depends on the desired expression products, the nature of the host cell and the proposed means of separating transformed cells versus non-transformed cells. The skilled artisan is aware of the genetic elements that must be present on the plasmid vector to successfully transform, select and propagate host cells containing the chimeric gene. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, and a region 3' of the DNA fragment that controls transcriptional termination, i.e., a terminator. It is most preferred when both control regions are derived from genes from the transformed host cell.

Initiation control regions or promoters useful for driving expression of heterologous genes or portions of them in the desired host cell are numerous and well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter, i.e., native, synthetic, or chimeric, capable of directing expression of these genes in the selected host cell is suitable. Expression in a host cell can occur in an induced or constitutive fashion. Induced expression occurs by inducing the activity of a regulatable promoter operably linked to the malonyl-CoA synthetase gene of interest. Constitutive expression occurs by the use of a constitutive promoter operably linked to the gene of interest.

When the host cell is, e.g., yeast, transcriptional and translational regions functional in yeast cells are provided, particularly from the host species. See Intl. App. Pub. No. WO 2006/052870 for preferred transcriptional initiation regulatory regions for use in *Yarrowia lipolytica*. Any number of regulatory sequences may be used, depending on whether constitutive or induced transcription is desired, the efficiency of the promoter in expressing the ORF of interest, the ease of construction, etc.

3' non-coding sequences encoding transcription termination signals, i.e., a "termination region", must be provided in a recombinant construct and may be from the 3' region of the gene from which the initiation region was obtained or from a different gene. A large number of termination regions are known and function satisfactorily in a variety of hosts when utilized in both the same and different genera and species from which they were derived. The termination region is selected more for convenience rather than for any particular property. Termination regions may also be derived from various genes native to the preferred hosts.

Particularly useful termination regions for use in yeast are derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. The 3'-region can also be synthetic, as one of skill in the art can utilize available information to design and synthesize a 3'-region sequence that functions as a transcription terminator. A termination region may be unnecessary, but is highly preferred.

The vector may comprise a selectable and/or scorable marker, in addition to the regulatory elements described above. Preferably, the marker gene is an antibiotic resistance gene such that treating cells with the antibiotic results in growth inhibition, or death, of untransformed cells and uninhibited growth of transformed cells. For selection of yeast transformants, any marker that functions in yeast is useful with resistance to kanamycin, hygromycin and the amino glycoside G418 and the ability to grow on media lacking uracil, lysine, histine or leucine being particularly useful.

Merely inserting a gene into a cloning vector does not ensure its expression at the desired rate, concentration, amount, etc. In response to the need for a high expression rate, many specialized expression vectors have been created by manipulating a number of different genetic elements that control transcription, RNA stability, translation, protein stability and location, oxygen limitation, and secretion from the host cell. Some of the manipulated features include: the nature of the relevant transcriptional promoter and terminator sequences, the number of copies of the cloned gene and whether the gene is plasmid-borne or integrated into the genome of the host cell, the final cellular location of the synthesized foreign protein, the efficiency of translation and correct folding of the protein in the host organism, the intrinsic stability of the mRNA and protein of the cloned gene within the host cell and the codon usage within the cloned gene, such that its frequency approaches the frequency of preferred codon usage of the host cell. Each of these may be used in the methods and host cells described herein to further optimize expression of malonyl-CoA synthetase genes.

After a recombinant construct is created comprising at least one chimeric gene comprising a promoter, a malonyl-CoA synthetase ORF and a terminator, it is placed in a plasmid vector capable of autonomous replication in the host cell or is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

When two or more genes are expressed from separate replicating vectors, each vector may have a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation, e.g., lithium acetate transformation (*Methods in Enzymology*, 194:186-187 (1991)), protoplast fusion, biolistic impact, electroporation, microinjection, vacuum filtration or any other method that introduces the gene of interest into the host cell.

For convenience, a host cell that has been manipulated by any method to take up a DNA sequence, for example, in an expression cassette, is referred to herein as "transformed" or "recombinant". The transformed host will have at least one copy of the expression construct and may have two or more, depending upon whether the gene is integrated into the genome, amplified, or is present on an extrachromosomal element having multiple copy numbers.

The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. Cells expressing the marker protein or tag can be selected, for example, visually, or by techniques such as fluorescence-activated cell sorting or panning using antibodies.

Regardless of the selected host or expression construct, multiple transformants must be screened to obtain a strain or line displaying the desired expression level, regulation and pattern, as different independent transformation events result in different levels and patterns of expression (Jones et al., EMBO J., 4:2411-2418 (1985); De Almeida et al., Mol. Gen. Genetics, 218:78-86 (1989)). Such screening may be accomplished by Southern analysis of DNA blots (Southern, J. Mol. Biol., 98:503 (1975)), Northern analysis of mRNA expression (Kroczek, J. Chromatogr. Biomed. Appl., 618(1-2):133-145 (1993)), Western and/or Elisa analyses of protein expression, phenotypic analysis or iron chromatography analyses of the fermentation broth to detect any changes in the organic acid levels.

A variety of eukaryotic organisms are suitable to serve as a transgenic organism comprising a heterologous malonyl-CoA synthetase, as described in the methods of the present disclosure. Various fungi, algae, oomycetes, yeasts, stramenopiles, bacteria and/or euglenoids that can be grown in a fermenter may be useful hosts.

In some cases, oleaginous organisms are preferred. Oleaginous organisms are naturally capable of oil synthesis and accumulation, commonly accumulating in excess of about 25% of their dry cell weight as oil. Various algae, moss, fungi, yeast, stramenopiles and plants are naturally classified as oleaginous. In alternate embodiments, a non-oleaginous organism can be genetically modified to become oleaginous, e.g., yeast such as Saccharomyces cerevisiae.

More preferred oleaginous microbes include those algal, stramenopile and fungal organisms that naturally produce ω-3/ω-6 PUFAs. For example, ARA, EPA and/or DHA is produced via Cyclotella sp., Nitzschia sp., Pythium, Thraustochytrium sp., Schizochytrium sp. and Mortierella. The method of transformation of M. alpina is described by Mackenzie et al. (Appl. Environ. Microbiol., 66:4655 (2000)). Similarly, methods for transformation of Thraustochytriales microorganisms (e.g., Thraustochytrium, Schizochytrium) are disclosed in U.S. Pat. No. 7,001,772.

More preferred are oleaginous yeasts, including those that naturally produce and those genetically engineered to produce ω-3/ω-6 PUFAs (infra). Genera typically identified as oleaginous yeast include, but are not limited to: Yarrowia, Candida, Rhodotorula, Rhodosporidium, Cryptococcus, Trichosporon and Lipomyces. More specifically, illustrative oil-synthesizing yeasts include: Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis and Yarrowia lipolytica (formerly classified as Candida lipolytica).

The most preferred oleaginous yeast is Yarrowia lipolytica; and most preferred are Y. lipolytica strains designated as ATCC #76982, ATCC #20362, ATCC #8862, ATCC #18944 and/or LGAM S(7)1 (Papanikolaou S., and Aggelis G., Bioresour. Technol., 82(1):43-9 (2002)).

Specific teachings relating to transformation of Yarrowia lipolytica include U.S. Pat. No. 4,880,741 and U.S. Pat. No. 5,071,764 and Chen, D. C. et al. (Appl. Microbiol. Biotechnol., 48(2):232-235 (1997)), while suitable selection techniques are described in U.S. Pat. No. 7,238,482, U.S. Pat. No. 7,259,255 and Intl App. Pub. No. WO 2006/052870.

The preferred method of expressing genes in Yarrowia lipolytica is by integration of linear DNA into the genome of the host. Integration into multiple locations within the genome can be particularly useful when high level expression of genes is desired, such as in the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244 or Aco3: GenBank Accession No. AJ001301), the Δ12 desaturase gene locus (U.S. Pat. No. 7,214,491), the Lip1 gene locus (GenBank Accession No. Z50020), the Lip2 gene locus (GenBank Accession No. AJ012632), the SCP2 gene locus (GenBank Accession No. AJ431362), the Pex3 gene locus (GenBank Accession No. CAG78565), the Pex16 gene locus (Gen Bank Accession No. CAG79622) and/or the Pex10 gene locus (GenBank Accession No. CAG81606).

Preferred selection methods for use in Yarrowia lipolytica include resistance to kanamycin, hygromycin and the amino glycoside G418 and the ability to grow on media lacking uracil, leucine, lysine, tryptophan or histidine. 5-fluoroorotic acid [5-fluorouracil-6-carboxylic acid monohydrate or "5-FOA"] may also be used for selection of yeast Ura⁻ mutants. This compound is toxic to yeast cells that possess a functioning URA3 gene encoding orotidine 5'-monophosphate decarboxylase [OMP decarboxylase]; thus, based on this toxicity, 5-FOA is especially useful for the selection and identification of Ura⁻ mutant yeast strains (Bartel, P. L. and Fields, S., Yeast 2-Hybrid System, Oxford University New York, v. 7, pp 109-147, 1997; see also Intl App. Pub. No. WO 2006/052870 for 5-FOA use in Yarrowia).

An alternate preferred selection method for use in Yarrowia relies on a dominant, non-antibiotic marker for Yarrowia lipolytica based on sulfonylurea (chlorimuron ethyl; E.I. duPont de Nemours & Co., Inc., Wilmington, Del.) resistance. More specifically, the marker gene is a native acetohydroxyacid synthase ("AHAS" or acetolactate synthase; E.C. 4.1.3.18) that has a single amino acid change, i.e., W497L, that confers sulfonyl urea herbicide resistance (Intl App. Pub. No. WO 2006/052870). AHAS is the first common enzyme in the pathway for the biosynthesis of branched-chain amino acids, i.e., valine, leucine, isoleucine, and it is the target of the sulfonylurea and imidazolinone herbicides.

The transgenic organism is grown under conditions that optimize production of the at least one product, while controlling the production of malonates. This will reduce carbon and energy waste within the organism as well as the amount of byproduct organic acids that require neutralization during fermentation while maintaining an optimal pH range within the fermentation waste steam. Optimally, fermentation of the organism comprising the heterologous malyonyl-CoA synthetase will reduce the total cost of manufacture of the at least one product.

In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. For example, the oleaginous yeast of interest, such as Yarrowia lipolytica, is generally grown in a complex medium such as yeast extract-peptone-dextrose broth ["YPD"], a defined minimal media, or a defined minimal media that lacks a component necessary for growth and forces selection of the desired expression cassettes (e.g., Yeast Nitrogen Base (DIFCO Laboratories, Detroit, Mich.)).

Fermentation media for the methods and transgenic organisms described herein must contain a suitable carbon source such as taught in U.S. Pat. No. 7,238,482. Suitable sources of carbon encompass a wide variety of sources, with sugars such as glucose, fructose, glycerol and/or fatty acids being preferred. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the organism and the promotion of the enzymatic pathways that enable production of the at least one product.

It is contemplated that a variety of fermentation process designs (e.g., batch, fed-batch or continuous) may be applied for production of the at least one product. A batch fermentation process is a closed system wherein the media composition is fixed at the beginning of the process and not subject to further additions beyond those required for maintenance of pH and oxygen level during the process. Thus, at the beginning of the culturing process the media is inoculated with the desired organism and growth or metabolic activity occurs without adding additional sources (i.e., carbon and nitrogen sources) to the medium. In batch processes, the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die.

A variation of the standard batch process is the fed-batch process, wherein the carbon source is continually added to the fermenter over the course of the fermentation process. A fed-batch process is also suitable herein. Fed-batch processes are useful when catabolite repression is apt to inhibit the metabolism of the cells or where it is desirable to have limited amounts of carbon source in the media at any one time. Measurement of the carbon source concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, 2nd ed., (1989) Sinauer Associates: Sunderland, Mass.; or Deshpande, Mukund V., Appl. Biochem. Biotechnol., 36:227 (1992).

Alternatively, a continuous fermentation process occurs when a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

DESCRIPTION OF PREFERRED EMBODIMENTS

The metabolic process wherein oleic acid (18:1) is converted to ω-3/ω-6 fatty acids involves elongation of the carbon chain through the addition of carbon atoms and desaturation of the molecule through the addition of double bonds. This requires a series of special elongation and desaturation enzymes present in the endoplasmic reticulum membrane. However, as seen in FIG. 3 and as described below, there are often multiple alternate pathways for production of a specific ω-3/ω-6 fatty acid.

Specifically, FIG. 3 depicts the pathways described below. All pathways require the initial conversion of oleic acid to linoleic acid ["LA"], the first of the ω-6 fatty acids, by a Δ12 desaturase. Then, using the "Δ6 desaturase/Δ6 elongase pathway" and LA as substrate, long-chain ω-6 fatty acids are formed as follows: 1) LA is converted to γ-linolenic acid ["GLA"] by a Δ6 desaturase; 2) GLA is converted to dihomo-γ-linolenic acid ["DGLA"] by a $C_{18/20}$ elongase; 3) DGLA is converted to arachidonic acid ["ARA"] by a Δ5 desaturase; 4) ARA is converted to docosatetraenoic acid ["DTA"] by a $C_{20-22}$ elongase; and, 5) DTA is converted to docosapentaenoic acid ["DPAn-6"] by a Δ4 desaturase.

Alternatively, the "Δ6 desaturase/E6 elongase pathway" can use α-linolenic acid ["ALA"] as substrate to produce long-chain ω-3 fatty acids as follows: 1) LA is converted to ALA, the first of the ω-3 fatty acids, by a Δ15 desaturase; 2) ALA is converted to stearidonic acid ["STA"] by a Δ6 desaturase; 3) STA is converted to eicosatetraenoic acid ["ETA"] by a $C_{18/20}$ elongase; 4) ETA is converted to eicosapentaenoic acid ["EPA"] by a Δ5 desaturase; 5) EPA is converted to docosapentaenoic acid ["DPA"] by a $C_{20/22}$ elongase; and, 6) DPA is converted to docosahexaenoic acid ["DHA"] by a Δ4 desaturase. Optionally, ω-6 fatty acids may be converted to ω-3 fatty acids. For example, ETA and EPA are produced from DGLA and ARA, respectively, by Δ17 desaturase activity.

Alternate pathways for the biosynthesis of ω-3/ω-6 fatty acids utilize Δ9 elongase and Δ8 desaturase, that is, the "Δ9 elongase/Δ8 desaturase pathway". More specifically, LA and ALA may be converted to EDA and ETrA, respectively, by a Δ9 elongase. A Δ8 desaturase then converts EDA to DGLA and/or ETrA to ETA. Downstream PUFAs are subsequently formed as described above.

The transgenic organism herein preferably possesses the ability to produce PUFAs, either naturally or via techniques of genetic engineering. Although many microorganisms can synthesize PUFAs (including ω-3/ω-6 fatty acids) in the ordinary course of cellular metabolism, some of whom could be commercially cultured, few to none of these organisms produce oils having a desired oil content and composition for use in pharmaceuticals, dietary substitutes, medical foods, nutritional supplements, other food products, industrial oleochemicals or other end-use applications. Thus, there is increasing emphasis on the ability to engineer microorganisms for production of "designer" lipids and oils, wherein the fatty acid content and composition are carefully specified by genetic engineering. On this basis, it is expected that the host likely comprises heterologous genes encoding a functional PUFA biosynthetic pathway but not necessarily.

If the host organism does not natively produce the desired PUFAs or possess the desired lipid profile, one skilled in the art is familiar with the considerations and techniques necessary to introduce one or more expression cassettes encoding appropriate enzymes for PUFA biosynthesis into the host organism of choice. Numerous teachings are provided in the literature to one of skill for so introducing such expression cassettes into various host organisms. Some references using the host organism *Yarrowia lipolytica* are provided as follows: U.S. Pat. No. 7,238,482, U.S. Pat. No. 7,465,564, U.S. Pat. No. 7,550,286, U.S. Pat. No. 7,588,931, U.S. Pat. Appl. Pub. No. 2006-0115881-A1 and U.S. Pat. Appl. Pub. No. 2009-0093543-A1. This list is not exhaustive and should not be construed as limiting.

Briefly, a variety of ω-3/ω-6 PUFA products can be produced prior to their transfer to TAGs, depending on the fatty acid substrate and the particular genes of the ω-3/ω-6 fatty acid biosynthetic pathway that are present in or transformed into the host cell. As such, production of the desired fatty acid product can occur directly or indirectly. Direct production occurs when the fatty acid substrate is converted directly into the desired fatty acid product without any intermediate steps or pathway intermediates. Indirect production occurs when multiple genes encoding the PUFA biosynthetic pathway may be used in combination such that a series of reactions occur to produce a desired PUFA. Specifically, it may be desirable to transform an oleaginous yeast with an expression cassette comprising a Δ12 desaturase, Δ6 desaturase, a $C_{18/20}$ elongase, a Δ5 desaturase and a Δ17 desaturase for the overproduction of EPA. See U.S. Pat. No. 7,238,482 and Inn App. Pub. No. WO 2006/052870. As is well known to one skilled in the art, various other combinations of genes encoding enzymes of the PUFA biosynthetic pathway may be useful to express in an oleaginous organism (see FIG. 3). The particular genes included within a particular expression cassette depend on the host organism, its PUFA profile and/or desaturase/elongase profile, the availability of substrate and the desired end product(s).

A number of candidate genes having the desired desaturase and/or elongase activities can be identified according to publicly available literature, such as GenBank, the patent literature, and experimental analysis of organisms having the ability to produce PUFAs. Useful desaturase and elongase sequences may be derived from any source, e.g., isolated from a natural source such as from bacteria, algae, fungi, oomycete, yeast, plants, animals, etc., produced via a semisynthetic route or synthesized de novo. Following the identification of these candidate genes, considerations for choosing a specific polypeptide having desaturase or elongase activity include: 1) the substrate specificity of the polypeptide; 2) whether the polypeptide or a component thereof is a rate-limiting enzyme; 3) whether the desaturase or elongase is essential for synthesis of a desired PUFA; 4) cofactors required by the polypeptide; 5) whether the polypeptide is modified after its production, such as by a kinase or a prenyl-transferase; and/or, 6) whether the polypeptide is physically within an appropriate cellular location following its production.

The expressed polypeptide preferably has parameters compatible with the biochemical environment of its location in the host cell. See U.S. Pat. No. 7,238,482. It may also be useful to consider the conversion efficiency of each particular desaturase and/or elongase. More specifically, since each enzyme rarely functions with 100% efficiency to convert substrate to product, the final lipid profile of un-purified oils produced in a host cell is typically a mixture of various PUFAs consisting of the desired ω-3/ω-6 fatty acid, as well as various upstream intermediary PUFAs. Thus, the conversion efficiency of each enzyme is also a variable to consider when optimizing biosynthesis of a desired fatty acid.

Typically, accumulation of significant amounts of PUFAs and TAGs in oleaginous yeast cells requires a two-stage process, since the metabolic state must be "balanced" between growth and synthesis/storage of fats (see, U.S. Pat. No. 7,238,482). In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. Often, the carbon/nitrogen ratio is greater than about 40, preferably greater than about 50, and more preferably greater than about 60. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil.

Preferred growth media for the methods and host cells described herein are common commercially prepared media, such as Yeast Nitrogen Base (DIFCO Laboratories, Detroit, Mich.). Other defined or synthetic growth media may also be used and the appropriate medium for growth of the transgenic organism is well known in microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992).

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and, 3) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2nd ed., Sinauer Associates Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), New England Biolabs, Inc. (Beverly, Mass.), GIBCO/BRL (Gaithersburg, Md.), or Sigma Chemical Company (St.

Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Unless otherwise indicated herein comparisons of genetic sequences were accomplished using DNASTAR software (DNASTAR Inc., Madison, Wis.). The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "pmole" mean micromole(s), "g" means gram(s), "μg" means microgram(s), "ng" means nanogram(s), "U" means unit(s), "bp" means base pair(s) and "kB" means kilobase(s).

Nomenclature For Expression Cassettes:

The structure of an expression cassette is represented by a simple notation system of "X::Y::Z", wherein X describes the promoter fragment, Y describes the gene fragment, and Z describes the terminator fragment, which are all operably linked to one another.

Transformation And Cultivation of *Yarrowia lipolytica*

*Yarrowia lipolytica* strain ATCC #20362 was purchased from the American Type Culture Collection (Rockville, Md.). *Yarrowia lipolytica* strains were routinely grown at 28-30° C. in several media, according to the recipes shown below.

High Glucose Media (HGM) (per liter): 80 glucose, 2.58 g $KH_2PO_4$ and 5.36 g $K_2HPO_4$, pH 7.5 (do not need to adjust).

Fermentation medium (FM) (per liter): 6.70 g/L Yeast nitrogen base, 6.00 g $KH_2PO_4$, 2.00 g $K_2HPO_4$, 1.50 g $MgSO_4*7H_2O$, 20 g glucose, and 5.00 g Yeast extract (BBL).

Transformation of *Y. lipolytica* was performed as described in U.S. Pat. Appl. Pub. No. 2009-0093543-A1, hereby incorporated herein by reference.

Isolation of *Yarrowia lipolytica* Strain Y4305U

Strain Y4305U, producing EPA relative to the total lipids via expression of a Δ9 elongase/Δ8 desaturase pathway, was generated as described in the General Methods of U.S. Pat. App. Pub. No. 2008-0254191, hereby incorporated herein by reference. Briefly, as diagrammed in FIG. 4, strain Y4305U was derived from *Yarrowia lipolytica* ATCC #20362 via construction of strain Y2224 (a FOA resistant mutant from an autonomous mutation of the Ura3 gene of wildtype *Yarrowia* strain ATCC #20362), strain Y4001 (producing 17% EDA with a Leu-phenotype), strain Y4001U1 (Leu - and Ura-), strain Y4036 (producing 18% DGLA with a Leu-phenotype), strain Y4036U (Leu- and Ura-), strain Y4070 (producing 12% ARA with a Ura-phenotype), strain Y4086 (producing 14% EPA), strain Y4086U1 (Ura3-), strain Y4128 (producing 37% EPA; deposited with the American Type Culture Collection on Aug. 23, 2007, bearing the designation ATCC PTA-8614), strain Y4128U3 (Ura-), strain Y4217 (producing 42% EPA), strain Y4217U2 (Ura-), strain Y4259 (producing 46.5% EPA), strain Y4259U2 (Ura-) and strain Y4305 (producing 53.2% EPA relative to the total TFAs).

The complete lipid profile of strain Y4305 was as follows: 16:0 (2.8%), 16:1 (0.7%), 18:0 (1.3%), 18:1 (4.9%), 18:2 (17.6%), ALA (2.3%), EDA (3.4%), DGLA (2.0%), ARA (0.6%), ETA (1.7%), and EPA (53.2%). The total lipid % dry cell weight ["DCW"] was 27.5.

The final genotype of strain Y4305 with respect to wild type *Yarrowia lipolytica* ATCC #20362 was SCP2- (YALI0E01298g), YALI0C18711g-, Pex10-, YALI0F24167g-, unknown 1-, unknown 3-, unknown 8-, GPD::FmD12::Pex20, YAT1::FmD12::OCT, GPM/FBAIN:: FmD12S::OCT, EXP1::FmD12S::Aco, YAT1::FmD12S:: Lip2, YAT1::ME3S::Pex16, EXP1::ME3S::Pex20 (3 copies), GPAT::EgD9e::Lip2, EXP1::EgD9eS::Lip1, FBAINm:: EgD9eS::Lip2, FBA::EgD9eS::Pex20, GPD::EgD9eS::Lip2, YAT1::EgD9eS::Lip2, YAT1::E389D9eS::OCT, FBAINm:: EgD8M::Pex20, FBAIN::EgD8M::Lip1 (2 copies), EXP1:: EgD8M::Pex16, GPDIN::EgD8M::Lip1, YAT1::EgD8M:: Aco, FBAIN::EgD5::Aco, EXP1::EgD5S::Pex20, YAT1:: EgD5S::Aco, EXP1::EgD5S::ACO, YAT1::RD5S::OCT, YAT1::PaD17S::Lip1, EXP1::PaD17::Pex16, FBAINm:: PaD17::Aco, YAT1::YICPT1::ACO, GPD::YICPT1::ACO (wherein FmD12 is a *Fusarium moniliforme* Δ12 desaturase gene [U.S. Pat. No. 7,504,259]; FmD12S is a codon-optimized Δ12 desaturase gene, derived from *Fusarium moniliforme* [U.S. Pat. No. 7,504,259]; ME3S is a codon-optimized $C_{16/18}$ elongase gene, derived from *Mortierella alpina* [U.S. Pat. No. 7,470,532]; EgD9e is a *Euglena gracilis* Δ9 elongase gene [Intl App. Pub. No. WO 2007/061742]; EgD9eS is a codon-optimized Δ9 elongase gene, derived from *Euglena gracilis* [Intl App. Pub. No. WO 2007/061742]; E389D9eS is a codon-optimized Δ9 elongase gene, derived from *Eutreptiella* sp. CCMP389 [Inn App. Pub. No. WO 2007/061742]; EgD8M is a synthetic mutant Δ8 desaturase [Inn App. Pub. No. WO 2008/073271], derived from *Euglena gracilis* [U.S. Pat. No. 7,256,033]; EgD5 is a *Euglena gracilis* Δ5 desaturase [U.S. Pat. App. Pub. No. 2007-0292924]; EgD5S is a codon-optimized Δ5 desaturase gene, derived from *Euglena gracilis* [U.S. Pat. App. Pub. No. 2007-0292924]; RD5S is a codon-optimized Δ5 desaturase, derived from *Peridinium* sp. CCMP626 [U.S. Pat. App. Pub. No. 2007-0271632]; PaD17 is a *Pythium* aphanidermatum Δ17 desaturase [U.S. Pat. No. 7,556,949]; PaD17S is a codon-optimized Δ17 desaturase, derived from *Pythium* aphanidermatum [U.S. Pat. No. 7,556, 949]; and, YICPT1 is a *Yarrowia lipolytica* diacylglycerol cholinephosphotransferase gene [Intl App. Pub. No. WO 2006/052870]).

The Ura3 gene was subsequently disrupted in strain Y4305 (as described in the General Methods of U.S. Pat. App. Pub. No. 2008-0254191), such that a Ura3 mutant gene was integrated into the Ura3 gene of strain Y4305. Following selection of the transformants and analysis of the FAMEs, transformants #1, #6 and #7 were determined to produce 37.6%, 37.3% and 36.5% EPA of total lipids when grown on MM+5-FOA plates. These three strains were designated as strains Y4305U1, Y4305U2 and Y4305U3, respectively, and are collectively identified as strain Y4305U.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMEs"] were prepared by transesterification of the lipid extract with sodium methoxide (Roughan, G., and Nishida I., *Arch Biochem Biophys.*, 276 (1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Identification of Publicly Available Genes Encoding Malonyl-CoA Synthetase

A gene cluster was identified to encode malonyl-CoA decarboxylase (MatA), malonyl-CoA synthetase (MatB) and a putative dicarboxylate carrier protein (MatC) in *Rhizobium trifolii* (An, J. H, & Y. S. Kim, Eur. J. Biochem., 257:395-402 (1998)).

Using the protein sequence encoding the *Rhizobium trifolii* malonyl-CoA synthetase (GenBank Accession No. AF117694 and No. AAC83455; SEQ ID NO:5), National Center for Biotechnology Information ["NCBI"] BLASTP 2.2.19 (Basic Local Alignment Search Tool; Altschul, S. F., et al., *Nucleic Acids Res.*, 25:3389-3402 (1997); Altschul, S. F., et al., *FEBS J.*, 272:5101-5109 (2005)) searches were conducted to identify sequences having similarity within the BLAST "nr" database (comprising all non-redundant GenBank CDS translations, the Protein Data Bank ["PDB"] protein sequence database, the SWISS-PROT protein sequence database, the Protein Information Resource ["PIR"] protein sequence database and the Protein Research Foundation ["PRF"] protein sequence database, excluding environmental samples from whole genome shotgun ["WGS"] projects).

The results of the BLASTP comparison summarizing the sequence to which SEQ ID NO:5 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

A large number of proteins were identified as sharing significant similarity to the *Rhizobium trifolii* malonyl-CoA synthetase (GenBank Accession No. AAC83455; SEQ ID NO:5). Table 3 provides a partial summary of those hits having an Expectation value equal to "0.0" and annotation that specifically identified the protein as a "malonyl-CoA synthetase", although this should not be considered as limiting to the disclosure herein. The proteins in Table 3 shared between 64% to 94% identity with SEQ ID NO:5.

TABLE 3

Some Publicly Available Genes Encoding Malonyl-CoA Synthetase

| GenBank Accession No. | Organism | SEQ ID NO |
|---|---|---|
| YP_766603 | *Rhizobium leguminosarum* bv. *viciae* 3841 | SEQ ID NO: 2 |
| YP_468459 | *Rhizobium etli* CFN 42 | SEQ ID NO: 8 |
| YP_001313848 | *Sinorhizobium medicae* WSM419 | SEQ ID NO: 9 |
| YP_674146 | *Mesorhizobium* sp. BNC1 | SEQ ID NO: 10 |
| NP_105559 | *Mesorhizobium loti* MAFF303099 | SEQ ID NO: 11 |
| YP_001236428 | *Bradyrhizobium* sp. BTAi1 | SEQ ID NO: 12 |
| YP_779412 | *Rhodopseudomonas palustris* BisA53 | SEQ ID NO: 13 |
| YP_001526214 | *Azorhizobium caulinodans* ORS 571 | SEQ ID NO: 14 |
| YP_567622 | *Rhodopseudomonas palustris* BisB5 | SEQ ID NO: 15 |
| YP_001202443 | *Bradyrhizobium* sp. ORS278 | SEQ ID NO: 16 |
| YP_001415433 | *Xanthobacter autotrophicus* Py2 | SEQ ID NO: 17 |
| YP_483951 | *Rhodopseudomonas palustris* HaA2 | SEQ ID NO: 18 |
| YP_002210100 | *Oligotropha carboxidovorans* OM5 | SEQ ID NO: 19 |
| NP_945574 | *Rhodopseudomonas palustris* CGA009 | SEQ ID NO: 20 |
| NP_767149 | *Bradyrhizobium japonicum* USDA 110 | SEQ ID NO: 21 |
| ZP_00629462 | *Paracoccus denitrificans* PD1222 | SEQ ID NO: 22 |

Example 2

Synthesis of A Codon-Optimized Malonyl-CoA Synthetase Gene of *Rhizobium leguminosarum* bv. *viciae* 3841 for *Yarrowia lipolytica*

The codon usage of the malonyl-CoA synthetase gene of *Rhizobium leguminosarum* bv. *viciae* 3841 was optimized for expression in *Yarrowia lipolytica*, in a manner similar to that described in U.S. Pat. No. 7,125,672.

Specifically, a codon-optimized malonyl-CoA synthetase gene (designated "MCS", SEQ ID NO:3) was designed based on the coding sequence of the malonyl-CoA synthetase gene from *Rhizobium leguminosarum* bv. *viciae* 3841 ("rMCS"; SEQ ID NOs:1 and 2, corresponding to GenBank Accession No. YP_766603) according to the *Yarrowia* codon usage pattern (U.S. Pat. No. 7,125,672), the consensus sequence around the 'ATG' translation initiation codon, and the general rules of RNA stability (Guhaniyogi, G. and J. Brewer, *Gene*, 265(1-2):11-23 (2001)). In addition to modification of the translation initiation site, 233 bp of the 1515 bp coding region (including the stop codon) were modified (15.4%; FIG. 1) and 219 codons were optimized (43.4%). The GC content was reduced from 61.4% within the wild type gene (i.e., rMCS) to 55.6% within the synthetic gene (i.e., MCS). The translation initiation codon 'ATG' was added in front of the rMCS gene (SEQ ID NO:1) since *Yarrowia* cannot use the 'GTG' codon for translation initiation. A NcoI site and NotI sites were incorporated around the translation initiation codon and after the stop codon of MCS, respectively. The codon-optimized MCS gene (SEQ ID NO:3) is 1518 bp encoding a peptide of 505 amino acids and a stop codon (SEQ ID NO:4). The designed MCS gene was synthesized by GenScript Corporation (Piscataway, N.J.) and cloned into pUC57 (GenBank Accession No. Y14837) to generate pMCS (SEQ ID NO:6).

Example 3

Generation of Construct pZP2-MCS, Comprising the Synthetic Malonyl-CoA Synthetase Plasmid pZP2-MCS (FIG. 2) was constructed to enable expression of the synthetic, codon-optimized malonyl-CoA synthetase gene derived from *Rhizobium leguminosarum* bv.

*viciae* 3841 (Example 2) in the oleaginous yeast, *Yarrowia lipolytica*. The pZP2-MCS plasmid contained the following components listed in Table 4.

TABLE 4

Description of Plasmid pZP2-MCS (SEQ ID NO: 7)

| RE Sites And Nucleotides Within SEQ ID NO: 7 | Description Of Fragment And Chimeric Gene Components |
|---|---|
| BsiWI/AscI (318-1128) | 803 bp 5' portion of *Yarrowia* Pox2 gene (GenBank Accession No. AJ001300) |
| SphI/PacI (3836-4491) | 649 bp 3' portion of *Yarrowia* Pox2 gene (GenBank Accession No. AJ001300) |
| SwaI/BsiWI (6713-318) | FBAIN::MCS::Pex20, comprising: FBAIN: *Yarrowia lipolytica* FBAIN promoter (U.S. Pat. No. 7,202,356); MCS: codon-optimized malonyl-CoA synthetase (SEQ ID NO: 3), derived from *Rhizobium leguminosarum* bv. *viciae* 3841 (GenBank Accession No. YP_766603; SEQ ID NO: 1); Pex20: Pex20 terminator sequence from *Yarrowia* Pex20 gene (GenBank Accession No. AF054613) |
| (4494-5981) | Ura3: *Yarrowia* Ura3 gene (GenBank Accession No. AJ306421) |

Example 4

Effect of Malonyl-CoA Synthetase Gene Expression on Malonates in *Yarrowia lipolytica* Strain Y4305U Plasmid pZP2-MCS was digested with SphI and AscI. A 6.4 kB linear fragment containing the MCS gene under the control of the FBAIN promoter and the *Y. lipolytica* URA3 gene, flanked by the 5' and 3' region of the *Y. lipolytica* PDX2 gene, was separated by agarose gel electrophoresis and purified with a Qiagen gel purification kit according to the manufacturer's protocol. The purified DNA fragment was used to transform the Ura3-strain of Y4305, Y4305U (General Methods), using standard transformation procedures.

Three Ura+ transformants were tested for lipid content, fatty acid profile and malonate production; strain Y4305 was also analyzed similarly as a control. Briefly, cells were grown for 48 hrs in 25 mL of FM medium in a 125 mL flask. Each culture (5 mL) was centrifuged to collect cells. Cells from each culture were resuspended in 25 mL HGM medium and allowed to grow for 5 more days at 30° C. and 250 rpm. Fatty acid profile and total lipid content were determined as described in the General Methods.

To analyze the concentration of malonates in the culture supernatant by ion chromatography, samples were prepared as follows. 1 mL of a culture medium sample was centrifuged at 13,000 rpm for 10 min. Supernatant was collected. Supernatant (0.5 mL) was then put into a PALL nanosep MF 0.2 μm (PALL Corporation, East Hills, N.Y.; Cat. No. P/N ODM02C35) spin tube and the tube was placed in a microfuge and spun at 13,000 rpm for 15 min. The filtrate was then diluted with nano-pure water to achieve a concentration between 0.001 g/L to 0.250 g/L. The analytical vials used for the analysis were Agilent Technologies (Palo Alto, Calif.) screw cap vials (Cat. No. P/N 5182-0715).

Concentration of malonates was determined by ion chromatography with a Dionex DX600 System and a ThermoFinnigan MSQ Mass Spectrometer. System details, provided by Dionex Corporation (Sunnyvale, Calif.), are as follows: IonPac AG11-HC 2×50 mm Guard Column, Cat. No. P/N 052963; IonPac AS11-HC 2×250 mm Analytical Column, Cat. No. P/N 052961; ASRS Ultra-II 2 mm Self-Regenerating Suppressor, Cat. No. P/N 061562; Chromeleon Control software, version 6.80. The method used two detectors in series for both conductivity and mass analysis of the compounds of interest. A gradient concentration of mobile phase, i.e., KOH, was applied over the total run time to separate a variety of organic acids. The gradient was typically 0.5 mM to 60 mM KOH over 64 min to achieve good peak separation and resolution for all the organic acids and inorganic anions. The conductivity detector quantitatively determined the compound based on a standard calibration curve developed from external standards. The mass spec was used in both the Total Ion Current ["TIC"] and Selective Ion Monitoring ["SIM"] modes for detecting and identifying each compound and in some cases for quantifying compounds that co-eluted and that could not be resolved by conductivity.

Malonates elute at 28.49 min. Quantitation was done by comparing peak area with that of known amounts of malonate standard (Fluka, Aigma-Aldrich, Switzerland).

Total lipid (TFAs % DCW), EPA as a % of TFAs, and EPA as a % of DCW for each strain are shown below in Table 5, in addition to the concentration of malonates in each culture. The average fatty acid composition and average malonate concentration of *Y. lipolytica* Y4305 control strains and Y4305U strains expressing the codon-optimized malonyl-CoA synthetase are highlighted in bold text.

More specifically, the term "total fatty acids" ["TFAs"] herein refer to the sum of all cellular fatty acids that can be derivitized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including the phosphatidylcholine and phosphatidylethanolamine fractions) but not free fatty acids.

The term "total lipid content" of cells is a measure of TFAs as a percent of the dry cell weight ["DCW"], although total lipid content can be approximated as a measure of FAMEs as a percent of the DCW ["FAMEs DCW"]. Thus, total lipid content ["TFAs % DCW"] is equivalent to, e.g., milligrams of total fatty acids per 100 milligrams of DCW.

The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., EPA of total lipids is equivalent to EPA % TFAs).

In some cases, it is useful to express the content of a given fatty acid(s) in a cell as its weight percent of the dry cell weight ["% DCW"]. Thus, for example, eicosapentaenoic acid % DCW would be determined according to the following formula: [(eicosapentaenoic acid % TFAs)*(TFAs DCW)]/100. The content of a given fatty acid(s) in a cell as its weight percent of the dry cell weight ["% DCW"] can be approximated, however, as: [(eicosapentaenoic acid % TFAs)*(FAMEs % DCW)]/100.

TABLE 5

Concentration Of Malonates In Transformant
*Yarrowia lipolytica* Strain Y4305U

| Sample | TFAs % DCW | EPA (% TFAs) | EPA (% DCW) | Malonate (g/g DCW) |
|---|---|---|---|---|
| Y4305-A | 36.8 | 49.8 | 18.3 | 0.462 |
| Y4305-B | 35.3 | 48.8 | 17.2 | 0.434 |
| Y4305 Average | 36.05 | 49.3 | 17.75 | 0.448 |
| Y4305U-MCS-1 | 35.2 | 50.7 | 17.9 | 0.029 |
| Y4305U-MCS-2 | 34.5 | 49.2 | 17.0 | 0.025 |
| Y4305U-MCS-3 | 36.2 | 49.5 | 17.9 | 0.026 |

TABLE 5-continued

Concentration Of Malonates In Transformant
*Yarrowia lipolytica* Strain Y4305U

| Sample | TFAs % DCW | EPA (% TFAs) | EPA (% DCW) | Malonate (g/g DCW) |
|---|---|---|---|---|
| Y4305U-MCS Average | 35.3 | 49.8 | 17.6 | 0.027 |

As shown in Table 5, the pZP2-MCS transformants (identified as Y4305U-MCS-1, Y4305U-MCS-2 and Y4305U-MCS-3) all showed markedly lower levels of malonates in the culture supernatant, as compared to the level of malonates in the duplicate cultures of strain Y4305. The profile of fatty acids and the yield of total lipids are similar to the control Y4305 cells. Expression of the malonyl-CoA synthetase, i.e., SEQ ID NO:3, lowered the total amount of malonates (g/g DCW) ~94% without impacting either the fatty acid profile or the total lipid yield as a % DCW.

What is claimed is:

1. A transgenic oleaginous yeast that ferments at least one product, wherein the yeast comprises:
   (i) at least one gene encoding malonyl-CoA synthetase that has the amino acid sequence of SEQ ID NO:4, wherein said gene is operably linked to at least one regulatory sequence; and
   (ii) genes that encode enzymes that catalyze production of at least one polyunsaturated fatty acid, wherein said genes are selected from the group consisting of delta-4 desaturase, delta-5 desaturase, delta-6 desaturase, delta-12 desaturase, delta-15 desaturase, delta-17 desaturase, delta-9 desaturase delta-8 desaturase delta-9 elongase, $C_{14/16}$ elongase, $C_{16/18}$ elongase, $C_{18/20}$ elongase, and $C_{20/22}$ elongase;
   wherein the transgenic oleaginous yeast produces a reduced amount of malonates as a fermentation byproduct compared with the amount of malonates produced by a control oleaginous yeast.

2. The transgenic oleaginous yeast of claim 1, wherein said yeast accumulates oil in an amount of at least 25% of its dry cell weight.

3. The transgenic oleaginous yeast of claim 2, wherein said yeast is selected from the group consisting of *Yarrowia, Candida, Rhodotorula, Rhodosporidium, Cryptococcus, Trichosporon* and *Lipomyces*.

4. The transgenic oleaginous yeast of claim 1, wherein the at least one regulatory sequence comprises a strong promoter.

5. The transgenic oleaginous yeast of claim 1 or 4, wherein the at least one gene encoding malonyl-CoA synthetase is in multicopy.

6. The transgenic oleaginous yeast of claim 1, wherein the malonyl-CoA synthetase is encoded by SEQ ID NO:3.

7. The transgenic oleaginous yeast of claim 1, wherein a titer of the at least one product in the transgenic oleaginous yeast is not reduced relative to the titer of the at least one product produced by the control yeast.

8. The transgenic oleaginous yeast of claim 3, wherein the yeast is *Yarrowia*.

9. The transgenic oleaginous yeast of claim 6, wherein said yeast is selected from the group consisting of *Yarrowia, Candida, Rhodotorula, Rhodosporidium, Cryptococcus, Trichosporon*, and *Lipomyces*.

10. The transgenic oleaginous yeast of claim 9, wherein the yeast is *Yarrowia*.

* * * * *